US008518671B2

(12) United States Patent
Grenier et al.

(10) Patent No.: US 8,518,671 B2
(45) Date of Patent: *Aug. 27, 2013

(54) SOLID SUPPORT ASSAY SYSTEMS AND METHODS UTILIZING NON-STANDARD BASES

(75) Inventors: Jennifer K. Grenier, Madison, WI (US); David J. Marshall, Madison, WI (US); James R. Prudent, Madison, WI (US); Craig S. Richmond, Madison, WI (US); Eric B. Roesch, Oregon, WI (US); Christopher W. Scherrer, Rio, WI (US); Christopher B. Sherrill, Madison, WI (US); Jerod L. Ptacin, Beloit, WI (US)

(73) Assignee: Luminex Corporation, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/478,586

(22) Filed: May 23, 2012

(65) Prior Publication Data

US 2012/0295808 A1    Nov. 22, 2012

Related U.S. Application Data

(60) Division of application No. 11/490,319, filed on Jul. 20, 2006, now Pat. No. 8,217,160, which is a continuation of application No. 11/284,307, filed on Nov. 19, 2005, now Pat. No. 7,892,796, which is a continuation of application No. 09/977,615, filed on Oct. 15, 2001, now Pat. No. 6,977,161, and a continuation-in-part of application No. 09/861,292, filed on May 18, 2001, now Pat. No. 7,422,850.

(60) Provisional application No. 60/293,259, filed on May 22, 2001, provisional application No. 60/282,831, filed on Apr. 10, 2001, provisional application No. 60/240,397, filed on Oct. 14, 2000, provisional application No. 60/240,398, filed on Oct. 14, 2000, provisional application No. 60/205,712, filed on May 19, 2000.

(51) Int. Cl.
*C12P 19/34* (2006.01)
*C12Q 1/68* (2006.01)
*C07H 21/02* (2006.01)
*C07H 21/04* (2006.01)
*C07H 21/00* (2006.01)

(52) U.S. Cl.
USPC ........ 435/91.2; 435/6.1; 435/6.11; 435/6.12; 435/91.1; 536/23.1; 536/24.3; 536/24.33; 536/25.3

(58) Field of Classification Search
USPC .......... 435/6.1, 6.11, 6.12, 91.1, 91.2, 91.51, 435/183, 287.1, 287.2; 436/94, 501; 536/23.1, 536/24.3, 24.33, 25.3

See application file for complete search history.

(56) References Cited

U.S. PATENT DOCUMENTS

| | | | |
|---|---|---|---|
| 4,458,066 A | 7/1984 | Caruthers et al. | |
| 4,683,195 A | 7/1987 | Mullis et al. | |
| 4,683,202 A | 7/1987 | Mullis | |
| 4,800,159 A | 1/1989 | Mullis et al. | |
| 4,996,143 A | 2/1991 | Heller et al. | |
| 5,200,314 A | 4/1993 | Urdea | |
| 5,210,015 A | 5/1993 | Gelfand et al. | |
| 5,432,272 A | 7/1995 | Benner | |
| 5,589,329 A | 12/1996 | Winkler et al. | |
| 5,604,097 A | 2/1997 | Brenner | |
| 5,605,794 A | 2/1997 | Rust et al. | |
| 5,654,138 A | 8/1997 | Lerman | |
| 5,679,524 A | 10/1997 | Nikiforov et al. | |
| 5,681,702 A | 10/1997 | Collins et al. | |
| 5,736,330 A | 4/1998 | Fulton | |
| 5,780,233 A | 7/1998 | Guo et al. | |
| 5,843,669 A | 12/1998 | Kaiser et al. | |
| 5,846,717 A | 12/1998 | Brow et al. | |
| 5,856,092 A | 1/1999 | Dale et al. | |
| 5,866,337 A * | 2/1999 | Schon .......................... | 435/6.18 |
| 5,928,869 A | 7/1999 | Nadeau et al. | |
| 5,965,364 A | 10/1999 | Benner | |
| 5,980,861 A | 11/1999 | Hnatowich et al. | |
| 6,001,983 A | 12/1999 | Benner | |
| 6,007,984 A | 12/1999 | Wang et al. | |
| 6,037,120 A | 3/2000 | Benner | |
| 6,046,807 A | 4/2000 | Chandler | |

(Continued)

FOREIGN PATENT DOCUMENTS

| | | |
|---|---|---|
| EP | 0 382 433 | 8/1990 |
| EP | 0 416 815 | 3/1991 |

(Continued)

OTHER PUBLICATIONS

Beaucage et al., "Deoxynucleoside phosphoramidites—A new class of key intermediates for deoxypolynucleotide synthesis," *Tetrahedron Letters*, 22(20): 1859-1862, 1981. Borer et al., "Stability of ribonucleic acid double-stranded helices," *J. Mol. Biol.*, 86(4):843-853, 1974.
Brown et al., "Chemical synthesis and cloning of tyrosine tRNA gene," *Methods in Enzymology*, 68:109-51, 1979.
Bult et al., "Complete genome sequence of the ethanogenic archaeon, *Methanococcus jannaschii*," *Science*, 273:1058-1073, 1996.
Cantor, "Lighting up hybridization," *Nature Biotechnology*, 14(3):264, 1996.
Chou et al., "Solid-phase synthesis and high-resolution NMR studies of two synthetic double-helical RNA dodecamers: r(CGCGAAUUCGCG) and r(CGCGUAUACGCG)," *Biochemistry*, 28:2422-2435, 1989.

(Continued)

*Primary Examiner* — Frank Lu
(74) *Attorney, Agent, or Firm* — ParkerHighlander PLLC

(57) ABSTRACT

Solid support assays using non-standard bases are described. A capture oligonucleotide comprising a molecular recognition sequence is attached to a solid support and hybridized with a target. In some instances, the molecular recognition sequence includes one or more non-standard bases and hybridizes to a complementary tagging sequence of the target oligonucleotide. In other instances, incorporation of a non-standard base (e.g., via PCR or ligation) is used in the assay.

12 Claims, 17 Drawing Sheets

(56) References Cited

U.S. PATENT DOCUMENTS

| | | | |
|---|---|---|---|
| 6,057,107 A | 5/2000 | Fulton | |
| 6,077,668 A | 6/2000 | Kool | |
| 6,140,496 A | 10/2000 | Benner | |
| 6,232,462 B1 | 5/2001 | Collins et al. | |
| 6,287,766 B1 | 9/2001 | Nolan et al. | |
| 6,294,336 B1 | 9/2001 | Boyce-Jacino et al. | |
| 6,511,809 B2 | 1/2003 | Baez et al. | |
| 6,548,250 B1 | 4/2003 | Sorge | |
| 6,783,985 B1 | 8/2004 | Roemer et al. | |
| 6,830,889 B1 | 12/2004 | Matsumoto et al. | |
| 6,833,257 B2 | 12/2004 | Lee et al. | |
| 6,977,161 B2* | 12/2005 | Grenier et al. | 435/91.2 |
| 7,033,757 B2 | 4/2006 | Makrigiorgos | |
| 7,892,796 B2* | 2/2011 | Prudent et al. | 435/91.2 |
| 2002/0132221 A1 | 9/2002 | Chee et al. | |
| 2003/0194705 A1 | 10/2003 | Schroth | |

FOREIGN PATENT DOCUMENTS

| | | |
|---|---|---|
| EP | 0 416 817 | 3/1991 |
| EP | 0 742 287 | 11/1996 |
| EP | 0 915 174 | 5/1999 |
| WO | WO 90/06042 | 6/1990 |
| WO | WO 94/21820 | 9/1994 |
| WO | WO 96/31622 | 10/1996 |
| WO | WO 97/46711 | 12/1997 |
| WO | WO 98/14610 | 4/1998 |

OTHER PUBLICATIONS

Cobianchi and Wilson, "Enzymes for modifying and labeling DNA and RNA," *Methods in Enzymology*, 152:94-110, 1987.
Dong et al., "Flexible use of high-density oligonucleotide arrays for single-nucleotide polymorphism discovery and validation," *Genome Research*, 11(8):1418-1424, 2001.
European Search Report for Application No. 01 981 538, dated Jan. 25, 2005.
Examiner's First Report for Australian Application No. 2002213175, dated Mar. 17, 2006.
Examiner's First Report in Australian Application No. 2001271254, dated Oct. 17, 2005.
Examiner's Report issued in Canadian Application No. 2,425,747, dated Dec. 21, 2009.
Examiner's Second Report for Australian Application No. 2002213175, dated May 17, 2007.
First Office Action for Chinese Application No. 01812665, dated Oct. 14, 2005.
First Office Action for Chinese Application No. 01820515, dated Mar. 24, 2006.
Guatelli et al., "Isothermal, in vitro amplification of nucleic acids by a multienzyme reaction modeled after retroviral replication," *Proc. Nat'l. Acad. Sci.*, 87:1874-1878, 1990.
Hacia et al., "Detection of heterozygous mutations in BRCA1 using high density oligonucleotide arrays and two-colour fluroscene analysis," *Nature Genetics*, 14:441-447, 1996.
Hosfield et al., "Newly discovered archaebacterial flap endonucleases show a structure-specific mechanism for DNA substrate binding and catalysis resembling human flap endonuclease-1," *J. Biol. Chem.*, 273(42):27154-17164, 1998.
International Search Report for PCT/US2001/16359, dated Mar. 19, 2003.
International Search Report for PCT/US2001/31993, dated Jul. 8, 2003.
Jain, "Applications of biochip and microarray systems in pharmacogenomics," *Pharmacogenomics*, 1(3):289-307, 2000.
Jurczyk et al., "Synthesis of 2'-deoxyisoguanosine 5'-triphosphate and 2'-deoxy-5-methylisocytosine 5'-triphosphate," *Helvetica Chimca Acta*, 82:1005-1015, 1999.
Kälin et al., "Evaluation of the ligase chain reaction (LCR) for the detection of point mutations," *Mutat. Res.*, 283(2):119-123, 1992.
La Rocco et al., "Evaluation of a commercial rRNA amplification assay for direct detection of Mycobacterium tuberculosis in processed sputum," *Eur. J. Clin. Microbiol. Infect. Dis.*, 13(9):726-731, 1994.
Livak et al., "Oligonucleotides with fluorescent dyes at opposite ends provide a quenched probe system useful for detecting PCR product and nucleic acid hybridization," *PCR Methods and Applications*, 4(6):357-362, 1995.
Lizardi et al., "Mutation detection and single-molecule counting using isothermal rolling-circle amplification," *Nat. Genet.*, 19(3):225-232, 1998.
McMinn et al., "Efforts toward expansion of the genetic alphabet: DNA polymerase recognition of a highly stable, self-pairing hydrophobic base," *J. Am. Chem. Soc.*, 121(49):11585-6, 1999.
Narang et al., "Improved phosphotriester method for the synthesis of gene fragments," *Methods in Enzymology*, 68:90-98, 1979.
Newton et al., "The production of PCR products with 5' single-stranded tails using primers that incorporate novel phosphoramidite intermediates," *Nucleic Acids Research*, 21(5):1155-1162, 1993.
Nolan et al., "SNP scoring for drug discovery applications," In: Integrated Technologies for Drug Discovery, Houng-Ya Mei and Anthony W. Czamik, Eds., New York: Marcel Dekker, Inc., Chapter 6, pp. 145-161, 2002.
Notice of Acceptance for Australian Application No. 2001271254, dated Apr. 23, 2007.
Notice of Reasons for Rejection for Japanese Application No. 2002-536094, dated Sep. 21, 2007.
Office Action for EP Application No. 01 950 231.9, dated May 16, 2007.
Office Action for EP Application No. 01 981 538, dated Feb. 1, 2005.
Office Action for EP Application No. 01 981 538, dated Nov. 21, 2005.
Office Action for EP Application No. 01 981 538, dated Sep. 9, 2004.
Office Action for EP Application No. 01 981 538, dated Sep. 25, 2006.
Office Communication issued in Chinese Patent Application No. 01812665.0, dated Sep. 12, 2008. (English translation).
Office Communication issued in European Patent Application No. 01 950 231.9, dated Jul. 30, 2009.
Office Communication issued in Japanese Patent Application No. 2002-536094, dated Mar. 16, 2009. (English translation).
Office Communication issued in Japanese Patent Application No. 2001-586611, dated Apr. 11, 2012. (English translation).
Office Communication issued in Japanese Patent Application No. 2001-586611, dated Feb. 23, 2011. (English translation).
Office Communication issued in U.S. Appl. No. 11/490,319, dated Dec. 8, 2010.
Office Communication issued in U.S. Appl. No. 11/490,319, dated Jun. 14, 2010.
Office Communication issued in U.S. Appl. No. 11/490,319, dated Feb. 2, 2010.
Office Communication issued in U.S. Appl. No. 11/490,319, dated May 28, 2009.
Office Communication issued in U.S. Appl. No. 11/490,319, dated Jan. 28, 2009.
Office Communication issued in U.S. Appl. No. 11/284,307, dated Aug. 10, 2010.
Office Communication issued in U.S. Appl. No. 11/284,307, dated Dec. 16, 2009.
Office Communication issued in U.S. Appl. No. 11/284,307, dated Nov. 17, 2008.
Office Communication issued in U.S. Appl. No. 11/284,307, dated Apr. 30, 2008.
Office Communication issued in U.S. Appl. No. 11/284,307, dated Jan. 11, 2008.
Office Communication issued in U.S. Appl. No. 09/977,615, dated Jun. 1, 2004.
Office Communication issued in U.S. Appl. No. 09/977,615, dated Jul. 31, 2003.
Office Communication issued in U.S. Appl. No. 09/861,292, dated May 21, 2003.
Office Communication issued in U.S. Appl. No. 09/861,292, dated Sep. 12, 2002.
Office Communication issued in U.S. Appl. No. 09/861,292, dated Jun. 17, 2008.
Office Communication issued in U.S. Appl. No. 09/861,292, dated Jun. 19, 2007.

Office Communication issued in U.S. Appl. No. 09/861,292, dated Sep. 5, 2006.
Office Communication issued in U.S. Appl. No. 09/861,292, dated Jul. 12, 2006.
Office Communication issued in U.S. Appl. No. 09/861,292, dated Feb. 22, 2006.
Office Communication issued in U.S. Appl. No. 09/861,292, dated Sep. 7, 2005.
Office Communication issued in U.S. Appl. No. 09/861,292, dated Mar. 14, 2005.
Office Communication issued in U.S. Appl. No. 09/861,292, dated Dec. 3, 2004.
Office Communication issued in U.S. Appl. No. 09/861,292, dated Mar. 23, 2004.
Ogawa et al., "Efforts toward the expansion of the genetic alphabet: Information storage and replication with unnatural hydrophobic base pairs," *J. Am. Chem. Soc.*, 122:3274-3287, 2000.
PCT International Preliminary Examination Report issued in International application No. PCT/US01/31993, dated Sep. 10, 2004.
Petersheim and Turner, "Base-stacking and base-pairing contributions to helix stability: thermodynamics of double-helix formation with CCGG, CCGGp, CCGGAp, ACCGGp, CCGGUp, and ACCG-GUp," *Biochemistry*, 22(2):256-263, 1983.
Peyret et al., "Nearest-Neighbor Thermodynamics and NMR of DNA Sequences with Internal A•A, C•C, G•G, and T•T Mismatches," *Biochemistry*, 38(12):3468-3477, 1999.
Ren et al., "Naphthalene, Phenanthrene, and Pyrene as DNA Base Analogues: Synthesis, Structure, and Fluorescence in DNA," *J. Am. Chem. Soc.*, 118(33):7671-7678, 1996.
Roberts et al., "Theoretical and experimental study of isoguanine and isocytosine: base pairing in an expanded genetic system," *J. Am. Chem. Soc.*, 119(20):4640-4649, 1997.
SantaLucia et al., "Improved Nearest-Neighbor Parameters for Predicting DNA Duplex Stability," *Biochemistry*, 35(11):3555-3562, 1996.
Second Office Action for Chinese Application No. 01812665, dated Oct. 20, 2006.
Sherrill et al., "Nucleic Acid Analysis Using an Expanded Genetic Alphabet to Quench Fluorescence,"*J. Am. Chem. Soc.*, 126(14):4550-4556, 2004.
Switzer et al., "Enzymatic recognition of the base pair between isocytidine and isoguanosine," *Biochemistry*, 32(39):10489-10496, 1993.
Taylor et al., "Flow Cytometric Platform for High-Throughput Single Nucleotide Polymorphism Analysis," *BioTechniques*, 30(3):661-669, 2001.
The Stratagene Catalog, p. 39, 1988.
Tor et al., "Site specific enzymatic incorporation of an unnatural base, N6-(6-Aminohexyl)isoguanosine, into RNA," *J. Am. Chem. Soc.*, 115:4461-4467, 1993.
Ugozzoli et al., "Detection of specific alleles by using allele-specific primer extension followed by capture on solid support," *GATA*, 9(4):107-112, 1992.
Walker et al., "Isothermal in vitro amplification of DNA by a restriction enzyme/DNA polymerase system," *Proc. Nat'l. Acad Sci. USA*, 89(1):392-396, 1992.
Whitcombe et al., "Detection of PCR products using self-probing amplicons and fluorescence," *Nature Biotech*, 17(8):804-807, 1999.

* cited by examiner

A is the point of attachment to a polymeric backbone
X is N or C-Z
Y is N or C-H
Z is H or a substituted or unsubstituted alkyl group

SEQUENCE LISTING

```
<160> NUMBER OF SEQ ID NOS: 165

<210> SEQ ID NO 1
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 1 gangtntgtc                                                          10

<210> SEQ ID NO 2
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 2 cngttnttcc                                                          10
```

```
<210> SEQ ID NO 3
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 3 ggnttgntag                                                                  10

<210> SEQ ID NO 4
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 4 cttngntctc                                                                  10

<210> SEQ ID NO 5
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 5 cntcangaac                                                                  10

<210> SEQ ID NO 6
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 6 gtagntangc                                                                  10
```

```
<210> SEQ ID NO 7
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 7 ggangntaac                                                          10

<210> SEQ ID NO 8
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 8 cngtatngtg                                                          10

<210> SEQ ID NO 9
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 9 catnggtang                                                          10

<210> SEQ ID NO 10
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 10 gattntcgnc                                                          10
```

```
<210> SEQ ID NO 11
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 11 gttnangacc                                                              10

<210> SEQ ID NO 12
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 12 cngaangatc                                                              10

<210> SEQ ID NO 13
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 13 caantacgnc                                                              10

<210> SEQ ID NO 14
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 14 cggnatanac                                                              10
```

```
<210> SEQ ID NO 15
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 15 gnaaanngg                                                              10

<210> SEQ ID NO 16
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 16 gtcntagnnc                                                             10

<210> SEQ ID NO 17
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 17 gncctntanc                                                             10

<210> SEQ ID NO 18
<211> LENGTH: 10
<212> TYPE: DNA
<213> ORGANISM: Artificial
<220> FEATURE:
<223> OTHER INFORMATION: synthetic oligonucleotide
```

```
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 18 ccnacntgag                                                                 10

<210> SEQ ID NO 19
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 19 ctnncanagg                                                                 10

<210> SEQ ID NO 20
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 20 gtnganatgc                                                                 10

<210> SEQ ID NO 21
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 21 gaaantgnng                                                                 10
```

```
<210> SEQ ID NO 22
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 22 gctgnanatc                                                              10

<210> SEQ ID NO 23
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 23 cgcanatnac                                                              10

<210> SEQ ID NO 24
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 24 ctggntcnag                                                              10

<210> SEQ ID NO 25
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine
```

```
<400> SEQUENCE: 25 ggaananncc                                                              10

<210> SEQ ID NO 26
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 26 cntcgcntac                                                              10

<210> SEQ ID NO 27
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 27 gncnaaaang                                                              10

<210> SEQ ID NO 28
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 28 cnngacnatc                                                              10

<210> SEQ ID NO 29
<211> LENGTH: 10
<212> TYPE: DNA
<213> ORGANISM: Artificial
<220> FEATURE:
<223> OTHER INFORMATION: synthetic oligonucleotide
```

```
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 29 ccatnagncc                                                          10

<210> SEQ ID NO 30
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 30 ggcantntgg                                                          10

<210> SEQ ID NO 31
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 31 ctnaacnggg                                                          10

<210> SEQ ID NO 32
<211> LENGTH: 9
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 32 gganacgng                                                            9

<210> SEQ ID NO 33
<211> LENGTH: 10
<212> TYPE: DNA
<213> ORGANISM: Artificial
<220> FEATURE:
<223> OTHER INFORMATION: synthetic oligonucleotide
```

```
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 33 gcgntttang                                                            10

<210> SEQ ID NO 34
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 34 gagnagntnc                                                            10

<210> SEQ ID NO 35
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 35 gnctaanccg                                                            10

<210> SEQ ID NO 36
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 36 gcntgtncac                                                            10

<210> SEQ ID NO 37
<211> LENGTH: 10
```

```
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 37 gncagantcg                                                          10

<210> SEQ ID NO 38
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 38 cgtnctagng                                                          10

<210> SEQ ID NO 39
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 39 cgnntagtng                                                          10

<210> SEQ ID NO 40
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 40 cnaggnaacc                                                          10
```

<210> SEQ ID NO 41
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 41 cnagangang                                                          10

<210> SEQ ID NO 42
<211> LENGTH: 9
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 42 cgntgngtc                                                            9

<210> SEQ ID NO 43
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 43 cagncgtnag                                                          10

<210> SEQ ID NO 44
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<220> FEATURE:

<400> SEQUENCE: 44 ggctntgnac                                                                 10

<210> SEQ ID NO 45
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 45 ccagngnaag                                                                 10

<210> SEQ ID NO 46
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represent iso-cytosine
<220> FEATURE:
<221> NAME/KEY: modified_base
<222> LOCATION: (8)..(8)
<223> OTHER INFORMATION: n represent iso-cytosine

<400> SEQUENCE: 46 ggcnaatngc                                                                 10

<210> SEQ ID NO 47
<211> LENGTH: 9
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 47 gnctgcngg                                                                  9

<210> SEQ ID NO 48
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (6)..(6)

-continued

<223> OTHER INFORMATION: n represents iso-cytosine

<400> SEQUENCE: 48 ganctncggc                                                                                          10

<210> SEQ ID NO 49
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 49 gtncganggg                                                                                          10

<210> SEQ ID NO 50
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 50 ggnnatccng                                                                                          10

<210> SEQ ID NO 51
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 51 gncttcnatg                                                                                          10

<210> SEQ ID NO 52
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)

```
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 52 cntcttnncc                                                              10

<210> SEQ ID NO 53
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 53 ctctnanccc                                                              10

<210> SEQ ID NO 54
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 54 ctcntggtnc                                                              10

<210> SEQ ID NO 55
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 55 gncaaancac                                                              10

<210> SEQ ID NO 56
<211> LENGTH: 10
<212> TYPE: DNA
<213> ORGANISM: Artificial
<220> FEATURE:
```

```
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 56 gttngcnttg                                                           10

<210> SEQ ID NO 57
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 57 cncntncaac                                                           10

<210> SEQ ID NO 58
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 58 ctnnacannc                                                           10

<210> SEQ ID NO 59
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (7)..(7)
```

<223> OTHER INFORMATION: n represents iso-cytosine

<400> SEQUENCE: 59 cnactcnacc                                                                 10

<210> SEQ ID NO 60
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 60 gacncanntg                                                                 10

<210> SEQ ID NO 61
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 61 ctcnctnacg                                                                 10

<210> SEQ ID NO 62
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 62 gtggnctntc                                                                 10

<210> SEQ ID NO 63
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)

```
<223> OTHER INFORMATION: n represents iso-cytosine
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 63 cannaccnag                                                            10

<210> SEQ ID NO 64
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 64 gtncnanacc                                                            10

<210> SEQ ID NO 65
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 65 cacnntgntc                                                            10

<210> SEQ ID NO 66
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 66
```
gntcctngtc                                                            10

<210> SEQ ID NO 67
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 67 ccnnatgtng                                                            10

<210> SEQ ID NO 68
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 68 gnggtttnntc                                                           10

<210> SEQ ID NO 69
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 69 cnccgnaatc                                                            10

<210> SEQ ID NO 70
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)

```
<223> OTHER INFORMATION: n represents iso-cytosine
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 70 gnnacnacac                                                                 10

<210> SEQ ID NO 71
<211> LENGTH: 9
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 71 gcncngtnc                                                                   9

<210> SEQ ID NO 72
<211> LENGTH: 9
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 72 gncngganc                                                                   9

<210> SEQ ID NO 73
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 73
```
cganagcanc                                                              10

<210> SEQ ID NO 74
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 74 cccantccnc                                                              10

<210> SEQ ID NO 75
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 75 gtnccnncag                                                              10

<210> SEQ ID NO 76
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 76 cncctancgg                                                              10

<210> SEQ ID NO 77
<211> LENGTH: 9
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (7)..(7)

<223> OTHER INFORMATION: n represents iso-cytosine

<400> SEQUENCE: 77 gngttgncg                                                                                         9

<210> SEQ ID NO 78
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 78 cnaagnancg                                                                                        10

<210> SEQ ID NO 79
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 79 ggagncnntc                                                                                        10

<210> SEQ ID NO 80
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 80 cngnangtac                                                                                        10

<210> SEQ ID NO 81

```
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 81 gnacgantng                                                          10

<210> SEQ ID NO 82
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 82 gngctncatg                                                          10

<210> SEQ ID NO 83
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 83 gtgnagagng                                                          10

<210> SEQ ID NO 84
<211> LENGTH: 9
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 84
``` gccgncntc  9

<210> SEQ ID NO 85
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 85 caancgntcg  10

<210> SEQ ID NO 86
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 86 cacanacngc  10

<210> SEQ ID NO 87
<211> LENGTH: 9
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 87 gntggnncg  9

<210> SEQ ID NO 88
<211> LENGTH: 9
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (7)..(7)

<223> OTHER INFORMATION: n represents iso-cytosine

<400> SEQUENCE: 88 gccnccngt                                                                                    9

<210> SEQ ID NO 89
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 89 cnanggtcnc                                                                                  10

<210> SEQ ID NO 90
<211> LENGTH: 9
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 90 ccnngngtg                                                                                    9

<210> SEQ ID NO 91
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 91 ggnacnccag                                                                                  10

<210> SEQ ID NO 92
<211> LENGTH: 10
<212> TYPE: DNA
<213> ORGANISM: Artificial
<220> FEATURE:

```
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine

<400> SEQUENCE: 92 gcctncngac                                                              10

<210> SEQ ID NO 93
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 93 cnttncgcnc                                                              10

<210> SEQ ID NO 94
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine
<220> FEATURE:
<221> NAME/KEY: modified_base
<222> LOCATION: (9)..(9)
<223> OTHER INFORMATION: n represents iso-cytosine

<400> SEQUENCE: 94 cnctangnng                                                              10

<210> SEQ ID NO 95
<211> LENGTH: 9
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (5)..(5)
```

```
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 95 cngcnagng                                                                9

<210> SEQ ID NO 96
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (6)..(6)
<223> OTHER INFORMATION: n represents iso-cytosine

<400> SEQUENCE: 96 cnagcnacgg                                                              10

<210> SEQ ID NO 97
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 97 gacangcncc                                                              10

<210> SEQ ID NO 98
<211> LENGTH: 9
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-cytosine
<220> FEATURE:
<221> NAME/KEY: modified_base
<222> LOCATION: (7)..(7)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine

<400> SEQUENCE: 98 gggncgnna                                                                9

<210> SEQ ID NO 99
<211> LENGTH: 10
<212> TYPE: DNA
<213> ORGANISM: Artificial
<220> FEATURE:
```

```
<223> OTHER INFORMATION: synthetic oligonucleotide

<400> SEQUENCE: 99
gccagtttaa                                                              10

<210> SEQ ID NO 100
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-cytosine

<400> SEQUENCE: 100 gccantttaa                                                              10

<210> SEQ ID NO 101
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-cytosine

<400> SEQUENCE: 101 gcnagtttaa                                                              10

<210> SEQ ID NO 102
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-guanine

<400> SEQUENCE: 102 gncagtttaa                                                              10

<210> SEQ ID NO 103
<211> LENGTH: 10
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-guanine
<220> FEATURE:
<221> NAME/KEY: modified_base
<222> LOCATION: (3)..(3)
<223> OTHER INFORMATION: n represents iso-guanine

<400> SEQUENCE: 103 gnnagtttaa                                                              10

<210> SEQ ID NO 104
<211> LENGTH: 154
<212> TYPE: DNA
<213> ORGANISM: Mus musculus
<300> PUBLICATION INFORMATION:
```

<308> DATABASE ACCESSION NUMBER: NT_039491.1
<309> DATABASE ENTRY DATE: 2003-02-25
<313> RELEVANT RESIDUES IN SEQ ID NO: (1729106)..(1729259)

<400> SEQUENCE: 104
agaaacaacc atctaatccc acactaaaat tcaaggctcc acagacgaaa cagtgaagaa    60
taattgttca gcatactaac caactgatta catatttacc atactcaggt ttgtgcttca   120
tacaaaccca yagtccggcg ctccctgtta gatg                               154

<210> SEQ ID NO 105
<211> LENGTH: 61
<212> TYPE: DNA
<213> ORGANISM: Mus musculus
<300> PUBLICATION INFORMATION:
<308> DATABASE ACCESSION NUMBER: NT_039209.1
<309> DATABASE ENTRY DATE: 2003-02-25
<313> RELEVANT RESIDUES IN SEQ ID NO: (27172470)..(27172530)

<400> SEQUENCE: 105
cttctcccat tgcccagggc actctcctct gtagartaga ctgatytttg tggagacatc    60
a                                                                    61

<210> SEQ ID NO 106
<211> LENGTH: 67
<212> TYPE: DNA
<213> ORGANISM: Mus musculus
<300> PUBLICATION INFORMATION:
<308> DATABASE ACCESSION NUMBER: NT_039473.1
<309> DATABASE ENTRY DATE: 2003-02-25
<313> RELEVANT RESIDUES IN SEQ ID NO: (532094)..(532160)

<400> SEQUENCE: 106
agtgcctgct acctgtcagg tgaaaatttc ttagtgatcc yaagctcaat gggtgcyggc    60
ttgcagg                                                              67

<210> SEQ ID NO 107
<211> LENGTH: 72
<212> TYPE: DNA
<213> ORGANISM: Mus musculus
<300> PUBLICATION INFORMATION:
<308> DATABASE ACCESSION NUMBER: NT_039674.1
<309> DATABASE ENTRY DATE: 2003-02-25
<313> RELEVANT RESIDUES IN SEQ ID NO: (46479067)..(46479138)

<400> SEQUENCE: 107
ggttggaatg tttgcacatg cagtgttagt tatttgggyg ataactactt agcttatcta    60
gcctggtcca gc                                                        72

<210> SEQ ID NO 108
<211> LENGTH: 80
<212> TYPE: DNA
<213> ORGANISM: Mus musculus
<300> PUBLICATION INFORMATION:
<308> DATABASE ACCESSION NUMBER: NT_039662.1
<309> DATABASE ENTRY DATE: 2003-02-25
<313> RELEVANT RESIDUES IN SEQ ID NO: (658679)..(658758)

<400> SEQUENCE: 108
ctgatctgac ctcagactgt tgtgctaaca gatataacac cagtaagttg astcaaatac    60
tgcaggaagt agagccttgc                                                80

<210> SEQ ID NO 109
<211> LENGTH: 89
<212> TYPE: DNA

```
<213> ORGANISM: Mus musculus
<300> PUBLICATION INFORMATION:
<308> DATABASE ACCESSION NUMBER: NT_039212.1
<309> DATABASE ENTRY DATE: 2003-02-25
<313> RELEVANT RESIDUES IN SEQ ID NO: (3887249)..(3887337)

<400> SEQUENCE: 109
gactgctgga gagctgaggg aggctgtgga gaataaggag agagcrtagt ctcgtgccct      60
gccctgccca tactgagcag ccaagacac                                       89

<210> SEQ ID NO 110
<211> LENGTH: 96
<212> TYPE: DNA
<213> ORGANISM: Mus musculus
<300> PUBLICATION INFORMATION:
<308> DATABASE ACCESSION NUMBER: NT_039586.1
<309> DATABASE ENTRY DATE: 2003-02-25
<313> RELEVANT RESIDUES IN SEQ ID NO: (6594595)..(6594690)

<400> SEQUENCE: 110
ggactgtcca aakggatctc aaggagaata gtccttgcta ttargagtat aaaggcataa      60
aagaggtcat aggggacaac catgaccaag aagttg                               96

<210> SEQ ID NO 111
<211> LENGTH: 107
<212> TYPE: DNA
<213> ORGANISM: Mus musculus
<300> PUBLICATION INFORMATION:
<308> DATABASE ACCESSION NUMBER: NT_039551.1
<309> DATABASE ENTRY DATE: 2003-02-25
<313> RELEVANT RESIDUES IN SEQ ID NO: (15414183)..(15414289)

<400> SEQUENCE: 111
ccttcctgca ytccacagta taaacacaga atgcacactg crgtcgttgt atttgtgttc      60
gatgtgaatt aaagatgctt tggctaagcc aggagatgat aatactg                   107

<210> SEQ ID NO 112
<211> LENGTH: 129
<212> TYPE: DNA
<213> ORGANISM: Mus musculus
<300> PUBLICATION INFORMATION:
<308> DATABASE ACCESSION NUMBER: NT_039209.1
<309> DATABASE ENTRY DATE: 2003-02-25
<313> RELEVANT RESIDUES IN SEQ ID NO: (26992396)..(26992524)

<400> SEQUENCE: 112
cacatacacc atgtcagcca tcagcgcaaa gccttcgagt ttcagctgtg agatgaaggc      60
ttggagaagc acgttgatct gcaaagaagc aaaggagcta gcggaggcyg gtcactgacc     120
gactgctca                                                             129

<210> SEQ ID NO 113
<211> LENGTH: 18
<212> TYPE: DNA
<213> ORGANISM: Artificial
<220> FEATURE:
<223> OTHER INFORMATION: synthetic oligonucleotide

<400> SEQUENCE: 113
catctaacag ggagcgcc                                                   18

<210> SEQ ID NO 114
<211> LENGTH: 24
<212> TYPE: DNA
<213> ORGANISM: Artificial
<220> FEATURE:
```

```
<223> OTHER INFORMATION: synthetic oligonucleotide
<220> FEATURE:
<221> NAME/KEY: modified_base
<222> LOCATION: (1)..(1)
<223> OTHER INFORMATION: n represents deoxythymidylate labeled with 6-
      carboxyfluorescein (6-FAM)

<400> SEQUENCE: 114
nagaaacaac catctaatcc caca                                              24

<210> SEQ ID NO 115
<211> LENGTH: 19
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: n represents deoxythymidylate labeled with 6-
      carboxyfluorescein (6-FAM)

<400> SEQUENCE: 115
ncttctccca ttgcccagg                                                    19

<210> SEQ ID NO 116
<211> LENGTH: 23
<212> TYPE: DNA
<213> ORGANISM: Artificial
<220> FEATURE:
<223> OTHER INFORMATION: synthetic oligonucleotide

<400> SEQUENCE: 116
tgatgtctcc acaaagatca gtc                                               23

<210> SEQ ID NO 117
<211> LENGTH: 19
<212> TYPE: DNA
<213> ORGANISM: Artificial
<220> FEATURE:
<223> OTHER INFORMATION: synthetic oligonucleotide

<400> SEQUENCE: 117
agtgcctgct acctgtcag                                                    19

<210> SEQ ID NO 118
<211> LENGTH: 17
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: n represents deoxythymidylate labeled with 6-
      carboxyfluorescein (6-FAM)

<400> SEQUENCE: 118
ncctgcaagc cagcacc                                                      17

<210> SEQ ID NO 119
<211> LENGTH: 22
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: n represents deoxythymidylate labeled with 6-
```

-continued carboxyfluorescein (6-FAM)

<400> SEQUENCE: 119
nggttggaat gtttgcacat gc                                            22

<210> SEQ ID NO 120
<211> LENGTH: 21
<212> TYPE: DNA
<213> ORGANISM: Artificial
<220> FEATURE:
<223> OTHER INFORMATION: synthetic oligonucleotide

<400> SEQUENCE: 120
gctggaccag gctagataag c                                             21

<210> SEQ ID NO 121
<211> LENGTH: 23
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: n represents deoxythymidylate labeled with 6-
      carboxyfluorescein (6-FAM)

<400> SEQUENCE: 121
nctgatctga cctcagactg ttg                                           23

<210> SEQ ID NO 122
<211> LENGTH: 19
<212> TYPE: DNA
<213> ORGANISM: Artificial
<220> FEATURE:
<223> OTHER INFORMATION: synthetic oligonucleotide

<400> SEQUENCE: 122
gcaaggctct acttcctgc                                                19

<210> SEQ ID NO 123
<211> LENGTH: 20
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: n represents deoxythymidylate labeled with 6-
      carboxyfluorescein (6-FAM)

<400> SEQUENCE: 123
ngactgctgg agagctgagg                                               20

<210> SEQ ID NO 124
<211> LENGTH: 21
<212> TYPE: DNA
<213> ORGANISM: Artificial
<220> FEATURE:
<223> OTHER INFORMATION: synthetic oligonucleotide

<400> SEQUENCE: 124
gtgtcttggc tgctcagtat g                                             21

<210> SEQ ID NO 125
<211> LENGTH: 21
<212> TYPE: DNA

```
<213> ORGANISM: Artificial
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: n represents deoxythymidylate labeled with 6-
      carboxyfluorescein (6-FAM)

<400> SEQUENCE: 125
nggactgtcc aaagggatct c                                              21

<210> SEQ ID NO 126
<211> LENGTH: 22
<212> TYPE: DNA
<213> ORGANISM: Artificial
<220> FEATURE:
<223> OTHER INFORMATION: synthetic oligonucleotide

<400> SEQUENCE: 126
caacttcttg gtcatggttg tc                                             22

<210> SEQ ID NO 127
<211> LENGTH: 19
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: n represents indodicarbocyanine
      3-1-O-(2-cyanoethyl)-(N,N-diisopropyl)-phosphoramidite (Cy3)

<400> SEQUENCE: 127
nccttcctgc aytccacag                                                 19

<210> SEQ ID NO 128
<211> LENGTH: 26
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: n represents deoxythymidylate labeled with 6-
      carboxyfluorescein (6-FAM)

<400> SEQUENCE: 128
ncagtattat catctcctgg cttagc                                         26

<210> SEQ ID NO 129
<211> LENGTH: 20
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (1)..(1)
<223> OTHER INFORMATION: n represents deoxythymidylate labeled with 6-
      carboxyfluorescein (6-FAM)

<400> SEQUENCE: 129
ncacatacac catgtcagcc                                                20

<210> SEQ ID NO 130
<211> LENGTH: 17
<212> TYPE: DNA
```

```
<213> ORGANISM: Artificial
<220> FEATURE:
<223> OTHER INFORMATION: synthetic oligonucleotide

<400> SEQUENCE: 130
tgagcagtcg gtcagtg                                                  17

<210> SEQ ID NO 131
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-guanine
<220> FEATURE:
<221> NAME/KEY: modified_base
<222> LOCATION: (8)..(8)
<223> OTHER INFORMATION: n represents iso-guanine
<220> FEATURE:
<221> NAME/KEY: misc_feature
<222> LOCATION: (10)..(11)
<223> OTHER INFORMATION: an n-propylene spacer (c3) between these
      locations

<400> SEQUENCE: 131
gtgnacangc gcttcataca aacccac                                       27

<210> SEQ ID NO 132
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-guanine
<220> FEATURE:
<221> NAME/KEY: modified_base
<222> LOCATION: (9)..(9)
<223> OTHER INFORMATION: n represents iso-guanine
<220> FEATURE:
<221> NAME/KEY: misc_feature
<222> LOCATION: (10)..(11)
<223> OTHER INFORMATION: an n-propylene spacer (c3) between these
      locations

<400> SEQUENCE: 132
cgantctgnc gcttcataca aacccat                                       27

<210> SEQ ID NO 133
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-guanine
<220> FEATURE:
<221> NAME/KEY: modified_base
<222> LOCATION: (8)..(8)
<223> OTHER INFORMATION: n represents iso-guanine
<220> FEATURE:
<221> NAME/KEY: misc_feature
<222> LOCATION: (10)..(11)
<223> OTHER INFORMATION: an n-propylene spacer (c3) between these
      locations

<400> SEQUENCE: 133
```
ctancaancc cactctcctc tgtagaa                                              27

<210> SEQ ID NO 134
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-guanine
<220> FEATURE:
<221> NAME/KEY: modified_base
<222> LOCATION: (7)..(7)
<223> OTHER INFORMATION: n represents iso-guanine
<220> FEATURE:
<221> NAME/KEY: misc_feature
<222> LOCATION: (10)..(11)
<223> OTHER INFORMATION: an n-propylene spacer (c3) between these
      locations

<400> SEQUENCE: 134
gagancnaag cactctcctc tgtagag                                              27

<210> SEQ ID NO 135
<211> LENGTH: 30
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-guanine
<220> FEATURE:
<221> NAME/KEY: modified_base
<222> LOCATION: (9)..(9)
<223> OTHER INFORMATION: n represents iso-guanine
<220> FEATURE:
<221> NAME/KEY: misc_feature
<222> LOCATION: (10)..(11)
<223> OTHER INFORMATION: an n-propylene spacer (c3) between these
      locations

<400> SEQUENCE: 135
gttcntgang gaaaatttct tagtgatcct                                           30

<210> SEQ ID NO 136
<211> LENGTH: 29
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-guanine
<220> FEATURE:
<221> NAME/KEY: modified_base
<222> LOCATION: (6)..(6)
<223> OTHER INFORMATION: n represents iso-guanine
<220> FEATURE:
<221> NAME/KEY: misc_feature
<222> LOCATION: (10)..(11)
<223> OTHER INFORMATION: an n-propylene spacer (c3) between these
      locations

<400> SEQUENCE: 136
gcntanctac aaaatttctt agtgatccc                                            29

<210> SEQ ID NO 137

```
<211> LENGTH: 28
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-guanine
<220> FEATURE:
<221> NAME/KEY: modified_base
<222> LOCATION: (7)..(7)
<223> OTHER INFORMATION: n represents iso-guanine
<220> FEATURE:
<221> NAME/KEY: misc_feature
<222> LOCATION: (10)..(11)
<223> OTHER INFORMATION: an  n-propylene spacer (c3) between these
      locations

<400> SEQUENCE: 137
gttancntcc agtgttagtt atttgggt                                             28

<210> SEQ ID NO 138
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-guanine
<220> FEATURE:
<221> NAME/KEY: modified_base
<222> LOCATION: (9)..(9)
<223> OTHER INFORMATION: n represents iso-guanine
<220> FEATURE:
<221> NAME/KEY: misc_feature
<222> LOCATION: (10)..(11)
<223> OTHER INFORMATION: an  n-propylene spacer (c3) between these
      locations

<400> SEQUENCE: 138
cacnatacng gtgttagtta tttgggc                                              27

<210> SEQ ID NO 139
<211> LENGTH: 28
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-guanine
<220> FEATURE:
<221> NAME/KEY: modified_base
<222> LOCATION: (7)..(7)
<223> OTHER INFORMATION: n represents iso-guanine
<220> FEATURE:
<221> NAME/KEY: misc_feature
<222> LOCATION: (10)..(11)
<223> OTHER INFORMATION: an  n-propylene spacer (c3) between these
      locations

<400> SEQUENCE: 139
cntaccnatg taacaccagt aagttgac                                             28

<210> SEQ ID NO 140
<211> LENGTH: 28
<212> TYPE: DNA
<213> ORGANISM: Artificial
<220> FEATURE:
<223> OTHER INFORMATION: synthetic oligonucleotide
```

```
<220> FEATURE:
<221> NAME/KEY: modified_base
<222> LOCATION: (2)..(2)
<223> OTHER INFORMATION: n represents iso-guanine
<220> FEATURE:
<221> NAME/KEY: modified_base
<222> LOCATION: (6)..(6)
<223> OTHER INFORMATION: n represents iso-guanine
<220> FEATURE:
<221> NAME/KEY: misc_feature
<222> LOCATION: (10)..(11)
<223> OTHER INFORMATION: an  n-propylene spacer (c3) between these
      locations

<400> SEQUENCE: 140
gncganaatc taacaccagt aagttgag                                           28

<210> SEQ ID NO 141
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-guanine
<220> FEATURE:
<221> NAME/KEY: modified_base
<222> LOCATION: (7)..(7)
<223> OTHER INFORMATION: n represents iso-guanine
<220> FEATURE:
<221> NAME/KEY: misc_feature
<222> LOCATION: (10)..(11)
<223> OTHER INFORMATION: an  n-propylene spacer (c3) between these
      locations

<400> SEQUENCE: 141
gncgtanttg agaataagga gagagca                                            27

<210> SEQ ID NO 142
<211> LENGTH: 26
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-guanine
<220> FEATURE:
<221> NAME/KEY: modified_base
<222> LOCATION: (7)..(7)
<223> OTHER INFORMATION: n represents iso-guanine
<220> FEATURE:
<221> NAME/KEY: misc_feature
<222> LOCATION: (10)..(11)
<223> OTHER INFORMATION: an  n-propylene spacer (c3) between these
      locations

<400> SEQUENCE: 142
gtntatnccg gaataaggag agagcg                                             26

<210> SEQ ID NO 143
<211> LENGTH: 30
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-guanine
<220> FEATURE:
```

```
<221> NAME/KEY: modified_base
<222> LOCATION: (8)..(8)
<223> OTHER INFORMATION: n represents iso-guanine
<220> FEATURE:
<221> NAME/KEY: misc_feature
<222> LOCATION: (10)..(11)
<223> OTHER INFORMATION: an  n-propylene spacer (c3) between these
      locations

<400> SEQUENCE: 143
gacanacntc  agaatagtcc ttgctatta a                                      30

<210> SEQ ID NO 144
<211> LENGTH: 30
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-guanine
<220> FEATURE:
<221> NAME/KEY: modified_base
<222> LOCATION: (9)..(9)
<223> OTHER INFORMATION: n represents iso-guanine
<220> FEATURE:
<221> NAME/KEY: misc_feature
<222> LOCATION: (11)..(11)
<223> OTHER INFORMATION: an  n-propylene spacer (c3) between these
      locations

<400> SEQUENCE: 144
ggaanaacng agaatagtcc ttgctatta g                                       30

<210> SEQ ID NO 145
<211> LENGTH: 25
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-guanine
<220> FEATURE:
<221> NAME/KEY: modified_base
<222> LOCATION: (6)..(6)
<223> OTHER INFORMATION: n represents iso-guanine
<220> FEATURE:
<221> NAME/KEY: misc_feature
<222> LOCATION: (10)..(11)
<223> OTHER INFORMATION: an  n-propylene spacer (c3) between these
      locations

<400> SEQUENCE: 145
gatntncagc agaatgcaca ctgca                                             25

<210> SEQ ID NO 146
<211> LENGTH: 24
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-guanine
<220> FEATURE:
<221> NAME/KEY: modified_base
<222> LOCATION: (6)..(6)
<223> OTHER INFORMATION: n represents iso-guanine
<220> FEATURE:
<221> NAME/KEY: misc_feature
```

```
<222> LOCATION: (10)..(11)
<223> OTHER INFORMATION: an n-propylene spacer (c3) between these
      locations

<400> SEQUENCE: 146
gtnatntgcg gaatgcacac tgcg                                          24

<210> SEQ ID NO 147
<211> LENGTH: 23
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-guanine
<220> FEATURE:
<221> NAME/KEY: modified_base
<222> LOCATION: (8)..(8)
<223> OTHER INFORMATION: n represents iso-guanine
<220> FEATURE:
<221> NAME/KEY: modified_base
<222> LOCATION: (9)..(9)
<223> OTHER INFORMATION: n represents iso-guanine
<220> FEATURE:
<221> NAME/KEY: misc_feature
<222> LOCATION: (10)..(11)
<223> OTHER INFORMATION: an n-propylene spacer (c3) between these
      locations

<400> SEQUENCE: 147
gatngtcnng gctagcggag gcc                                           23

<210> SEQ ID NO 148
<211> LENGTH: 23
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (3)..(3)
<223> OTHER INFORMATION: n represents iso-guanine
<220> FEATURE:
<221> NAME/KEY: modified_base
<222> LOCATION: (6)..(6)
<223> OTHER INFORMATION: n represents iso-guanine
<220> FEATURE:
<221> NAME/KEY: misc_feature
<222> LOCATION: (10)..(11)
<223> OTHER INFORMATION: an n-propylene spacer (c3) between these
      locations

<400> SEQUENCE: 148
ggnctnatgg gctagcggag gct                                           23

<210> SEQ ID NO 149
<211> LENGTH: 61
<212> TYPE: DNA
<213> ORGANISM: Artificial
<220> FEATURE:
<223> OTHER INFORMATION: synthetic oligonucleotide

<400> SEQUENCE: 149
cttctcccat tgcccagggc actctcctct gtagartaga ctgatytttg tggagacatc   60
a                                                                   61

<210> SEQ ID NO 150
<211> LENGTH: 35
<212> TYPE: DNA
```

```
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine
<220> FEATURE:
<221> NAME/KEY: modified_base
<222> LOCATION: (5)..(5)
<223> OTHER INFORMATION: n represents iso-cytosine
<220> FEATURE:
<221> NAME/KEY: modified_base
<222> LOCATION: (8)..(8)
<223> OTHER INFORMATION: n represents iso-cytosine
<220> FEATURE:
<221> NAME/KEY: modified_base
<222> LOCATION: (12)..(12)
<223> OTHER INFORMATION: n represents iso-cytosine

<400> SEQUENCE: 150
cngcnagnga tntgatgtct ccacaaagat cagtc                          35

<210> SEQ ID NO 151
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (4)..(4)
<223> OTHER INFORMATION: n represents iso-guanine
<220> FEATURE:
<221> NAME/KEY: modified_base
<222> LOCATION: (8)..(8)
<223> OTHER INFORMATION: n represents iso-guanine
<220> FEATURE:
<221> NAME/KEY: misc_feature
<222> LOCATION: (11)..(11)
<223> OTHER INFORMATION: an n-propylene spacer (c3) between these
      locations

<400> SEQUENCE: 151
ctancaancc cactctcctc tgtagaa                                    27

<210> SEQ ID NO 152
<211> LENGTH: 27
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (5)..(5)
<223> OTHER INFORMATION: n represents iso-guanine
<220> FEATURE:
<221> NAME/KEY: modified_base
<222> LOCATION: (7)..(7)
<223> OTHER INFORMATION: n represents iso-guanine
<220> FEATURE:
<221> NAME/KEY: misc_feature
<222> LOCATION: (10)..(11)
<223> OTHER INFORMATION: an n-propylene spacer (c3) between these
      locations

<400> SEQUENCE: 152
gagancnaag cactctcctc tgtagag                                    27

<210> SEQ ID NO 153
<211> LENGTH: 13
<212> TYPE: DNA
<213> ORGANISM: Artificial
<220> FEATURE:
```

```
<223> OTHER INFORMATION: synthetic oligonucleotide
<220> FEATURE:
<221> NAME/KEY: misc_feature
<222> LOCATION: (1)..(1)
<223> OTHER INFORMATION: n represents iso-guanine
<220> FEATURE:
<221> NAME/KEY: modified_base
<222> LOCATION: (2)..(2)
<223> OTHER INFORMATION: n represents iso-guanine
<220> FEATURE:
<221> NAME/KEY: modified_base
<222> LOCATION: (6)..(6)
<223> OTHER INFORMATION: n represents iso-guanine
<220> FEATURE:
<221> NAME/KEY: modified_base
<222> LOCATION: (9)..(9)
<223> OTHER INFORMATION: n represents iso-guanine
<220> FEATURE:
<221> NAME/KEY: modified_base
<222> LOCATION: (12)..(12)
<223> OTHER INFORMATION: n represents iso-guanine

<400> SEQUENCE: 153
nnatcnctng cng                                                        13

<210> SEQ ID NO 154
<211> LENGTH: 18
<212> TYPE: DNA
<213> ORGANISM: Artificial
<220> FEATURE:
<223> OTHER INFORMATION: synthetic oligonucleotide

<400> SEQUENCE: 154
agaacccttt cctcttcc                                                   18

<210> SEQ ID NO 155
<211> LENGTH: 47
<212> TYPE: DNA
<213> ORGANISM: Artificial
<220> FEATURE:
<223> OTHER INFORMATION: synthetic oligonucleotide

<400> SEQUENCE: 155 aagaacccctt tcctcttccg atgcaggata cttaacaata aatattt                  47

<210> SEQ ID NO 156
<211> LENGTH: 39
<212> TYPE: DNA
<213> ORGANISM: Artificial
<220> FEATURE:
<223> OTHER INFORMATION: synthetic oligonucleotide

<400> SEQUENCE: 156
gcagacagga yaaatattta ttgttaagta tcctgcatc                            39

<210> SEQ ID NO 157
<211> LENGTH: 20
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine

<400> SEQUENCE: 157
tncatctaac agggagcgcc                                                 20

<210> SEQ ID NO 158
```

```
<211> LENGTH: 25
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine

<400> SEQUENCE: 158
tntgatgtct ccacaaagat cagtc                                              25

<210> SEQ ID NO 159
<211> LENGTH: 18
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine

<400> SEQUENCE: 159
tncctgcaag ccagcacc                                                      18

<210> SEQ ID NO 160
<211> LENGTH: 23
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine

<400> SEQUENCE: 160
tngctggacc aggctagata agc                                                23

<210> SEQ ID NO 161
<211> LENGTH: 21
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine

<400> SEQUENCE: 161
tngcaaggct ctacttcctg c                                                  21

<210> SEQ ID NO 162
<211> LENGTH: 23
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine

<400> SEQUENCE: 162
tngtgtcttg gctgctcagt atg                                                23

<210> SEQ ID NO 163
```

```
<211> LENGTH: 24
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine

<400> SEQUENCE: 163
tncaacttct tggtcatggt tgtc                                              24

<210> SEQ ID NO 164
<211> LENGTH: 20
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine

<400> SEQUENCE: 164
tnccttcctg cactccacag                                                   20

<210> SEQ ID NO 165
<211> LENGTH: 19
<212> TYPE: DNA
<213> ORGANISM: Artificial
<220> FEATURE:
<223> OTHER INFORMATION: synthetic oligonucleotide
<220> FEATURE:
<221> NAME/KEY: modified_base
<222> LOCATION: (2)..(2)
<223> OTHER INFORMATION: n represents iso-cytosine

<400> SEQUENCE: 165
tntgagcagt cggtcagtg                                                    19
```

SOLID SUPPORT ASSAY SYSTEMS AND METHODS UTILIZING NON-STANDARD BASES

CROSS-REFERENCE TO RELATED APPLICATION

This application is a divisional of U.S. patent application Ser. No. 11/490,319 filed Jul. 20, 2006, now U.S. Pat. No. 8,217,160, which is a continuation of U.S. application Ser. No. 11/284,307, filed on Nov. 19, 2005, now U.S Pat. No. 7,892,796; which is a continuation of U.S. application Ser. No. 09/977,615, filed on Oct. 15, 2001, now U.S. Pat. No. 6,977,161; which claims the benefit of U.S. Provisional Application Ser. Nos. 60/293,259, filed on May 22, 2001; 60/282,831, filed on Apr. 10, 2001; and 60/240,397, filed on Oct. 14, 2000. U.S. application Ser. No. 09/977,615 is a continuation-in-part of U.S. application Ser. No. 09/861,292, filed on May 18, 2001, now U.S. Pat. No. 7,422,850, which claims the benefit of U.S. Provisional Application Ser. Nos. 60/282,831, filed on Apr. 10, 2001; 60/240,398, filed on Oct. 14, 2000; and 60/205,712, filed on May 19, 2000. The aforementioned applications are incorporated herein by reference in their entireties.

BACKGROUND OF THE INVENTION

A variety of different methods have been developed to assay oligonucleotides, including DNA or RNA fragments. Such assays are typically directed to determining whether a sample includes oligonucleotides having a particular target oligonucleotide sequence. In some instances, oligonucleotide sequences differ by only a few nucleotides, as in the case of many allelic sequences. Single nucleotide polymorphisms (SNPs) refer to alleles that differ by a single nucleotide. Even this single nucleotide difference can, at least in some instances, change the associated genetic response or traits. Accordingly, to determine which allele is present in a sample, the assay technique must be sufficiently sensitive to distinguish between closely related sequences.

Many assay techniques include multiple components, each of which hybridizes to other component(s) in the assay. Non-specific hybridization between components (i.e., the hybridization of two non-complementary sequences) produces background noise in the assay. For example, closely related, but not identical, sequences can form imperfect duplexes in which base pairing is interrupted at positions where the two single strands are not complementary. Non-specific hybridization increases when the hybridizing components have similar sequences, as would be the case, for example, for many alleles and particularly for SNP alleles. Thus, for example, hybridization assays to determine which allele is present in a sample would benefit from methods that reduce non-specific hybridization or reduce the impact of non-specific hybridization on the assay.

BRIEF SUMMARY OF THE INVENTION

Generally, the present invention relates to methods, kits, and compositions for assaying oligonucleotides. In addition, the invention relates to methods, kits, and compositions for assaying oligonucleotides using non-standard bases. One embodiment provides a method of assaying an analyte-specific sequence. A capture oligonucleotide comprising a molecular recognition sequence having at least one non-standard base coupled to a support (e.g., a single solid support, such as a chip or wafer, or a particulate support) is contacted with a sample under suitable hybridizing conditions to hybridize to a target oligonucleotide, if present in the sample. The target oligonucleotide comprises a tagging sequence complementary to the molecular recognition sequence of the capture oligonucleotide and the analyte-specific sequence or a complement of the analyte-specific sequence. Hybridization of the target oligonucleotide to the capture oligonucleotide is detected.

Another embodiment provides another method of assaying an analyte-specific sequence. A capture oligonucleotide coupled to a support and comprising a molecular recognition sequence that is the same as or complementary to at least a portion of the analyte-specific sequence is contacted with a sample under hybridizing conditions to hybridize to a target oligonucleotide. The target oligonucleotide comprises a tagging sequence comprising at least one non-standard base and the analyte-specific sequence or a complement of the analyte-specific sequence. The capture oligonucleotide is enzymatically extended using the target oligonucleotide as a template and a complementary non-standard base is incorporated opposite the non-standard base of the tagging sequence. A reporter group is also incorporated into an extended portion of the capture oligonucleotide. Hybridization of the target oligonucleotide to the capture oligonucleotide is detected.

Yet another embodiment provides another method of assaying an analyte-specific sequence. An analyte having the analyte-specific sequence is contacted with a first primer and a second primer. The first primer comprises a tagging sequence and a sequence complementary to a first sequence of the analyte. The second primer comprises a sequence complementary to a second sequence of the analyte and a non-standard base. The first and second primers are enzymatically extended to form a target oligonucleotide and a second oligonucleotide, respectively. One of the target oligonucleotide and the second oligonucleotide comprises the analyte-specific sequence, and the other comprises a sequence complementary to the analyte-specific sequence. Extension of the first primer is substantially halted when the non-standard base of the second primer is encountered. A non-standard base complementary to the non-standard base of the second primer is incorporated into the extended first primer opposite the non-standard base of the second primer. A capture oligonucleotide molecular recognition sequence that is the same as or complementary to at least a portion of the analyte-specific sequence coupled to a support is contacted with the target oligonucleotide under hybridizing conditions to hybridize to the target oligonucleotide comprising a tagging sequence and the analyte-specific sequence or complement thereof. Hybridization of the target oligonucleotide to the capture oligonucleotide is detected.

Other embodiments include kits for applying the methods described above. The kits include support(s) and capture oligonucleotides. The kits also include the target oligonucleotides or components for making the target oligonucleotides from an analyte. Such components can include, for example, a polymerase and first and second primers that are complementary to sequences of the analyte, where either the first or second primers include the tagging sequence. For some methods, the kit can also include a non-standard base or nucleotide triphosphate of a non-standard base for incorporation.

The above summary of the present invention is not intended to describe each disclosed embodiment or every implementation of the present invention. The Figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
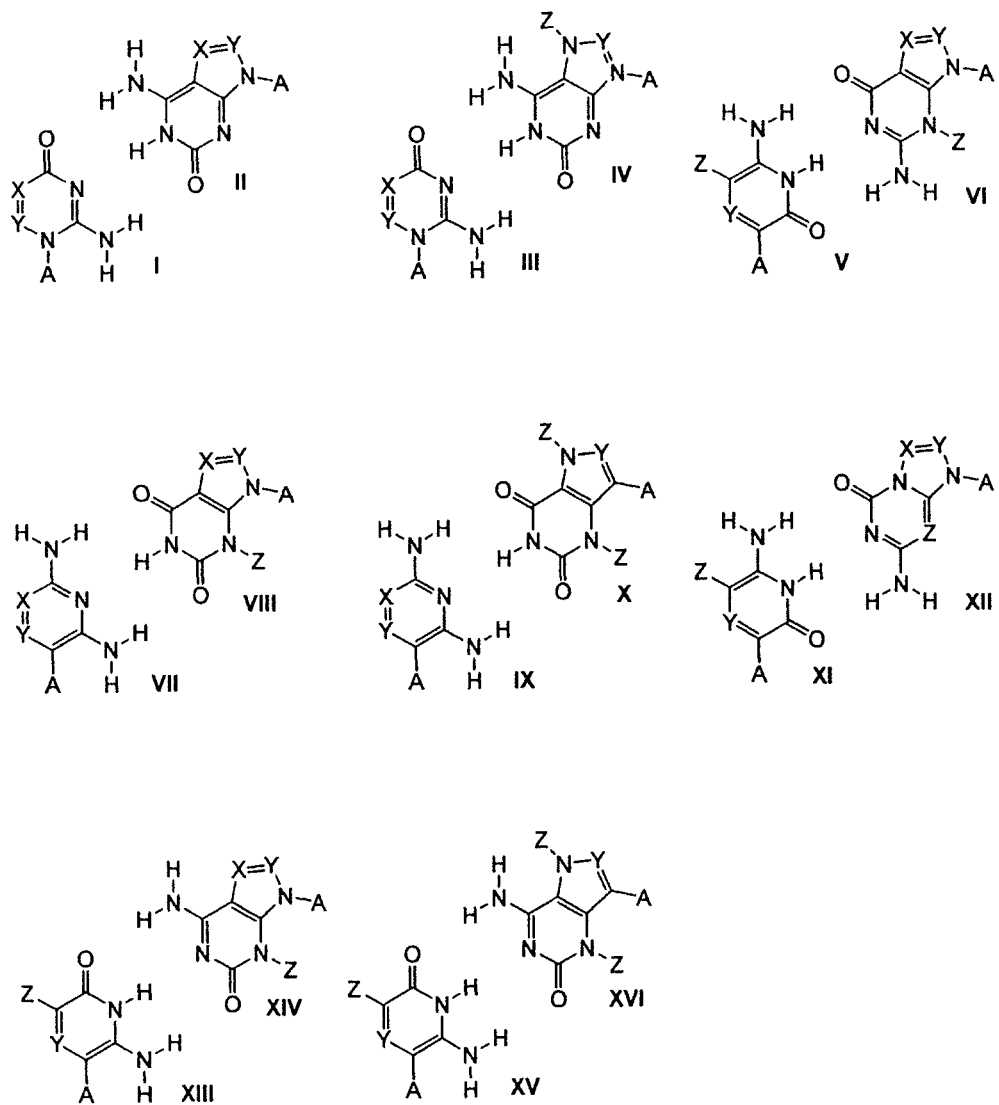
FIG. 1 displays chemical structures for a number of non-standard bases, where A is the point of attachment to a polymeric backbone, X is N or C—Z, Y is N or C—H, and Z is H or a substituted or unsubstituted alkyl group.

Although the invention is amenable to various modifications and alternative forms, specifics thereof have been shown by way of example in the drawings and will be described in detail. It should be understood, however, that the invention is not limited to the particular embodiments described. On the contrary, the intention is to cover all modifications, equivalents, and alternatives falling within the spirit and scope of the invention.

DETAILED DESCRIPTION OF THE PREFERRED EMBODIMENT

The present invention relates to assays and methods of assaying oligonucleotides. In particular, the present invention is directed to assays and methods of assaying oligonucleotides using one or more non-standard bases. Although the present invention is not so limited, an appreciation of various aspects of the inventions described herein will be gained through the discussion provided below. Other related assay methods for use with non-standard bases are described in U.S. Patent Provisional Application Ser. No. 60/240,397, filed Oct. 14, 2000.

As used herein, "nucleic acids" include polymeric molecules such as deoxyribonucleic acid (DNA), ribonucleic acid (RNA), peptide nucleic acid (PNA), or any sequence of what are commonly referred to as bases joined by a chemical backbone where the bases have the ability to form base pairs or hybridize with a complementary chemical structure. Suitable non-nucleotidic chemical backbones include, for example, polyamide and polymorpholino backbones. The term "nucleic acids" includes oligonucleotide, nucleotide, or polynucleotide sequences, and fragments or portions thereof. The nucleic acid can be provided in any suitable form, e.g., isolated from natural sources, recombinantly produced, or artificially synthesized, can be single- or double-stranded, and can represent the sense or antisense strand.

The term "oligonucleotide" refers generally to short chain (e.g., less than about 100 nucleotides in length, and typically 6 to 50 nucleotides in length) nucleic acid sequences as prepared using techniques presently available in the art such as, for example, solid support nucleic acid synthesis, DNA replication, reverse transcription, restriction digest, run-off transcription, or the like. The exact size of the oligonucleotide will typically depend upon a variety of factors, which in turn will depend upon the ultimate function or use of the oligonucleotide.

A "sequence" refers to an ordered arrangement of nucleotides.

The term "sample" includes a specimen or culture (e.g., microbiological cultures), as well as biological samples, samples derived from biological fluids, and samples from non-biological sources.

The term "analyte" refers to a nucleic acid suspected to be in a sample. The analyte is the object of the assay (e.g., the assay determines the presence, absence, concentration, or amount of the analyte in the sample). The analyte can be directly or indirectly assayed. In at least some embodiments involving indirect assay, the analyte, if present in the sample, is used as a template to form target oligonucleotides using, for example, PCR techniques. The target oligonucleotides are then assayed to indicate the presence, absence, concentration, or amount of the analyte in the sample.

The term "target oligonucleotide" refers to oligonucleotides that are actually assayed during an assay procedure. The target oligonucleotide can be, for example, an analyte or it can be an oligonucleotide containing an analyte-specific sequence that is the same as or complementary to a sequence of the analyte. For example, the target oligonucleotide can be a product of PCR amplification of an analyte or a portion of an analyte.

The term "capture oligonucleotide" refers to an oligonucleotide having a molecular recognition sequence and coupled to a solid surface to hybridize with a target oligonucleotide having a tagging sequence or an analyte specific sequence complementary to the molecular recognition sequence, thereby capturing the target oligonucleotide on the solid surface.

A "molecular recognition sequence" as used herein is an oligonucleotide sequence complementary to the tagging sequence or to the analyte-specific sequence of a target oligonucleotide.

As used herein, the terms "complementary" or "complementarity," when used in reference to nucleic acids (i.e., a sequence of nucleotides such as an oligonucleotide or a target nucleic acid), refer to sequences that are related by base-pairing rules. For natural bases, the base pairing rules are those developed by Watson and Crick. For non-standard bases, as described herein, the base-pairing rules refer to the formation of hydrogen bonds in a manner similar to the Watson-Crick base pairing rules or the formation of specific base pairs by hydrophobic, entropic, or van der Waals forces. As an example, for the sequence "T-G-A", the complementary sequence is "A-C-T." Complementarity can be "partial," in which only some of the bases of the nucleic acids are matched according to the base pairing rules. Alternatively, there can be "complete" or "total" complementarity between the nucleic acids. The degree of complementarity between the nucleic acid strands affects the efficiency and strength of hybridization between the nucleic acid strands.

The term "hybridization" is used in reference to the pairing of complementary nucleic acids. Hybridization and the strength of hybridization (i.e., the strength of the association between the nucleic acids) is influenced by such factors as the degree of complementarity between the nucleic acids, stringency of the hybridization conditions involved, the melting temperature ($T_m$) of the formed hybrid, and the G:C ratio within the nucleic acids.

Assays are performed to determine whether a sample includes an analyte having a particular nucleic acid sequence (or its complement). This nucleic acid sequence will be referred to as the "analyte-specific sequence". In at least some instances, the original sample is not directly assayed. Instead, the analyte, if present, is cloned or amplified (e.g., by PCR techniques) to provide an assay sample with a detectable amount of a target oligonucleotide that contains the analyte-specific sequence. Other techniques for amplification include, for example, nucleic acid sequence based amplification (NASBA, e.g., Guatelli, et al., Proc. Nat'l. Acad. Sci. 87, 1874 (1990), incorporated herein by reference), strand displacement amplification (SDA, e.g., Walker, et al., Proc. Nat'l. Acad. Sci. 89, 392-96 (1992), incorporated herein by reference), ligase chain reaction (LCR, e.g., Kalin, et al., Mutat. Res., 283, 119-23 (1992), incorporated herein by reference), transcription mediated amplification (TMA, e.g., La Rocco, et al., Eur. J. Clin. Microbiol. Infect. Dis., 13, 726-31 (1994), incorporated herein by reference), and rolling circle amplification (RCA, e.g., Lizardi, et al., Nat. Genet., 19, 225-32 (1998), incorporated herein by reference). At least a portion of the target oligonucleotide typically corresponds to either a) the analyte, b) a portion of the analyte, c) a complement of the analyte, or d) a complement of a portion of the analyte. Detection of the target oligonucleotide by the assay indicates presence of the analyte in the original sample.

In general, an assay system for detecting one or more analyte-specific sequences includes a solid support (e.g., a chip, wafer, or a collection of solid particles). Capture oligonucleotides are disposed on the solid support in a manner which permits identification of the capture oligonucleotide (e.g., by position on a chip or wafer or by unique characteristic of particles to which particular capture oligonucleotides are attached). The capture oligonucleotides include a molecular recognition sequence. Different capture oligonucleotides with different molecular recognition sequences are used to detect different analyte-specific sequences. Using these different capture oligonucleotides, a single assay system can be designed to analyze a sample for multiple analyte-specific sequences.

Target oligonucleotides containing the analyte-specific sequences are brought into contact with the capture oligonucleotides. In addition to the analyte-specific sequence, the target oligonucleotides also each include a tagging sequence. A particular tagging sequence is associated with each analyte-specific sequence. The tagging sequence is generally complementary to one of the molecular recognition sequences. Thus, under hybridization conditions, the target oligonucleotides hybridize with the appropriate capture oligonucleotides. Alternatively, in certain methods of the present invention, the analyte-specific sequence may be complementary to one of the molecular recognition sequences.

The target oligonucleotide or its complement typically includes a reporter or a coupling agent for attachment of a reporter. Observation of the solid support to determine the presence or absence of the reporter associated with a particular capture oligonucleotide indicates whether a particular analyte-specific sequence is present in the sample. Suitable reporters include, without limitation, biotin, fluorescents, chemilluminescents, digoxigenin, spin labels, radio labels, DNA cleavage moieties, chromaphors or fluoraphors. Examples of suitable coupling moieties include, but are not limited to, amines, thiols, hydrosines, alcohols or alkyl groups.

Figure 2A:
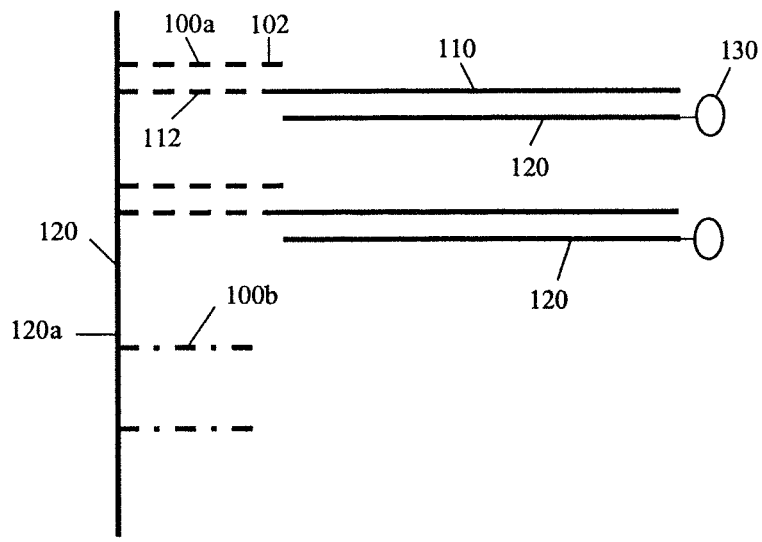
FIGS. 2A and 2B schematically illustrate two examples of oligonucleotide hybridization to a solid support, according to the invention.
Figure 2B:
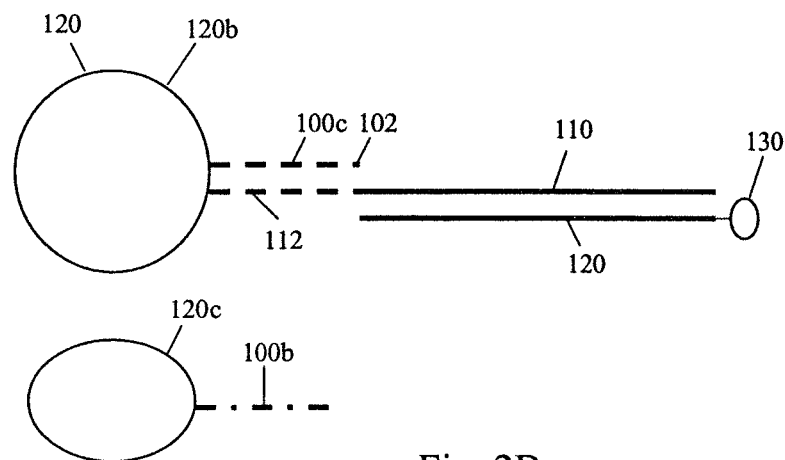

Examples of suitable assay systems are schematically illustrated in FIGS. 2A and 2B. In these assays, capture oligonucleotides 100a, 100b are coupled to a solid support 120, such as, for example, a single solid substrate 120a (e.g., a chip or wafer) or one of a number of solid particles 120b. Typically, at least one of the capture oligonucleotides (e.g., capture oligonucleotide 100a) has a molecular recognition sequence 102 that is complementary to a tagging sequence 112 of a target oligonucleotide 110 so that, under hybridization conditions, the target oligonucleotide 110 hybridizes to the capture oligonucleotide 100a.

Although assays can be prepared with all of the capture oligonucleotides having the same global molecular recognition sequence, typically, two or more different groups of capture oligonucleotides 100a, 100b are used. Each group of capture oligonucleotides has a different molecular recognition sequence. On a single solid substrate, each group of capture oligonucleotides are typically disposed on a particular region or regions of the substrate such that the region(s) is/are associated with a particular molecular recognition sequence. When a particle support is used, each group of capture oligonucleotides 100a, 100b is disposed on at least one group of particles 120b, 120c having a unique characteristic such that the capture oligonucleotide of a particular particle is determined from the characteristic of the particle to which it is attached. Such assays can be used to, for example, a) determine which allele is present in a sample by associating different capture oligonucleotides (and different regions of a substrate or different groups of particles) with each allele, b) assay for multiple related or unrelated oligonucleotides or c) both. As illustrated in FIGS. 2A and 2B, the target oligonucleotide preferentially hybridizes to a corresponding capture oligonucleotide permitting determination of the presence or absence of an analyte-specific sequence by observation of the presence or absence of a target oligonucleotide on a particular spatial position of the single support (FIG. 2A) or attached to a particular group of particles (FIG. 2B).

An additional component of the assay system is a reporter 130 that couples to the target oligonucleotide 110 (or its complement 120), as described below. The reporter 130 is the component of the assay that is subsequently detected by a detection technique (e.g., by colorimetric, fluorescence, electrophoretic, electrochemical, spectroscopic, chromatographic, densitometric, or radiographic techniques) to indicate the presence or concentration of the target oligonucleotide. The reporter will typically be determined by the detection technique (e.g., fluorophore reporters for fluorescent techniques and radio-labels for radiographic techniques.)

In some assays, one or both of the capture oligonucleotide and the target oligonucleotide include at least one non-standard base. The use of non-standard base(s) can improve the specificity of an assay that includes hybridization because non-standard bases preferentially hybridize to other complementary non-standard bases. The use of longer oligonucleotides can also increase the rate of specific hybridization. The hybridization of nucleic acids generally includes the sampling of about three to four bases for complete complementarity. These form nucleation sites. If a nucleation site is found, the hybridization proceeds down the strand. If the bases down the strand are not complementary, then the two strands release. Because the nucleation process takes time, the possibilities of finding a nucleation site when non-standard bases are used is reduced, thereby reducing the number of sampling steps needed to find a complete complement.

Alternatively, the non-standard bases are used to direct the addition of another non-standard base into a sequence (using, for example, PCR techniques). The added non-standard base can include a reporter or a coupling agent to which a reporter can be attached, thereby, permitting the highly selective incorporation of a reporter group for detection of the target oligonucleotide.

Oligonucleotides and Bases

DNA and RNA are oligonucleotides that include deoxyriboses or riboses, respectively, coupled by phosphodiester bonds. Each deoxyribose or ribose includes a base coupled to a sugar. The bases incorporated in naturally-occurring DNA and RNA are adenosine (A), guanosine (G), thymidine (T), cytidine (C), and uridine (U). These five bases are "natural bases". According to the rules of base pairing elaborated by Watson and Crick, the natural bases can hybridize to form purine-pyrimidine base pairs, where G pairs with C and A pairs with T or U. These pairing rules facilitate specific hybridization of an oligonucleotide with a complementary oligonucleotide.

The formation of these base pairs by the natural bases is facilitated by the generation of two or three hydrogen bonds between the two bases of each base pair. Each of the bases includes two or three hydrogen bond donor(s) and hydrogen bond acceptor(s). The hydrogen bonds of the base pair are each formed by the interaction of at least one hydrogen bond donor on one base with a hydrogen bond acceptor on the other base. Hydrogen bond donors include, for example, heteroatoms (e.g., oxygen or nitrogen) that have at least one attached hydrogen. Hydrogen bond acceptors include, for example, heteroatoms (e.g., oxygen or nitrogen) that have a lone pair of electrons.

The natural bases, A, G, C, T, and U, can be derivatized by substitution at non-hydrogen bonding sites to form modified natural bases. For example, a natural base can be derivatized for attachment to a support by coupling a reactive functional group (e.g., thiol, hydrazine, alcohol, or amine) to a non-hydrogen bonding atom of the base. Other possible substituents include biotin, digoxigenin, fluorescent groups, and alkyl groups (e.g., methyl or ethyl).

Non-standard bases, which form hydrogen-bonding base pairs, can also be constructed as described, for example, in U.S. Pat. Nos. 5,432,272, 5,965,364, 6,001,983, and 6,037,120 and U.S. patent application Ser. No. 08/775,401, all of which are incorporated herein by reference. By "non-standard base" it is meant a base other than A, G, C, T, or U that is susceptible of incorporation into an oligonucleotide and which is capable of base-pairing by hydrogen bonding, or by hydrophobic, entropic, or van der Waals interactions to form base pairs with a complementary base. FIG. 1 illustrates several examples of suitable bases and their corresponding base pairs. Specific examples of these bases include the following bases in base pair combinations (iso-C/iso-G, K/X, H/J, and M/N):

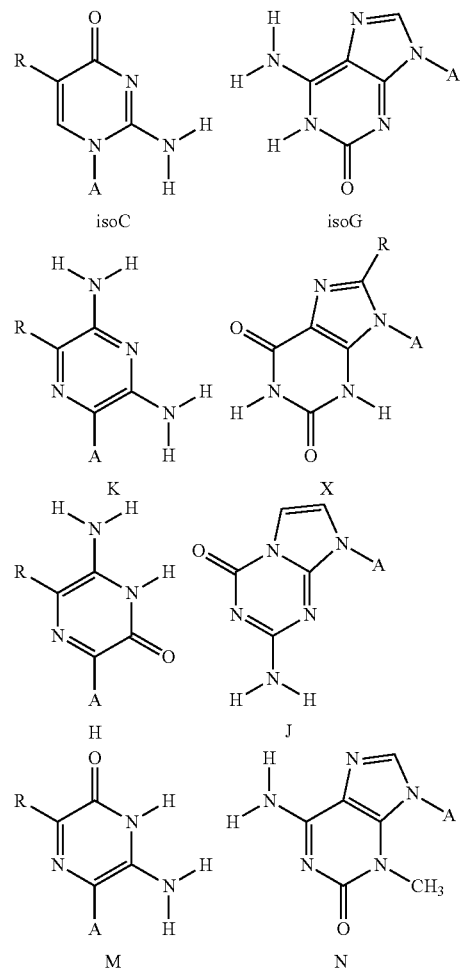

where A is the point of attachment to the sugar or other portion of the polymeric backbone and R is H or a substituted or unsubstituted alkyl group. It will be recognized that other non-standard bases utilizing hydrogen bonding can be prepared, as well as modifications of the above-identified non-standard bases by incorporation of functional groups at the non-hydrogen bonding atoms of the bases. To designate these non-standard bases in FIGS. 3 to 9, the following symbols will be used: X indicates iso-C and Y indicates iso-G.

The hydrogen bonding of these non-standard base pairs is similar to those of the natural bases where two or three hydrogen bonds are formed between hydrogen bond acceptors and hydrogen bond donors of the pairing non-standard bases. One of the differences between the natural bases and these non-standard bases is the number and position of hydrogen bond acceptors and hydrogen bond donors. For example, cytosine can be considered a donor/acceptor/acceptor base with guanine being the complementary acceptor/donor/donor base. Iso-C is an acceptor/acceptor/donor base and iso-G is the complementary donor/donor/acceptor base, as illustrated in U.S. Pat. No. 6,037,120, incorporated herein by reference.

Other non-standard bases for use in oligonucleotides include, for example, naphthalene, phenanthrene, and pyrene derivatives as discussed, for example, in Ren et al., *J. Am. Chem. Soc.* 118, 1671 (1996) and McMinn et al., *J. Am. Chem. Soc.* 121, 11585 (1999), both of which are incorporated herein by reference. These bases do not utilize hydrogen bonding for stabilization, but instead rely on hydrophobic, entropic, or van der Waals interactions to form base pairs.

Solid Supports

The assay is carried out, at least in part, using a solid support. Generally, the capture oligonucleotides are coupled to or otherwise disposed on a surface of the support. A variety of different supports can be used. In some embodiments, the solid support is a single solid support, such as a chip or wafer, or the interior or exterior surface of a tube, cone, or other article. The solid support is fabricated from any suitable material to provide an optimal combination of such desired properties as stability, dimensions, shape, and surface smoothness. Preferred materials do not interfere with nucleic acid hybridization and are not subject to high amounts of non-specific binding of nucleic acids. Suitable materials include biological or nonbiological, organic or inorganic materials. For example, the master array can be fabricated from any suitable plastic or polymer, silicon, glass, ceramic, or metal, and can be provided in the form of a solid, resin, gel, rigid film, or flexible membrane. Suitable polymers include, for example, polystyrene, poly(alkyl)methacrylate, poly(vinylbenzophenone), polycarbonate, polyethylene, polypropylene, polyamide, polyvinylidenefluoride, and the like. Preferred materials include polystyrene, glass, and silicon.

Figure 3:
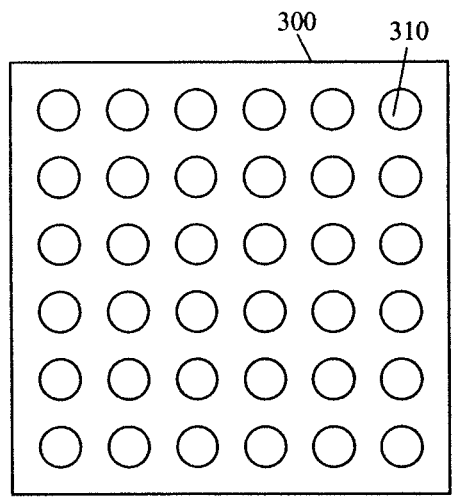
FIG. 3 illustrates steps in a first assay for an analyte-specific sequence, according to the invention.

In some embodiments, the single solid support 300 is divided into individual regions 310 with capture oligonucleotides disposed on the support in each region, as illustrated in FIG. 3. In each of the regions or on each particle support, the capture oligonucleotides have predominantly (e.g., at least 75%) the same molecular recognition sequence. Preferably, substantially all (e.g., at least 90% and, more preferably, at least 99%) of the capture oligonucleotides have the same molecular recognition sequence in each region or on each particle support. The capture oligonucleotides of different regions typically have different sequences, although in some instances, the same capture oligonucleotides can be used in two or more regions, for example, as a control or verification of results.

A solid support with different regions can form a regular or irregular array for testing samples and determining the presence or absence of a number of different analyte-specific sequences. For example, an array can be formed to test for 10, 100, 1000 or more different analyte-specific sequences.

Dimensions of the solid support are determined based upon such factors as the desired number of regions and the number of analyte-specific sequences to be assayed. As an example, a solid support can be provided with planar dimensions of about 0.5 cm to about 7.5 cm in length, and about 0.5 cm to about 7.5 cm in width. Solid supports can also be singly or multiply positioned on other supports, such as microscope slides (e.g., having dimensions of about 7.5 cm by about 2.5 cm). The dimensions of the solid support can be readily adapted for a particular application.

Other types of solid supports can be used. In some embodiments, the solid support is a particulate support. In these embodiments, the capture oligonucleotides are coupled to particles. Typically, the particles form groups in which particles within each group have a particular characteristic, such as, for example, color, fluorescence frequency, density, size, or shape, which can be used to distinguish or separate those particles from particles of other groups. Preferably, the particles can be separated using techniques, such as, for example, flow cytometry.

As contemplated in the invention, the particles can be fabricated from virtually any insoluble or solid material. For example, the particles can be fabricated from silica gel, glass, nylon, resins, Sephadex™, Sepharose™, cellulose, magnetic material, a metal (e.g., steel, gold, silver, aluminum, copper, or an alloy) or metal-coated material, a plastic material (e.g., polyethylene, polypropylene, polyamide, polyester, polyvinylidenefluoride (PVDF)) and the like, and combinations thereof. Examples of suitable micro-beads are described, for example, in U.S. Pat. Nos. 5,736,330, 6,046,807, and 6,057,107, all of which are incorporated herein by reference. Examples of suitable particles are available, for example, from Luminex Corp., Austin, Tex.

In one embodiment, the particulate supports with associated capture oligonucleotides are disposed in a holder, such as, for example, a vial, tube, or well. The target oligonucleotide is added to the holder and the assay is conducted under hybridization conditions. The particulate supports are then separated on the basis of the unique characteristics of each group of supports. The groups of supports are then investigated to determine which support(s) have attached target oligonucleotides. Optionally, the supports can be washed to reduce the effects of cross-hybridization. One or more washes can be performed at the same or different levels of stringency, as described below. As another optional alternative, prior to contact with the support(s) and capture oligonucleotides, the solution containing target oligonucleotides can be subjected to, for example, size exclusion chromatography, differential precipitation, spin columns, or filter columns to remove primers that have not been amplified or to remove other materials that are not the same size as the target oligonucleotides.

In some embodiments, multiple holders (e.g., vials, tubes, and the like) are used to assay multiple samples or have different combinations of capture oligonucleotides (and associated supports) within each holder. As another alternative, each holder can include a single type of capture oligonucleotide (and associated support).

As another example, the support can be a group of individual support surfaces that are optionally coupled together. For example, the support can include individual optical fibers or other support members that are individually coupled to different capture oligonucleotides and then bound together to form a single article, such as a matrix.

Typically, the support (whether a single or particulate support) is capable of binding or otherwise holding the capture oligonucleotide to the surface of the support in a sufficiently stable manner to accomplish the purposes described herein. Such binding can include, for example, the formation of covalent, ionic, coordinative, hydrogen, or van der Waals bonds between the support and the capture oligonucleotides or attraction to a positively or negatively charged support. Capture oligonucleotides are attached to the solid support surface directly or via linkers. In one embodiment, capture oligonucleotides are directly attached to the support surface by providing or derivatizing either the surface, the oligonucleotide, or both, with one or more reactive groups. For example, the surface of the Luminex™ particles can be modified with, for example, carboxylate, maleimide, or hydrazide functionalities or avidin and glass surfaces can be treated with, for example, silane or aldehyde (to form Schiff base aldehyde-amine couplings with DNA). In some embodiments, the support or a material disposed on the support (as, for example, a coating on the support) includes reactive functional groups that can couple with a reactive functional group on the capture oligonucleotides. As examples, the support can be functionalized (e.g., a metal or polymer surface that is reactively functionalized) or contain functionalities (e.g., a polymer with pending functional groups) to provide sites for coupling the capture oligonucleotides.

As an alternative, the capture oligonucleotides can be retained on the surface by cross-linking of the capture oligonucleotides. Preferably, a capture oligonucleotide that is cross-linked includes a cross-linking portion and a capture portion, where the capture portion includes a molecular recognition sequence that hybridizes to the tagging sequence of the target oligonucleotide.

As yet another alternative, the support can be partially or completely coated with a binding agent, such as streptavidin, antibody, antigen, enzyme, enzyme cofactor or inhibitor, hormone, or hormone receptor. The binding agent is typically a biological or synthetic molecule that has high affinity for another molecule or macromolecule, through covalent or non-covalent bonding. The capture oligonucleotide is coupled to a complement of the binding agent (e.g., biotin, antigen, antibody, enzyme cofactor or inhibitor, enzyme, hormone receptor, or hormone). The capture oligonucleotide is then brought in contact with the binding agent to hold the capture oligonucleotide on the support. Other known coupling techniques can be readily adapted and used in the systems and methods described herein.

Capture and Target Oligonucleotides

The capture oligonucleotide includes a molecular recognition sequence that can capture, by hybridization, a target oligonucleotide having a complementary tagging sequence. The hybridization of the molecular recognition sequence of a capture oligonucleotide and the tagging sequence of a target oligonucleotide results in the coupling of the target oligonucleotide to the solid support. The molecular recognition sequence and tagging sequence are associated with a particular analyte-specific sequence (also part of the target oligonucleotide), thus indicating, if hybridization occurs, the presence or concentration of analyte with the analyte-specific sequence (or its complement) in the original sample.

The coding and tagging sequences typically include at least six nucleotides and, in some instances, include at least 8, 10, 15, or 20 or more nucleotides. In some assays, as described below, the molecular recognition sequence and tagging sequence include one or more non-standard bases. In other assays, the molecular recognition sequence and tagging sequence do not contain non-standard bases.

The capture oligonucleotide also typically includes a functional group that permits binding of the capture oligonucleotide to the solid support or functional groups disposed on or extending from the solid support. The functional group can be attached directly to the polymeric backbone or can be attached to a base in the nucleotidic sequence. As an alternative, the capture oligonucleotide can include a crosslinking portion to facilitate crosslinking, as described above, or can be electrostatically held on the surface. The capture oligonucleotides can be formed by a variety of techniques, including, for example, solid state synthesis, DNA replication, reverse transcription, restriction digest, run-off transcription, and the like.

In addition to the tagging sequence, the target oligonucleotide includes an analyte-specific sequence which corresponds to or is a complement to a sequence of interest in the analyte. The analyte-specific sequence can be independent from the tagging sequence or some or all of the tagging sequence can be part of the analyte-specific sequence.

The length of the capture oligonucleotides can be optimized for desired hybridization strength and kinetics. Usually, the length of the molecular recognition sequence is in the 6 to 20 (preferably, 8 to 12) nucleotide range. In a preferred embodiment, the different molecular recognition sequences of the capture oligonucleotides are not complementary to one another and, more preferably, to any known natural gene sequence or gene fragment that has a significant probability of being present in a substantial amount in the sample to be tested. As a result, the capture molecular recognition sequences of the capture oligonucleotides will primarily hybridize to the respective complementary tagging sequences of the target oligonucleotides.

The target oligonucleotide (or an oligonucleotide complementary to at least a portion of the target oligonucleotide) includes a reporter or a coupling agent for attachment of a reporter. The reporter or coupling agent can be attached to the polymeric backbone or any of the bases of the target or complementary oligonucleotide. Techniques are known for attaching a reporter group to nucleotide bases (both natural and non-standard bases). Examples of reporter groups include biotin, digoxigenin, spin-label groups, radio labels, DNA-cleaving moieties, chromaphores, and fluorophores such as fluoroscein. Examples of coupling agents include biotin or substituents containing reactive functional groups. The reporter group is then attached to streptavidin or contains a reactive functional group that interacts with the coupling agent to bind the reporter group to the target or complementary oligonucleotide.

Polymerase Chain Reaction (PCR) Techniques

A variety of Polymerase Chain Reaction (PCR) techniques are known and can be used in the assays described below. PCR techniques are typically used for the amplification of at least a portion of an oligonucleotide. The sample to be tested for the presence of an analyte-specific sequence is contacted with the first and second oligonucleotide primers; a nucleic acid polymerase; and nucleotide triphosphates corresponding to the nucleotides to be added during PCR. The natural base nucleotide triphosphates include dATP, dCTP, dGTP, dTTP, and dUTP. Nucleoside triphosphates of non-standard bases can also be added, if desired or needed. Suitable polymerases for PCR are known and include, for example, thermostable polymerases such as native and altered polymerases of *Thermus* species, including, but not limited to *Thermus aquaticus* (Taq), *Thermus flavus* (Tfl), and *Thermus thermophilus* (Tth), as well as the Klenow fragment of DNA polymerase I and the HIV-1 polymerase.

The first and second primers are complementary to different portions on different strands of the double stranded oligonucleotide that is to be amplified. The sequence of the oligonucleotide that is amplified includes the two primer sequences that hybridize to the analyte and the region between the two primers. The primers can be formed by a variety of techniques including, for example, solid state synthesis, DNA replication, reverse transcription, restriction digest, run-off transcription, and the like.

PCR includes the cycling steps of (i) annealing the first oligonucleotide primer and the second oligonucleotide primer to the double stranded oligonucleotide that is to be amplified or to extension products formed in previous cycles; (ii) extending the annealed first and second oligonucleotide primers by the nucleic acid polymerase to synthesize primer extension products; and (iii) denaturing the products to obtain single stranded nucleic acids. Varieties of PCR have been developed by modifying the steps or varying conditions (e.g., time and temperature). Generally, any of these varieties of PCR can be used in the assays described below, although some may be more useful than others for particular assays.

One variety of PCR developed for some of the assays described below is "fast-shot PCR" in which primer extension times are reduced or eliminated. As used herein, the term "fast-shot polymerase chain reaction" or "fast-shot PCR" refers to PCR where the extension stop, as well as the stops for the annealing and melting steps, are very short or eliminated. Typically, for this method, the 3' ends of the two primers are separated by no more than 10 bases on the template nucleic acid.

Enhanced specificity is achieved by using fast-shot PCR cycles where the extension stop, as well as the stops for the annealing and melting steps, are very short or eliminated. In some embodiments, the PCR solution is rapidly cycled between about 90 to 100° C. and about 55 to 65° C. with a maximum of about a one second hold at each temperature, thereby leaving the polymerase very little time to extend mismatched primers. In one embodiment, the reaction is cycled between about 95° C. and about 58° C. with about a one second hold at each temperature.

This rapid cycling is facilitated by generating a short PCR product by, in general, leaving a gap of about zero (0) to ten (10) bases on the template nucleic acid between the 3' bases of the first and second primers. Preferably, the primers are designed to have a Tm of approximately 55 to 60° C. For some embodiments, a total of about 37 cycles is typically adequate to detect as little as 30 target oligonucleotides.

Allele specific PCR primers can be used to discriminate SNP (single nucleotide polymorphism) and other alleles. For SNP detection, these primers are designed to be complementary to each allele such that the polymorphic base of interest is positioned at or near (typically, within three or five bases) the 3' end of the first or second primer. High levels of allelic discrimination are achieved in part by the limited ability of Taq polymerase to extend a primer which has a nucleotide mismatch at its 3' end with that of the target DNA, i.e., the corresponding allele to which the primer is not specific. Other polymerases can also be used.

Additionally, allelic discrimination can be obtained by placing the mismatch at other positions in the allele specific primer. These alternate positions for the nucleotide mismatch in the primer can be used to achieve selective amplification in two primary ways: 1) by simply lowering the Tm (melting temperature) of the primer so that it is not hybridized on the template DNA during thermal cycling so that the polymerase can not extend the primers, or 2) by creating an unfavorable primer/template structure that the polymerase will not extend.

Figure 4:
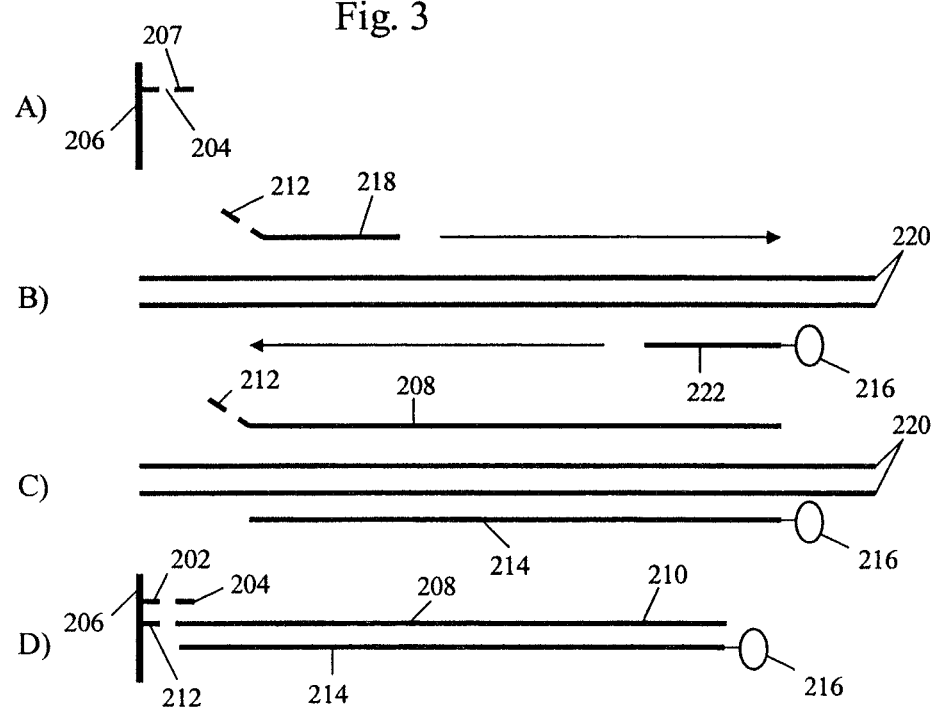
FIG. 4 illustrates steps in a second assay for an analyte-specific sequence, according to the invention.

Examples of Assays
Assays with Non-standard Bases in the Coding and Tagging Sequences In one assay illustrated in FIG. 4, two or more groups of capture oligonucleotides 202 are prepared. Each group of capture oligonucleotides 202 includes a unique molecular recognition sequence 204. The molecular recognition sequence of each group includes at least one (and, typically, two or more) non-standard bases (denoted by the use of dashed lines in the Figures). The use of non-standard bases substantially reduces the likelihood that the capture oligonucleotides will hybridize with sequences that include only natural bases. This will typically result in less non-specific hybridization when compared to a similar assay using oligonucleotides with only natural bases. The capture oligonucleotide also typically includes a reactive functional group for attachment to the solid support 206, although other attachment methods can be used, as described above.

The support for the assay can be, for example, a single solid support, such as, for example, a glass, metal, plastic, or inorganic chip. The capture oligonucleotides are disposed on the support and typically held by one of the methods described above (e.g., coupling via reactive groups on the capture oligonucleotide and support, use of a binding agent disposed on the support, or cross-linking of the capture oligonucleotides). Each of the groups is disposed in one or more unique regions of the solid support so that the region(s) can be associated with a particular capture oligonucleotide.

In another embodiment (not shown), the support for the assay is a particulate support (e.g., beads). It will be understood that any of the assays described herein can be performed on a single solid support, on a particulate support, or any other support. The particulate support is divided into groups of particles, each group of particles having a characteristic (e.g., color, shape, size, density, or other chemical or physical property) that distinguishes that group of particles from other groups. Each group of capture oligonucleotides is coupled to one or more groups of particles. This produces an association of a particular group of particles with a particular group of capture oligonucleotides, allowing the determination of the capture oligonucleotide by observation of the unique particle support characteristic.

Returning to FIG. 4, the target oligonucleotide 208, if present in the assayed sample, contains an analyte-specific sequence 210 and a tagging sequence 212 complementary to the molecular recognition sequence 204 of one group of the capture oligonucleotides 202. The tagging sequence 212 contains at least one non-standard base; otherwise the tagging sequence would not be complementary to the molecular recognition sequence of the capture oligonucleotide. An oligonucleotide 214 complementary to a portion of the target oligonucleotide 208 includes a reporter 216 or a coupling agent (not shown) for attachment of a reporter.

The target oligonucleotide 208 and complementary oligonucleotide 214 can be formed by, for example, PCR amplification of an analyte containing the analyte-specific sequence or its complement. In PCR amplification, two different primers are used (as illustrated at B of FIG. 4). A first primer 218 contains a sequence complementary to a first sequence on a first strand of the analyte 220. A second primer 222 contains a sequence that is the complementary to a second sequence on a second strand of the analyte 220 which is upstream or downstream of the first sequence. The analyte-specific sequence typically includes the sequence of the analyte stretching between, and including, the sequences (or complements) to which the primers hybridize. The first primer 218 includes the tagging sequence 212 and the second primer 222 includes the reporter 216 (or a coupling agent for a reporter). Extension of the first and second primers and amplification proceeds using known PCR amplification techniques or the fast-shot PCR techniques described above to produce the target oligonucleotide 208 and complementary oligonucleotide 214 (as illustrated at C of FIG. 4). Other known synthetic methods, such as, for example, solid state synthesis, DNA replication, reverse transcription and the like, can be used to form the target and complementary oligonucleotides.

Returning to the assay, the target oligonucleotide 208 is typically brought into contact with the support 206 (or a container holding a particulate support) with associated capture oligonucleotides 202. Conditions are controlled to promote selective hybridization of the tagging sequence of the target oligonucleotide with a complementary molecular recognition sequence of a capture oligonucleotide, if an appropriate capture oligonucleotide is present on the support (as illustrated at D of FIG. 4). A reporter is also added (unless the complementary oligonucleotide 214 already contains the reporter) for coupling to the complementary oligonucleotide 214. Optionally, unincorporated primers can be removed prior to hybridization by techniques such as, for example, size exclusion chromatography, differential precipitation, spin columns, or filter columns, or after hybridization by, for example, washing.

For assays on a planar solid support, the assay can be read by determining whether the reporter group is present at each of the individual regions on the support. The presence of the reporter group indicates that the original sample contains an analyte having the analyte-specific sequence associated with the particular tagging sequence and molecular recognition sequence for that region of the support. The absence of the reporter group suggests that the sample did not contain an analyte having the particular analyte-specific sequence.

For assays on particle supports, the particles can be separated according to the unique characteristics and then it is determined which particles have a reporter coupled to the particle via the capture and target oligonucleotides. Techniques for accomplishing the separation include, for example, flow cytometry. The presence of the reporter group indicates that the sample contains the target oligonucleotide having the analyte-specific sequence associated with a particular tagging sequence and the molecular recognition sequence of a particular capture oligonucleotide.

The assay illustrated in FIG. 4 can be adapted for use in determining the presence of alleles in a sample. For example, the assay includes allele-specific primers (either the first or second primers 218, 222 or both) corresponding to two or more alleles. Each of the allele-specific primers includes a sequence that specifically hybridizes to only one allele. The tagging sequence or reporter (or coupling agent) attached to the allele-specific primer is also specific for the allele. If the allele is present in the sample, the allele-specific primer(s) associated with that allele will extend and will be detected by either hybridizing to a complementary, allele-specific capture oligonucleotide on the support or observing an allele-specific reporter group. It will be recognized that the assay can also be used to determine the presence or absence of non-allelic analyte-specific sequences in the analyte.

This method can be used to detect SNP (single nucleotide polymorphism) alleles. Either the first or second primers will be SNP-specific. Typically, two (or more) different SNP-specific primers will be used in the assay. Preferably, the SNP-specific primers will have the SNP site positioned at or near (e.g., within three or five bases) the extendable end of the primer. "Fast-shot PCR" techniques can be useful in this SNP assay because the short extension times will substantially reduce the likelihood that non-complementary primers will extend.

Hybridization of the capture oligonucleotides and target oligonucleotides is a feature of the assays described herein. This hybridization takes place in a hybridization mixture that contains salts (e.g., sodium salts or magnesium salts), a buffer (e.g., TRIS, TAPS, BICINE, or MOPs), a non-specific blocking agent (e.g., SDS, BSA, or sheared genomic DNA), and a protecting agent (e.g., EDTA or an azide), as is used in many conventional hybridization methods. Typically, the hybridization takes place at a sodium ion (or other cation) concentration of at least 0.01 to 1.0 M and a pH of 7.0 to 8.3. Generally, this hybridization and any washing steps are performed at a temperature and salt concentration that meet desired stringency conditions for maintaining hybridization. Stringency conditions are sequence dependent. Stepwise increases in stringency conditions can be used, if desired, over several washing steps.

"Low stringency conditions" are selected to be about 10 to 15° C. below the thermal melting point (Tm) for the specific sequence at the ionic strength and pH of the hybridizing solution. Tm is the temperature (for the ionic strength, pH, and nucleic acid concentration) at which about 50% of the tagging sequences hybridize to complementary molecular recognition sequences at equilibrium.

"Moderate stringency conditions" are selected to be about 5 to 10° C. below the thermal melting point (Tm) for the specific sequence at the ionic strength and pH of the hybridizing solution.

"High stringency conditions" are selected to be no more than about 5° C. below the thermal melting point (Tm) for the specific sequence at the ionic strength and pH of the hybridizing solution.

Figure 5:
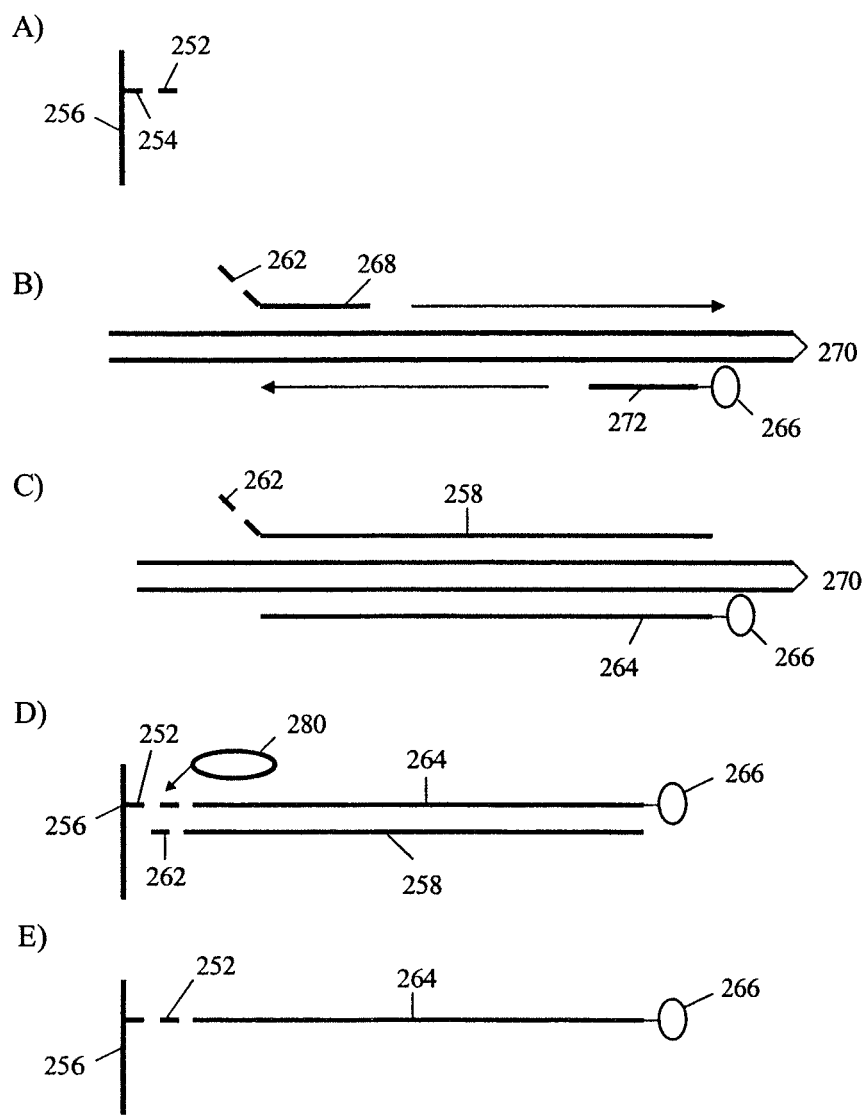
FIG. 5 illustrates steps in a third assay for an analyte-specific sequence, according to the invention.

In another assay illustrated in FIG. 5, two or more groups of capture oligonucleotides 252 are prepared and placed on a support 256, as illustrated at A of FIG. 5. Each group of capture oligonucleotides 252 includes a unique molecular recognition sequence 254. The molecular recognition sequence of each group includes at least one (and, typically, two or more) non-standard bases. A target oligonucleotide 258 and complementary oligonucleotide 264 can be formed by, for example, PCR amplification of an analyte containing the analyte-specific sequence or its complement. In PCR amplification, two different primers are used (as illustrated at B and C of FIG. 5). A first primer 268 contains a sequence complementary to a first sequence on a first strand of the analyte 270. A second primer 272 contains a sequence that is the complementary to a second sequence on a second strand of the analyte 270 which is upstream or downstream of the first sequence. The analyte-specific sequence typically includes the sequence of the analyte stretching between, and including, the sequences (or complements) to which the primers hybridize. The first primer 268 includes the tagging sequence 262 and the second primer 272 includes the reporter 266 (or a coupling agent for a reporter).

The target oligonucleotide 258 is typically brought into contact with the support 256 (or a container holding a particulate support) with associated capture oligonucleotides 252. Conditions are controlled to promote selective hybridization of the tagging sequence of the target oligonucleotide with a complementary molecular recognition sequence of a capture oligonucleotide, if an appropriate capture oligonucleotide is present on the support (as illustrated at D of FIG. 5). A reporter is also added (unless the complementary oligonucleotide 264 already contains the reporter) for coupling to the complementary oligonucleotide 264. Optionally, unincorporated primers can be removed prior to hybridization by techniques such as, for example, size exclusion chromatography, or after hybridization by, for example, washing.

An enzyme 280 is then provided to covalently couple the complementary oligonucleotide 264 to the capture oligonucleotide 252. Suitable enzymes include ligases. Optionally, the target oligonucleotide 258 is denatured from the complementary oligonucleotide 264 and the target oligonucleotide and other components of the assay are washed away leaving the complementary oligonucleotide 264 bound to the support 256, as illustrated at E of FIG. 5. The reporter 266 can then be detected.

Figure 6:
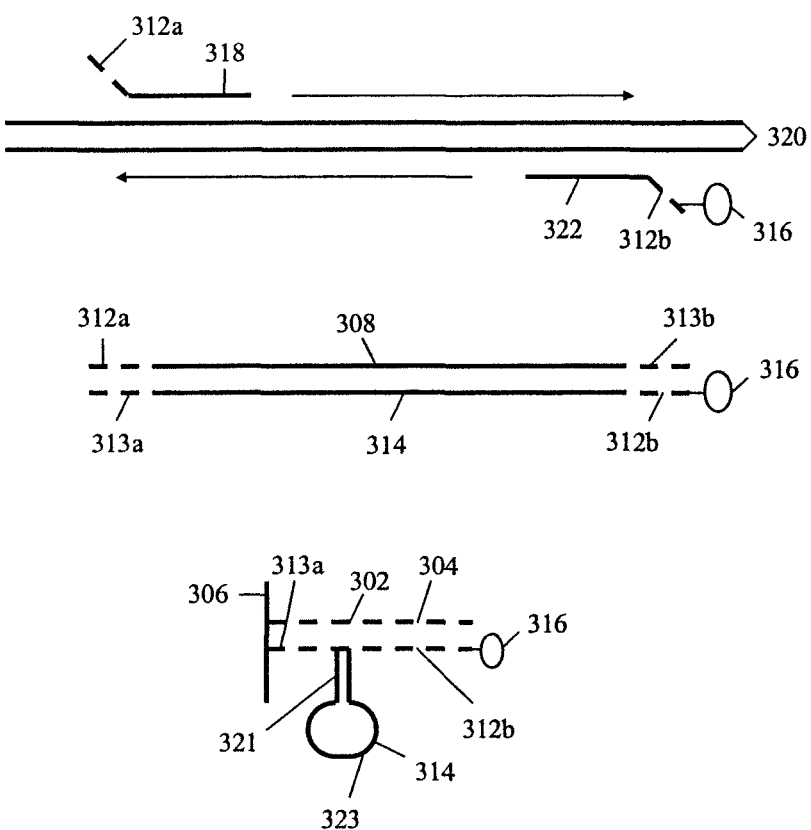
FIG. 6 illustrates steps in a fourth assay for an analyte-specific sequence, according to the invention.

In yet another assay illustrated in FIG. 6, the target oligonucleotide 314 forms a hairpin or stem-loop structure 321, 323 (or structure other than the typical double helix). In this assay, each of the first and second primers 318, 322 includes a portion of the tagging sequence 312b or a complement to a portion of the tagging sequence 312a. In addition, one of the primers 322 has a reporter 316 (or coupling agent for a reporter) attached to the portion of the tagging sequence 312b. Using, for example, PCR techniques, the first and second primers 318, 322 amplify the analyte 320 to produce a target oligonucleotide 314 and its complement 308. The tagging sequence 312b, 313a of the target oligonucleotide 314 is distributed at both ends of the target oligonucleotide.

The target oligonucleotide 314 is denatured from its complement 308 and brought into contact with the solid support 306 having capture oligonucleotides 302 with molecular recognition sequences 304. If the molecular recognition sequence 304 of one of the capture oligonucleotides is complementary to the tagging sequence 312b, 313a of the target oligonucleotide 314, the target oligonucleotide 314 will hybridize to that capture oligonucleotide. In some embodiments, the capture oligonucleotide is divided into two parts, each part complementary with one of the parts of the tagging sequence 312b, 313a. The two parts are coupled by a linker. The linker can be additional nucleotides or any other chemical linking moiety. The target sequence of the target oligonucleotide 314 forms at least part of a stem-loop structure 321, 323 (or structure other than an double helix). Detection is then performed as discussed above in the previous example.

Figure 7:
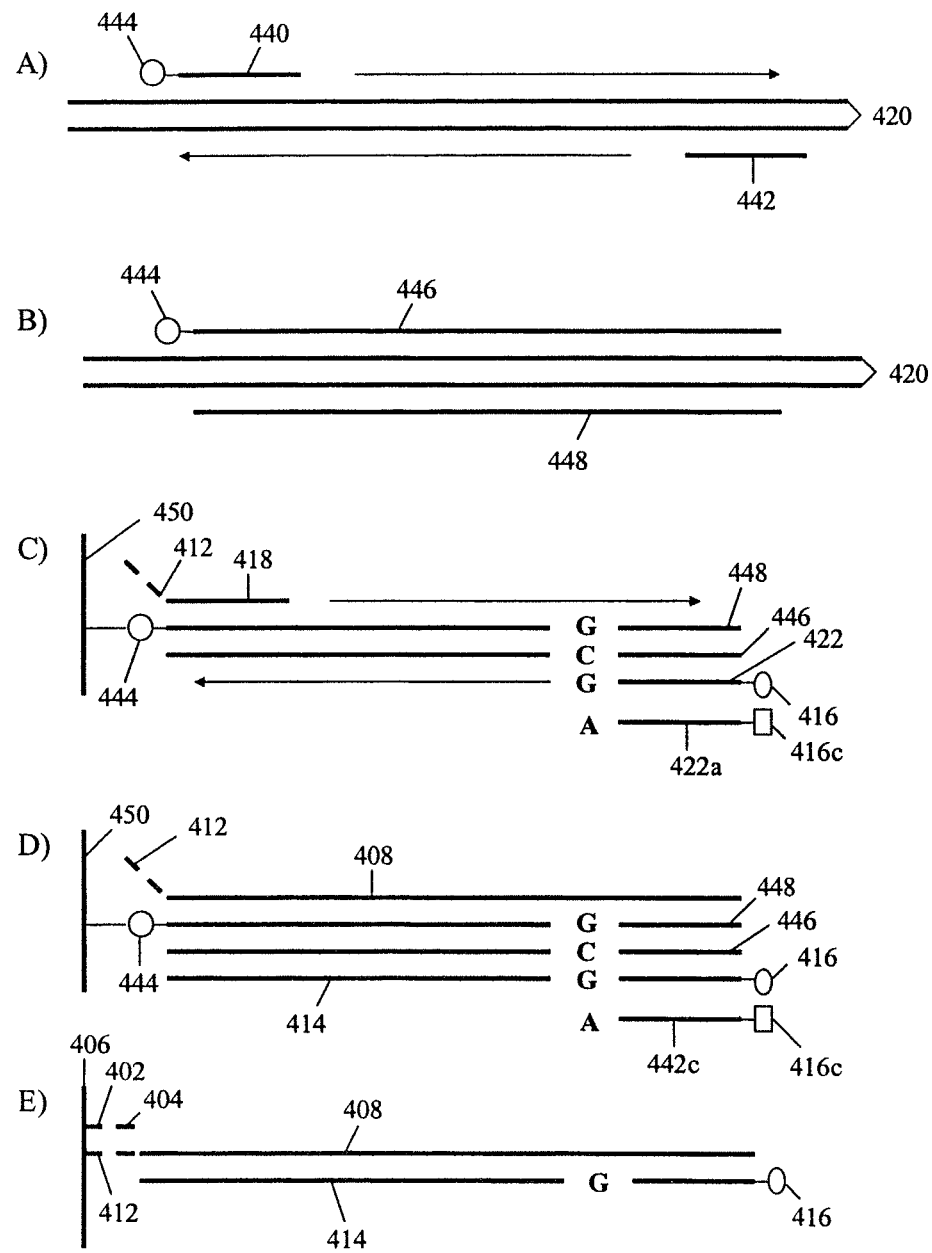
FIG. 7 illustrates steps in a fifth assay for an analyte-specific sequence, according to the invention.
Figure 8:
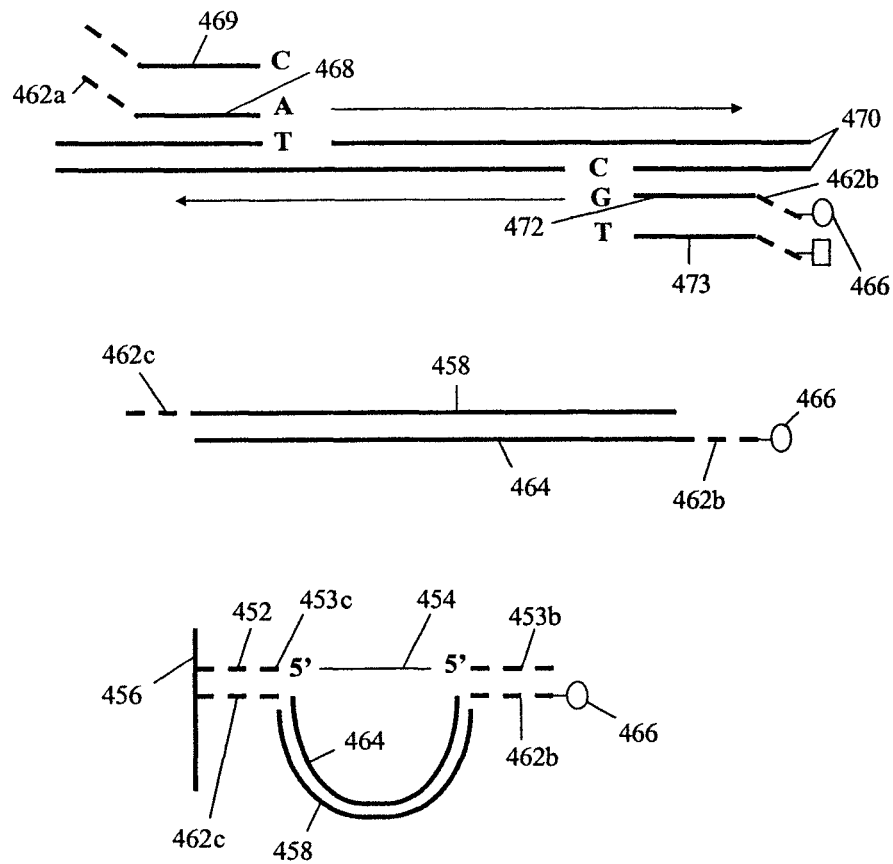
FIG. 8 illustrates steps in a sixth assay for an analyte-specific sequence, according to the invention.

In an alternative assay illustrated in FIG. 7, an analyte 420 is contacted by initial primers 440, 442 each having a sequence that is complementary to a sequence of the analyte 420, as illustrated at A of FIG. 7. One of the initial primers 440 also includes a coupling group 444 (e.g., biotin or a substituent containing a reactive functionality) for attachment to a substrate 450. The initial primers 440, 442 are extended using, for example, PCR techniques, as illustrated at B of FIG. 7. The extended initial primers 446, 448 each include the analyte-specific sequence or its complement.

The extended initial primers 446, 448 are then brought into contact with a substrate 450 that interacts with the coupling group 444 of extended initial primer 446 to attach the extended initial primer 446 to the substrate 450, as illustrated at C of FIG. 7. For example, the substrate can be coated with streptavidin and the extended initial primer include biotin.

Next, first and second primers 418, 422 are brought into contact with the extended initial primers 446, 448, as illustrated at C of FIG. 7. The first primer 418 has a tagging sequence 412 and the second primer 422 has a reporter 416 (or coupling agent for a reporter). Both primers also include a sequence complementary to a section of the extended initial primers 446, 448. The assay illustrated in FIG. 7 also shows that other primers 422a can be added. This is not a necessary feature of the assay, but is used to illustrate one embodiment of an assay for detecting alleles. The use of allele specific primers can be used in any of the other assays illustrated herein.

In the illustrated assay, primers 422, 422a are allele-specific primers with allele-specific reporters 416, 416a. In the illustrated example, the alleles differ by a single nucleotide, although it will be understood that other allele-specific assays with more than one nucleotide difference can be performed using these techniques. Primer 422 is extended because it is complementary to a sequence on the extended initial primer 446. Primer 422a does not extend because it is not complementary to extended initial primer 446. It will be recognized that an alternative assay includes several different allele-specific primers with allele-specific tagging sequences (as opposed to allele-specific reporters). It will also be recognized that another alternative assay includes non-allelic primers for determination of the presence of absence of non-allelic analyte-specific sequences in the analyte.

The primers 418, 422 are extended to form the target oligonucleotide 408 with the tagging sequence 412 and the complementary oligonucleotide 414 with the reporter 416 (or a coupling agent for a reporter). The target oligonucleotide 408 and complementary oligonucleotide 414 are denatured from the extended initial primers 446, 448 and brought into contact with capture oligonucleotides 402 on a solid support 406 (e.g., chip, wafer, or particles). The target oligonucleotide 414 hybridizes to a capture oligonucleotide 402 having a molecular recognition sequence 404 complementary to the tagging sequence 412. The presence or absence of particular analyte-specific sequences in the analyte is determined by observation of the presence or absence of reporter associated with each unique group of capture oligonucleotides.

In another example of an assay, a first primer 468 and a second primer 472 are brought into contact with an analyte 470 and extended to form a target oligonucleotide 458 and complementary oligonucleotide 464. In the illustrated example, the first and second primers 468, 472 are both allele-specific, but specific to different alleles. In addition to the first and second primers 468, 472, other first and second primers 469, 473 are included to amplify other alleles, if present in the sample.

The first primer 468 includes a first part 462a of a tagging sequence and the second primer 472 includes a second part 462b of the tagging sequence. One of the parts 462a, 462b includes a reporter 466 (or coupling agent for a reporter). Typically, the parts 462a, 462b of the tagging sequence will be configured so that the extension of the primers 468, 472 does not proceed through the tagging sequence. For example, the parts 462a, 462b can include a non-standard base as the base linking the part of the tagging sequence to the extendable portion of the primers 468, 472. In this embodiment, the nucleotide triphosphate of the complement of the non-standard base is not included in the PCR amplification process. Alternatively, a chemical linker can be used to couple the part of the tagging sequence to the extendable portion of the primer. Examples of suitable linkers include, but are not limited to, n-propyl, triethylene glycol, hexaethylene glycol, 1',2' dideoxyribose, 2'-O-methylriboneucleotides, deoxyisocytidine, or any linkage that would halt the polymerase.

A coupling oligonucleotide 452 is provided on a support 456. The coupling oligonucleotide 452 includes parts 453a, 453b that are complementary to the parts 462a, 462b of the tagging sequence. These parts 453a, 453b are coupled by a chemical or nucleotidic linker 454 that is capable of coupling 5' (or 3') ends of two nucleotidic sequences.

The target oligonucleotide 458 and complementary oligonucleotide 464 are brought in contact with the support 456 and capture oligonucleotide 452 to hybridize the corresponding parts 453a, 453b of the capture oligonucleotide with the respective parts 462a, 462b of the tagging sequence. The remainder of the target oligonucleotide 458 and complementary oligonucleotide 464 will typically form a structure such as that illustrated in FIG. 8.

Assays in which Non-standard Bases are Added by PCR Techniques

Although labeled natural nucleotide bases have many uses, there are shortcomings associated with labeled natural nucleotides. For example, site specific incorporation of a labeled natural nucleotide base is difficult to achieve. Generally, to label a position in an oligonucleotide which contains adenine, labeled adenosine triphosphate (dATP*) is added as a substrate to a reaction mix which includes an oligonucleotide template, dGTP, dCTP and dTTP, and a polymerase enzyme. If all dATP's in the reaction mix are labeled, all the adenine residues in the oligonucleotide sequence will be labeled. If a fraction of the dATP's in the reaction mix are labeled, adenine residues in random positions in the sequence are labeled. It is thus extremely difficult to label a single nucleotide residue in an oligonucleotide.

To overcome the problems associated with the incorporation of multiple labeled nucleotide residues, labeled dideoxyribonucleic acids have been used. Because the dideoxyribonucleic acid lacks a 3' hydroxyl group, the oligonucleotide is terminated at the position where the labeled dideoxyribonucleic acid is introduced. To determine the position of the labeled nucleotide, ladders are run to sequence the oligonucleotide. Because the oligonucleotide is terminated at the position where the dideoxyribonucleic acid is introduced, dideoxyribonucleic acids cannot generally be used in connection with amplification of the oligonucleotide strand.

Figure 9:
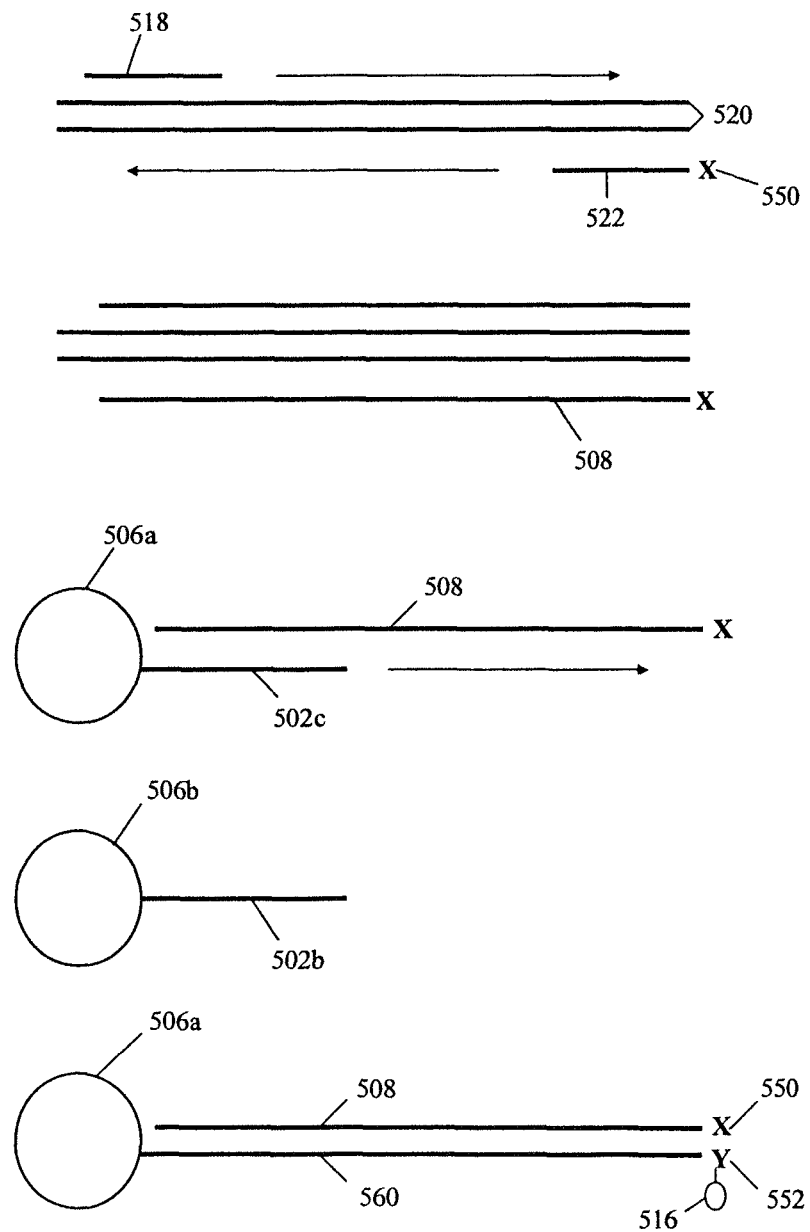
FIG. 9 illustrates steps in a seventh assay for an analyte-specific sequence, according to the invention.

FIG. 9 illustrates one type of assay, according to the invention, which includes the incorporation of a non-standard base by PCR. First and second primers 518, 522 are hybridized to analyte 520 and extended. One of the primers 522 includes a non-standard base 550 which, when extended, becomes the target oligonucleotide 508. Optionally, additional bases can be provided after the non-standard base 550. The target oligonucleotide 508 with the non-standard base 550 is then brought into contact with the solid support 506a, 506b that includes capture oligonucleotides 502a, 502b. The solid support illustrated in FIG. 9 is the particulate support discussed above, however, it will be recognized that a single solid support (e.g., a chip or wafer) could also be used.

The capture oligonucleotides 502a, 502b are different and are attached to different supports 506a, 506b, respectively, so that the capture oligonucleotide can be recognized by observing the unique property of the support to which it is attached. One capture oligonucleotide 502a hybridizes with the target oligonucleotide 508. The capture oligonucleotide 502a in this embodiment has a sequence that is complementary to at least a portion of the analyte-specific sequence of the target oligonucleotide 508.

After hybridization of the target oligonucleotide 508, the capture oligonucleotide 502a is extended in a PCR solution that includes dATP, dUTP, dGTP, dCTP, and the nucleotide triphosphate of a second non-standard base (e.g., diso-GTP) 552 complementary to the non-standard base 550 on the target oligonucleotide 508. The second non-standard base 552 is labeled with a reporter 516 (or coupling agent for a reporter). As the capture oligonucleotide is extended, the second non-standard base 552 with the reporter 516 is incorporated into the extended capture oligonucleotide opposite the non-standard base 550. Thus, the presence or absence of a reporter on a particular group of particulate supports indicates the presence or absence of a particular target oligonucleotide associated with the capture oligonucleotide.

Figure 10:
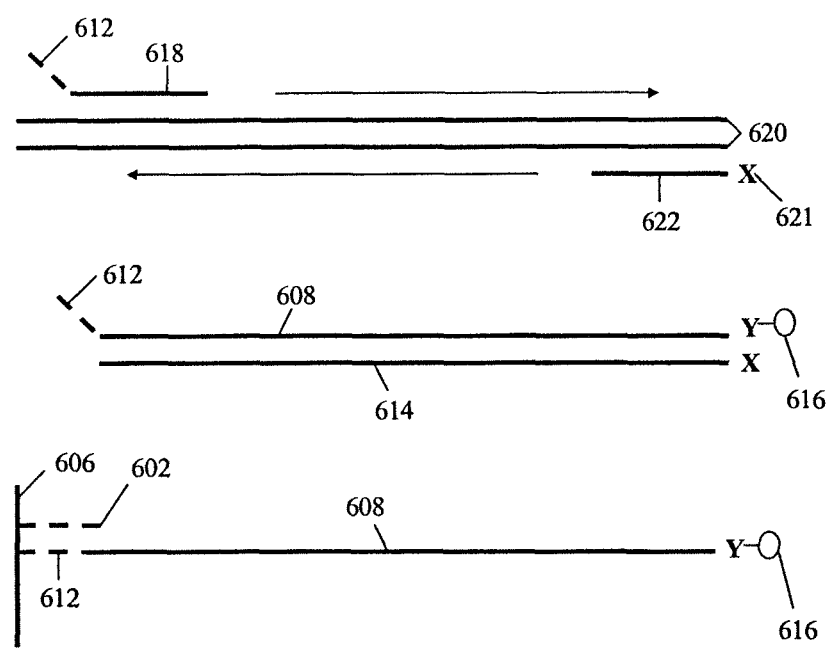
FIG. 10 illustrates steps in an eighth assay for an analyte-specific sequence, according to the invention.

FIG. 10 illustrates another assay. In this assay, the first primer 618 includes a tagging sequence 612 and the second primer 622 has a non-standard base 621 (or a sequence containing a non-standard base) at its 5' end. The primers 618, 622 amplify the analyte 620 in the presence of the dATP, dCTP, dGTP, dTTP, and the nucleotide triphosphate of the non-standard base complementary to non-standard base 621. This non-standard base nucleotide triphosphate is labeled with a reporter 616 (or coupling group for a reporter) and is incorporated opposite non-standard base 621 to form the target oligonucleotide 608.

The target oligonucleotide 608 is brought into contact with the solid support 606 having capture oligonucleotides 602 with molecular recognition sequences. If one of the molecular recognition sequences is complementary to the tagging sequence 612 of the target oligonucleotide 608, the target oligonucleotide 608 will hybridize to the capture oligonucleotide 602. Detection is then performed as discussed above in the previous examples.

Figure 11:
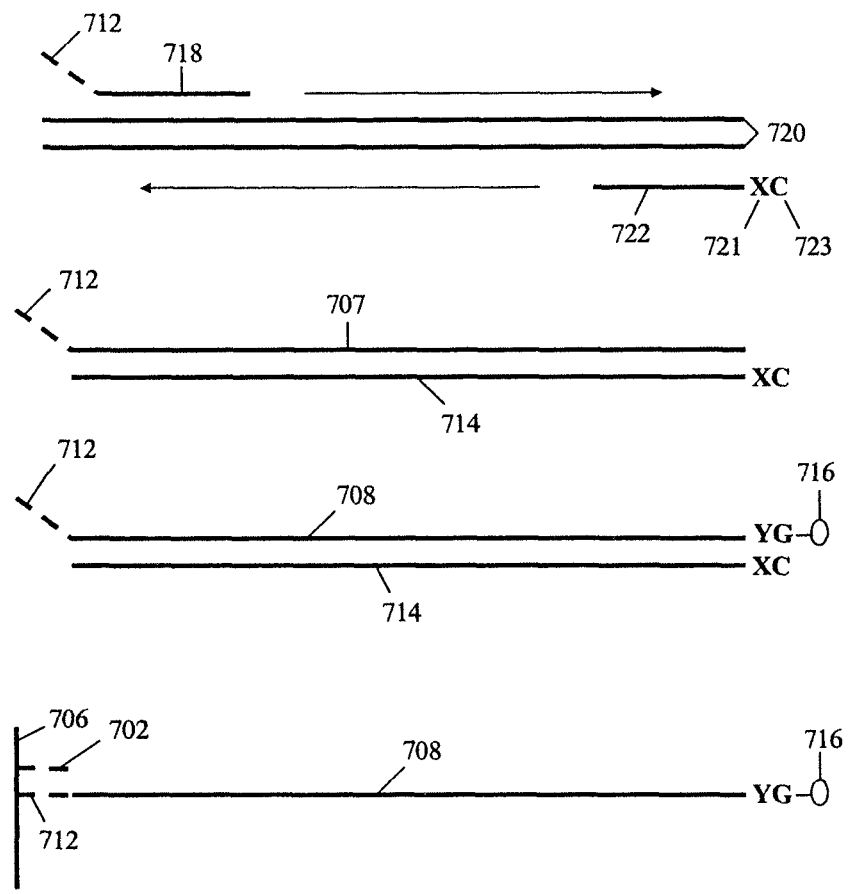
FIG. 11 illustrates steps in a ninth assay for an analyte-specific sequence, according to the invention.

FIG. 11 illustrates yet another assay. In this assay, the first primer 718 includes a tagging sequence 712 and the second primer 722 has a non-standard base 721 followed by a natural base 723 (or a sequence of natural bases) at its 5' end. The primers 718, 722 amplify the analyte 720 in the presence of the dATP, dCTP, dGTP, and dTTP only to form a partially extended target oligonucleotide 707 and its complement 714. The extension of the partially extended target oligonucleotide is limited by the non-standard base 721. After this initial amplification, the amplification products 707, 714 are washed to remove dATP, dCTP, dGTP, and dTTP.

A second extension step is then performed, in the presence of the triphosphate of the non-standard base complementary to non-standard base 721 and at least the triphosphate of the natural base complementary to natural base 723. This natural base triphosphate is labeled with a reporter 716 (or coupling group for a reporter) and is incorporated opposite natural base 723 to form the target oligonucleotide 708.

The target oligonucleotide 708 is brought into contact with the solid support 706 having capture oligonucleotides 702 with molecular recognition sequences. If one of the molecular recognition sequences is complementary to the tagging sequence 712 of the target oligonucleotide 708, the target oligonucleotide 708 will hybridize to the capture oligonucleotide 702. Detection is then performed as discussed above in the previous examples.

In one embodiment, allele-specific second primers are used with the same first primer. The allele-specific second primers are differentiated in the portion of the second primer that anneals to the analyte. A different natural base 723 is selected for each allele. During the second extension step, where bases are added opposite the non-standard base 721 and natural base 723, the nucleotide triphosphates of two or more natural bases are added to the extension mixture. The different nucleotide triphosphates are labeled with different reporters. Thus, if the natural base 723 can be A or C, depending on the allele, the dTTP and dGTP used in the extension step are labeled with different reporters. The identity of the reporter can be used to determine the presence of a particular, associated allele. Thus, for example, four different alleles can be simultaneously tested using this method and, with appropriate choice of reporters, can be indicated using four different colors.

Other Assays

Figure 16:
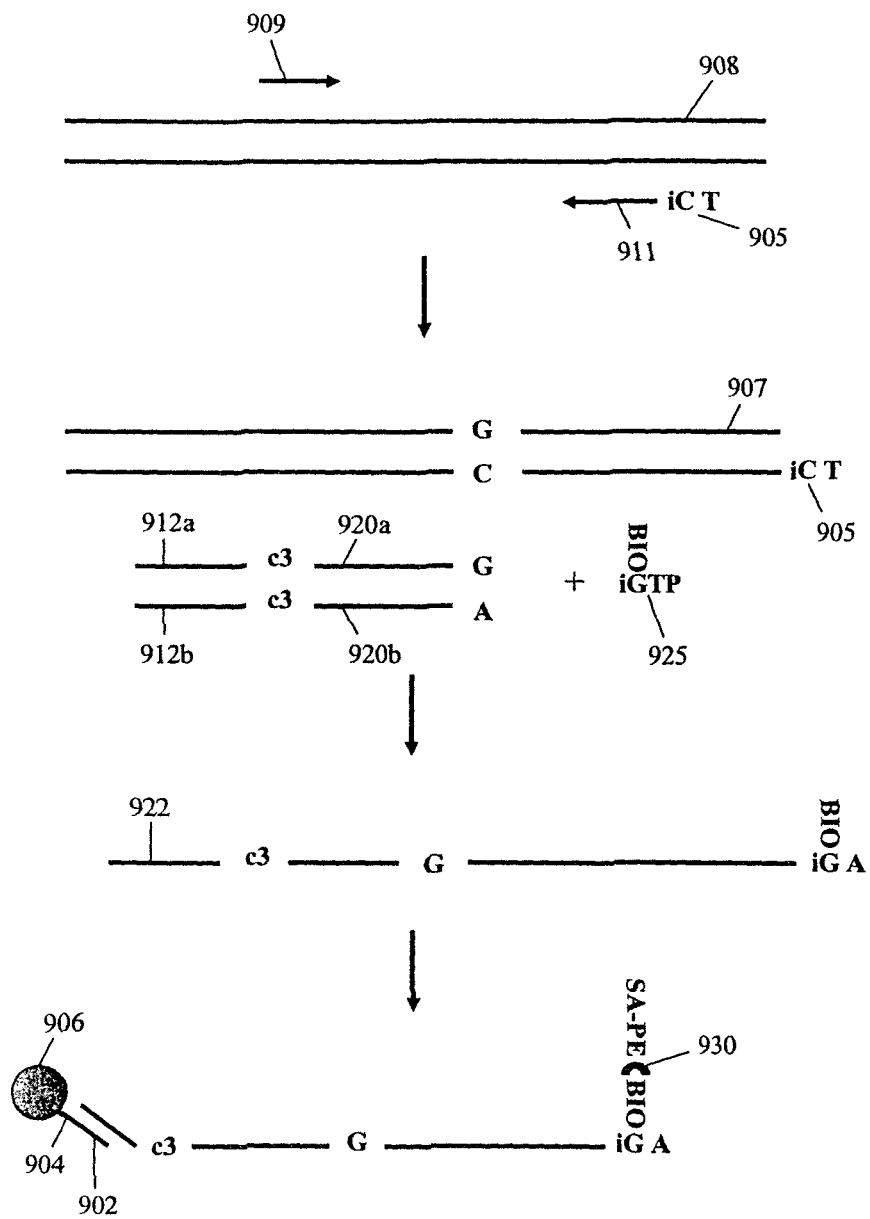
FIG. 16 illustrates steps in a tenth assay for an analyte-specific sequence, according to the invention.

In one assay illustrated in FIG. 16, two or more groups of capture oligonucleotides 902 are prepared. Each group of capture oligonucleotides 902 includes a unique molecular recognition sequence 904. The molecular recognition sequence of each group optionally includes at least one or more non-standard bases. The capture oligonucleotide also typically includes a reactive functional group for attachment to a solid support 906, although other attachment methods can be used, as described above.

In one embodiment, the support for the assay is a particulate support (e.g., beads). It will be understood that any of the assays described herein can be performed on a single solid support, on a particulate support, or any other support. The particulate support is divided into groups of particles, each group of particles having a characteristic (e.g., color, shape, size, density, or other chemical or physical property) that distinguishes that group of particles from other groups. Each group of capture oligonucleotides is coupled to one or more groups of particles. This produces an association of a particular group of particles with a particular group of capture oligonucleotides, allowing the determination of the capture oligonucleotide by observation of the unique particle support characteristic.

In another embodiment (not shown), the support for the assay can be, for example, a single solid support, such as, for example, a glass, metal, plastic, or inorganic chip. The capture oligonucleotides are disposed on the support and typically held by one of the methods described above (e.g., coupling via reactive groups on the capture oligonucleotide and support, use of a binding agent disposed on the support, or cross-linking of the capture oligonucleotides). Each of the groups is disposed in one or more unique regions of the solid support so that the region(s) can be associated with a particular capture oligonucleotide.

Returning to FIG. 16, the target oligonucleotide 908, if present in the assayed sample, is contacted with a first primer 909 and a second primer 911. The first and second primers 909, 911 can be allele-specific or, preferably, are not complementary to allele specific portions of the target oligonucleotide (i.e., the allele specific portions of interest are positioned within the target oligonucleotide between the regions that hybridize to the two primers). The second primer 911 also includes a non-complementary attachment region 905. This non-complementary reporter attachment region 905 optionally includes one or more non-standard bases. The target oligonucleotide 908 is amplified using the first and second primers 909, 911 and PCR techniques to obtain an amplification product 907 that includes the reporter attachment region 905.

The amplification product 907 is then contacted with allele specific primers 920a, 920b that are then extended, if the particular allele is present, using reaction conditions and reaction components similar to PCR to provide an allele specific extension product 922. Each allele specific primer 920a, 920b has an allele-specific tagging sequence 912a, 912b that is complementary to different molecular recognition sequences 904 and capture oligonucleotides 902. When extending the allele specific primers 920a, 920b, a labeled nucleotide 925 (or oligonucleotide) that is complementary to one or more bases of the attachment region 905 is provided. The labeled nucleotide 925 or oligonucleotide can include a reporter or a coupling agent, such as biotin, for attachment of a reporter.

After forming the extension product 922, contact is made with the capture oligonucleotides 902 and with a reporter 930 (unless a reporter was already attached). The capture oligonucleotide 902 and the support 906 identify which allele(s) is/are present in the sample and the reporter provides for detection of the extension product 922. For assays on particle supports, the particles can be separated according to the unique characteristics and then it is determined which particles 906 have a reporter coupled to the particle via the capture oligonucleotide 902 and extension product 922. Techniques for accomplishing the separation include, for example, flow cytometry. The presence of the reporter group indicates that the sample contains the allele associated with a particular allele-specific tagging sequence.

Selection of Molecular Recognition Sequences

When multiple molecular recognition sequences are used to form an assay system that can detect more than one analyte-specific sequence with application of a single sample, a collection of different molecular recognition sequences is typically needed. Preferably, the molecular recognition sequences are sufficiently different to permit reliable detection of analyte-specific sequences under a desired set of stringency conditions. A variety of different methods can be used to choose the collection of molecular recognition sequences. The following is a description of some methods and criteria that can be used. The methods and criteria can be used individually or in combinations.

The following are examples of criteria that can be used in creating a collection of molecular recognition sequences: the number of bases in the sequence, the number of non-standard bases in the sequence, the number of consecutive natural bases in the sequence, the number of consecutive bases (in either the forward or reverse directions) that are the same in any two sequences, specific required sequences (e.g., GC clamps at the 3' or 5' ends or both) and the estimated or actual melting temperature. One example of a method for determining Tm is described in Peyret et al., Biochemistry, 38, 3468-77 (1999), incorporated herein by reference. The non-standard bases can be estimated or accounted for using, for example, values for other bases (e.g., iso-G/iso-C can be estimated using G/C) or using experimental data such as that described below.

The following are a set of steps that can be used to form the collection of molecular recognition sequences:

1) Create a set of all possible oligonucleotides having a length of $n_1$ (e.g., 8, 9, or 10 nucleotides) using the natural bases and the desired non-standard bases (e.g., iso-C, iso-G, or both).

2) Optionally require that the oligonucleotides have a particular subsequence (e.g., GC clamps on the 3' or 5' ends or both ends).

3) Remove oligonucleotides without at least $n_2$ non-standard bases (e.g., without at least two iso-C bases) or with more than $n_3$ non-standard bases (e.g., with more than two iso-C bases) or both (e.g., accept only oligonucleotides with exactly two iso-C bases).

4) Optionally remove oligonucleotides with $n_4$ (e.g., four or five) natural bases in a row.

5) Select one of the remaining oligonucleotides and eliminate any of the remaining oligonucleotides that have $n_5$ bases (e.g., five or six bases) in the same order anywhere in the oligonucleotide sequence. Repeat for each non-eliminated oligonucleotide.

6) Optionally select one of the remaining oligonucleotides and determine its reverse complement (e.g., the reverse complement of "ACT" is "AGT"), then eliminate any of the other oligonucleotides that have $n_6$ consecutive bases (e.g., four or five bases) that are the same as a portion of the sequence of the reverse complement. Repeat for each non-eliminated oligonucleotide.

7) Optionally select only the remaining oligonucleotides that have an estimated or actual melting temperature (Tm) within a desired temperature range, above a desired temperature limit, or below a desired temperature limit For example, oligonucleotides can be eliminated that having a melting temperature below room temperature (about 22° C.).

EXAMPLES

Example 1

Cross-hybridization Analysis of Coding and Tagging Sequences

The equipment used in this analysis includes Luminex® 100 and Luminex® microbeads, DNA synthesizer (Northwestern Engineering, Inc.), Spectrophotometer for spot checking synthesis yields, thin layer chromatography (TLC) (SI250F TLC plate-silica gel, JTBaker) for oligonucleotide quality control, centrifuge, sonicator (Ney Dental), Vortex Genie (Vortex), and various pipettes (2, 20, 200, and 1000 µL).

A set of more than 100 oligonucleotides (molecular recognition sequences) and their complements (tagging sequences)

were designed and synthesized. The two sets of oligonucleotides contained non-standard (isoC and isoG)(EraGen Biosciences, Inc., Madison, Wis.) and natural (A, G, C, and T) (Perkin-Elmer/ABI) nucleotides and were 9 to 10 bases in length. The first set of the oligonucleotides was designated as molecular recognition sequences and labeled on the five prime end with an amino modifier (C6-TFA, Glen Research). The complement sets of oligonucleotides were designated the tagging sequence and labeled on the five prime end with Cy3 (Glen Research).

The following reagents were used in coupling the molecular recognition sequence to the unique Luminex beads: 0.1 mM pH4.5, 2-[N-morpholino]ethanesulfonic acid (MES) (Sigma).

1-ethyl-3-(3-dimethylaminopropyl) carbodiimide-HCl (EDC) (Pierce), 0.02% (v/v) Tween (Sigma), 0.1% (w/v) SDS (Sigma).

The hybridization step included a hybridization buffer Sourav 0.5 containing 10 mM Tris (Sigma), 1 mM EDTA (Sigma), 200 mM NaCl (Aldrich), 10 mM MgCl$_2$ (Aldrich), and 1% (w/v) PEG 8000 (Sigma).

Ninety-eight of the molecular recognition sequences were diluted to 1 nmol/μL in MES. Ninety-eight unique sets of Luminex® beads were prepared for coupling. The beads were sonicated for 20 seconds and vortexed for 10 seconds before being aliquoted. From the stock beads (1.25×10$^7$ beads/mL), 5 million beads were selected and placed in a 1.5 mL microcentrifuge tube. The beads were centrifuged at 10,000 rcf for 1 minute. The beads were then decanted, being careful not to disturb the beads. Finally, the beads were brought to 50 μL in MES, sonicated and vortexed. To couple the molecular recognition sequence to a distinct bead, 1 nmol of each molecular recognition sequence was added to one of the unique bead sets. Next, 1.75 μL of a fresh EDC (20 mg EDC/1 mL ddH2O) was added to the mixture, sonicated and vortexed. The mixture was then allowed to incubate at room temperature in the dark for 30 minutes, vortexing every 10 minutes. After 30 minutes, another 1.75 μL of a fresh EDC was added and incubated for 30 minutes, vortexing every 10 minutes.

After coupling, the beads were washed by adding 400 μL Tween-20, vortexed, centrifuged (10,000 rcf/1 min) and decanted. Next 400 μL SDS was added, centrifuged, decanted and finally brought up in 100 μL in MES and enumerated.

The complementary oligonucleotides (the tagging sequences) were quantified and qualified using TLC and polyacrylamide gel, and diluted to a final working concentration of 50 fmol/μL in MOPS.

After enumeration, the Luminex® bead/molecular recognition sequences were combined into a 98 bead set (1000 beads/bead region/well) for analysis. From the 98 bead set, a 50 bead set (2500 beads/bead region/well) was created. Table 1 includes the molecular recognition sequences for the 50 bead set and Table 2 includes the molecular recognition sequences for the 98 bead set.

To setup the cross hybridization experiment, 50 femtomoles of tagging sequences (1->98) were pipetted into wells in two 96 well plates (wells 1 and 2 were used for controls). Current limitations of the Luminex® 100, trimmed the dataset to 98 tagging sequences, with 2 controls for background subtraction (no tagging sequence).

The master mix of beads (98 mix), 10 μL/well, was then added to each well along with 31 μL of 2× Sourav 0.5 hybridization buffer and sufficient quantity of ddH2O, to give a final volume of 62 μL/well. The reagents were mixed well and allowed to incubate at room temperature for approximately 10 minutes. The samples were immediately analyzed by flow cytometry on the Luminex®100.

The 50 bead master mix was also run with its complementary molecular recognition sequences and tagging sequences, however the tagging sequences were at 500 fmol per well.

Figure 12:
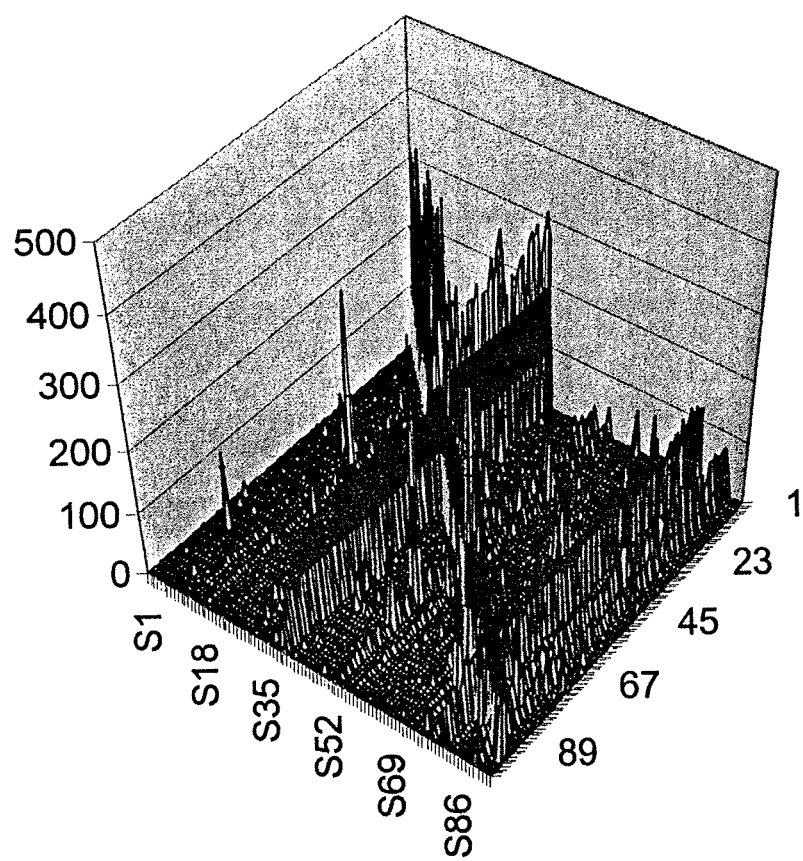
FIG. 12 is a 3D surface map illustrating, for 98 molecular recognition sequences (y-axis), the hybridization of complementary tagging sequences (x-axis) for each of the 100 molecular recognition sequences.
Figure 13:
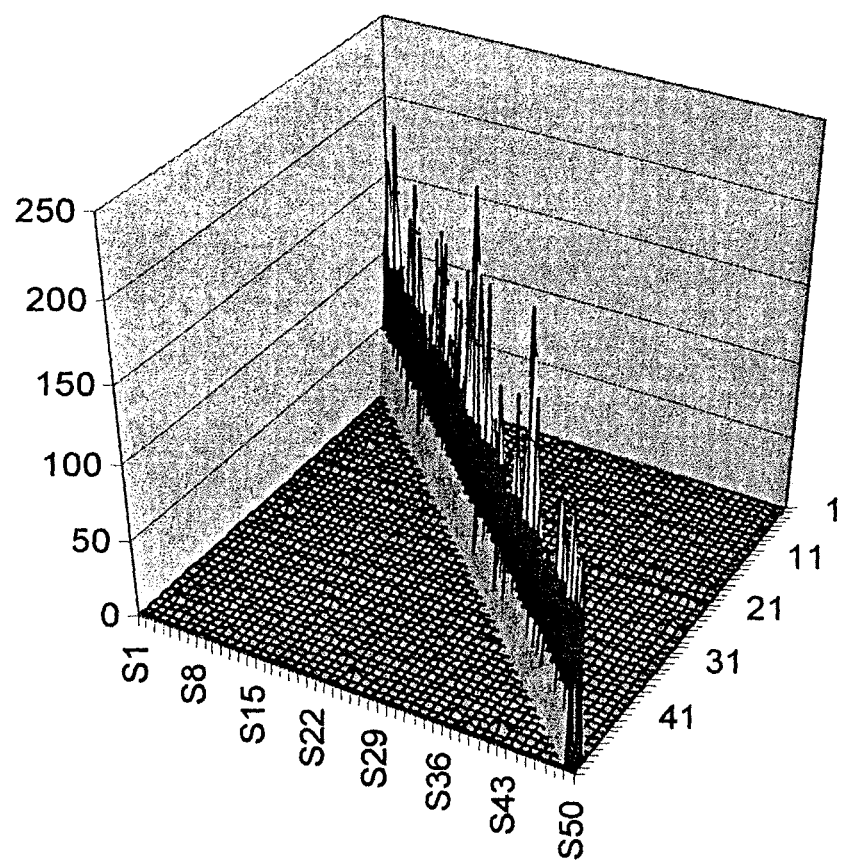
FIG. 13 is a 3D surface map illustrating, for 50 molecular recognition sequences (y-axis), the hybridization of complementary tagging sequences (x-axis) for each of the 50 molecular recognition sequences.

The resulting data is reported as Median Fluorescence Intensity (MFI) per bead for both sets. FIG. 12 shows the 3D surface map graphical results of the data collected in the 98 bead master mix experiment. The Y axis represents the molecular recognition sequence and the X axis represents the tagging sequence. FIG. 13 shows the 3D surface map graphical results of the data collected in the 50 bead master mix experiment.

TABLE 1

50 Bead Molecular recognition sequences (Y = iso-G and X = iso-C)

| Bead No. | Molecular recognition sequence | Seq Id No: |
|---|---|---|
| 1 | GAXGTXTGTC | 1 |
| 2 | CXGTTXTTCC | 2 |
| 3 | GGXTTGXTAG | 3 |
| 4 | C1TXGXTCTC | 4 |
| 5 | CXTCAXGAAC | 5 |
| 6 | GTAGXTAXGC | 6 |
| 7 | GGAXGXTAAC | 7 |
| 8 | CXGTATXGTG | 8 |
| 9 | CATXGGTAXG | 9 |
| 10 | GATTXTCGXC | 10 |
| 11 | GTTXAXGACC | 11 |
| 12 | CXGAAXGATC | 12 |
| 13 | CAAXTACGXC | 13 |
| 14 | CGGXATAXAC | 14 |
| 15 | GXAAAXXAGG | 15 |
| 16 | GTCXTAGXXC | 16 |
| 17 | GXCCTXTAXC | 17 |
| 18 | CCXACXTGAG | 18 |
| 19 | CTXXCAXAGG | 19 |
| 20 | GTXGAXATGC | 20 |
| 21 | GAAAXTGXXG | 21 |
| 22 | GCTGXAXATC | 22 |
| 23 | CGCAXATXAC | 23 |
| 24 | CTGGXTCXAG | 24 |
| 25 | GGAAXAXXCC | 25 |
| 26 | CXTCGCXTAC | 26 |
| 27 | GXCXAAAAXG | 27 |
| 28 | CXXGACXATC | 28 |
| 29 | CCATXAGXCC | 29 |
| 30 | GGCAXTXTGG | 30 |
| 31 | CTXAACXGGG | 31 |

TABLE 1-continued

50 Bead Molecular recognition sequences (Y = iso-G and X = iso-C)

| Bead No. | Molecular recognition sequence | Seq Id No: |
|---|---|---|
| 32 | GGAXACGXG | 32 |
| 33 | GCGXTTTAXG | 33 |
| 34 | GAGXAGXTXC | 34 |
| 35 | GXCTAAXCCG | 35 |
| 36 | GCXTGTXCAC | 36 |
| 37 | GXCAGAXTCG | 37 |
| 38 | CGTXCTAGXG | 38 |
| 39 | CGXXTAGTXG | 39 |
| 40 | CXAGGXAACC | 40 |
| 41 | CXAGAXGAXG | 41 |
| 42 | CGXTGXGTC | 42 |
| 43 | CAGXCGTXAG | 43 |
| 44 | GGCTXTGXAC | 44 |
| 45 | CCAGXGXAAG | 45 |
| 46 | GGCXAATXGC | 46 |
| 47 | GXCTGCXGG | 47 |
| 48 | GAXCTXCGGC | 48 |
| 49 | GTXCGAXGGG | 49 |
| 50 | GGXXATCCXG | 50 |

TABLE 2

98 Bead Molecular recognition sequences (Y = iso-G and X = iso-C)

| Bead No. | Molecular recognition sequence | Seq Id No: |
|---|---|---|
| 1 | GAXGTXTGTC | 1 |
| 2 | CXGTTXTTCC | 2 |
| 3 | GGXTTGXTAG | 3 |
| 4 | CTTXGXTCTC | 4 |
| 5 | CXTCAXGAAC | 5 |
| 6 | GXCTTCXATG | 51 |
| 7 | GTAGXTAXGC | 6 |
| 8 | GGAXGXTAAC | 7 |
| 9 | CXGTATXGTG | 8 |
| 10 | CATXGGTAXG | 9 |
| 11 | GATTXTCGXC | 10 |
| 12 | GTTXAXGACC | 11 |
| 13 | CXTCTTXXCC | 52 |
| 14 | CXGAAXGATC | 12 |
| 15 | CAAXTACGXC | 13 |
| 16 | CTCTXAXCCC | 53 |
| 17 | CTCXTGGTXC | 54 |
| 18 | CGGXATAXAC | 14 |
| 19 | GXAAAXXAGG | 15 |
| 20 | GTCXTAGXXC | 16 |
| 21 | GXCCTXTAXC | 17 |

TABLE 2-continued

98 Bead Molecular recognition sequences (Y = iso-G and X = iso-C)

| Bead No. | Molecular recognition sequence | Seq Id No: |
|---|---|---|
| 22 | CCXACXTGAG | 18 |
| 23 | CTXXCAXAGG | 19 |
| 24 | GXCAAAXCAC | 55 |
| 25 | GTXGAXATGC | 20 |
| 26 | GTTXGCXTTG | 56 |
| 27 | GAAAXTGXXG | 21 |
| 28 | GCTGXAXATC | 22 |
| 29 | CXCXTXCAAC | 57 |
| 30 | CTXXACAXXC | 58 |
| 31 | CXACTCXACC | 59 |
| 32 | GACXCAXXTG | 60 |
| 33 | CGCAXATXAC | 23 |
| 34 | CTCXCTXACG | 61 |
| 35 | CTGGXTCXAG | 24 |
| 36 | GGAAXAXXCC | 25 |
| 37 | GTGGXCTXTC | 62 |
| 38 | CXTCGCXTAC | 26 |
| 39 | CAXXACCXAG | 63 |
| 40 | GXCXAAAAXG | 27 |
| 41 | GTXCXAXACC | 64 |
| 42 | CXXGACXATC | 28 |
| 43 | CCATXAGXCC | 29 |
| 44 | CACXXTGXTC | 65 |
| 45 | GGCAXTXTGG | 30 |
| 46 | CTXAACXGGG | 31 |
| 47 | GXTCCTXGTC | 66 |
| 48 | GGAXACGXG | 32 |
| 49 | GCGXTTTAXG | 33 |
| 50 | CCXXATGTXG | 67 |
| 51 | GAGXAGXTXC | 34 |
| 52 | GXCTAAXCCG | 35 |
| 53 | GCXTGTXCAC | 36 |
| 54 | GXCAGAXTCG | 37 |
| 55 | CGTXCTAGXG | 38 |
| 56 | CGXXTAGTXG | 39 |
| 57 | CXAGGXAACC | 40 |
| 58 | GXGGTTXXTC | 68 |
| 59 | CXAGAXGAXG | 41 |
| 60 | CGXTGXGTC | 42 |
| 61 | CAGXCGTXAG | 43 |
| 62 | GGCTXTGXAC | 44 |
| 63 | CXCCGXAATC | 69 |
| 64 | GXXACXACAC | 70 |

TABLE 2-continued

98 Bead Molecular recognition sequences (Y = iso-G and X = iso-C)

| Bead No. | Molecular recognition sequence | Seq Id No: |
|---|---|---|
| 65 | GCXCXGTXC | 71 |
| 66 | GXCXGGAXC | 72 |
| 67 | CGAXAGCAXC | 73 |
| 68 | CCCAXTCCXC | 74 |
| 69 | GTXCCXXCAG | 75 |
| 70 | CXCCTAXCGG | 76 |
| 71 | GXGTTGXCG | 77 |
| 72 | CXAAGXAXCG | 78 |
| 73 | GGAGXCXXTC | 79 |
| 74 | CXGXAXGTAC | 80 |
| 75 | GXACGAXTXG | 81 |
| 76 | GXGCTXCATG | 82 |
| 77 | GTGXAGAGXG | 83 |
| 78 | GCCGXCXTC | 84 |
| 79 | CAAXCGXTCG | 85 |
| 80 | CACAXACXGC | 86 |
| 81 | CCAGXGXAAG | 45 |
| 82 | GGCXAATXGC | 46 |
| 83 | GXCTGCXGG | 47 |
| 84 | GXTGGXXCG | 87 |
| 85 | GCCXCCXGT | 88 |
| 86 | CXAXGGTCXC | 89 |
| 87 | CCXXGXGTG | 90 |
| 88 | GGXACXCCAG | 91 |
| 89 | GAXCTXCGGC | 48 |
| 90 | GCCTXCXGAC | 92 |
| 91 | GTXCGAXGGG | 49 |
| 92 | CXTTXCGCXC | 93 |
| 93 | GGXXATCCXG | 50 |
| 94 | CXCTAXGXXG | 94 |
| 95 | CXGCXAGXG | 95 |
| 96 | CXAGCXACGG | 96 |
| 97 | GACAXGCXCC | 97 |
| 98 | GGGXCGXXA | 98 |

Example 2

Preliminary Determination of Non-standard Base Contributions to the Nearest-Neighbor Parameters for Predicting Nucleic Acid Duplex Stability A Beckman DU-7500 spectrometer with temperature controller and sample carriage was utilized. Six samples can simultaneously be measured with precise temperature control. In order to cover a one hundred fold range of sample concentrations, quartz cuvettes of pathlengths 0.1 cm, 0.2 cm, 0.5 cm and 1.0 cm, were obtained from Hellma, USA. DNA were synthesized on a Model 392 DNA synthesizer from Perkin-Elmer/ABI. TLC Chromatography Tank (Fisher), and TLC plates (Si250F, JTBaker). A Savant SpeedVac was used for DNA prep, as are Sep-pak C-18 purification cartridges (Waters), UV lamp, a vortex, 10 cc syringes, and various pipetters (2, 20, 200, 1000 µL)

Oligonucleotides were synthesized from natural (A, G, C, and T) nucleotides (Perkin-Elmer/ABI) and isoC, and isoG (EraGen Biosciences, Inc., Madison, Wis.). The synthesized self-complementary and non-self-complementary sequences are in tables 3 and 4.

TABLE 3

Self-Complementary Sequences (isoC = X, isoG = Y)

| 3A | GGA CGT CC | Control |
| 3B | GGA YXT CC | Tandem isoC-isoG effect |
| 3C | GXA YXT YC | IsoC-isoG in penultimate position |
| 3D | GGA GCT CC | Control |
| 3E | GGA XYT CC | swapped tandem isoC-isoG effect |

TABLE 4

Non-Self-Complementary Sequences (isoC = X, isoG = Y)

| 4A | SEQ ID NO: 99 | 5' GCC AGT TTA A 3'<br>3' CGG TCA AAT T 5' | control |
| 4B | SEQ ID NO: 100 | 5' GCC AXT TTA A 3'<br>3' CGG TYA AAT T 5' | Single isoC-isoG in AT, TA context |
| 4C | SEQ ID NO: 101 | 5' GCX AGT TTA A 3'<br>3' CGY TCA AAT T 5' | Single isoC-isoG in mixed GC and AT context |
| 4D | SEQ ID NO: 102 | 5' GYC AGT TTA A 3'<br>3' CXG TCA AAT T 5' | Single isoC-isoG in mixed GC and CG context |
| 4E | SEQ ID NO: 103 | 5' GYY AGT TTA A 3'<br>3' CXX TCA AAT T 5' | Final tandem isoC-isoG substitution |

The following reagents were used in the purification of the oligonucleotides and melting experiments: TLC purification was performed by eluting for 5-6 hrs with n-propanol/ammonia/water (55:35:10 by volume) (Chou, S.-H., Flynn, P., and Reid, B. (1989) *Biochemistry* 28, 2422-2435, incorporated herein by reference). Hybridization experiments were carried out in degassed 1×SL Buffer (1.0M NaCl (Fisher), 10 mM sodium cacodylate (Fisher), 0.5 mM Na$_2$EDTA (Fisher), pH 7) (SantaLucia, J., Allawi, H., and Seneviratne, P. A., (1996) *Biochemistry* 35, 3555-3562, incorporated herein by reference).

Determination of thermodynamic parameters were obtained from melting curve data using Meltwin™ v3.0 as described in Petersheim, M., and Turner, D. H. (1983) *Biochemistry* 22, 253-263, incorporated herein by reference.

After synthesis the oligonucleotides were deprotected in ammonia at 50° C. overnight, lyophilized and purified by TLC by dissolving each sample in 175 µL ddH$_2$0 and eluting for 5-6 hours. The most intense, least mobile band was visualized, scraped from the plate, and eluted three times with 3 mL ddH$_2$0. The oligonucleotides were further desalted and purified with the Sep-pak™ columns by eluting with 30% acetonitrile, 10 mM ammonium bicarbonate, pH 7 (SantaLucia, J., Allawi, H., and Seneviratne, P. A., (1996) *Biochemistry* 35, 3555-3562), and finally dried in the SpeedVac™.

Self-complementary oligonucleotides were quantified and 2.0 OD$_{260}$ of each was collected and re-dried in the SpeedVac™. Oligonucleotides were then diluted in series to provide a one hundred fold dilution series in 1×SL Buffer. Absorbance vs. temperature profiles were measured with the Beckman DU-7500 spectrophotometer utilizing the various custom micro-cuvettes, sample carriage and temperature controller. See tables 5 and 6 for sample dilution series. The dilution series were prepared for each of the samples of Tables 3 and 4.

TABLE 5

Series A

| Sample | volume (µL) | Add(µL) | Place into cuvette(µL) |
|---|---|---|---|
| A1 | 0.0 | 94.5 | 34.5 |
| A2 | 57.5 | 40.2 | 34.5 |
| A3 | 63.2 | 44.3 | 34.5 |
| A4 | 73.0 | 51.2 | 69.0 |
| A5 | 55.2 | 38.5 | 69.0 |

After running samples A1-A5 the dilutions for the second series were assembled. For Series B, the remaining 24.7 µL from the last sample was combined with the dilutions in cuvettes A-3, A-4 and A-5 (~172.5 µL total) and an additional 345 µL of 1×SL Buffer.

TABLE 6

Series B

| Sample | volume (µL) | Add(µL) | Place into cuvette(µL) |
|---|---|---|---|
| B1 | 542.2 | 0.0 | 172.5 |
| B2 | 369.8 | 230.0 | 172.5 |
| B3 | 427.2 | 270.0 | 345.0 |
| B4 | 352.5 | 224.0 | 345.0 |
| B5 | 231.5 | 132.2 | 345.0 |

The volumes placed in the cuvettes leaving approximately 4% head space in each cuvette for thermoexpansion of the samples during the melts.

For each run the samples were further degassed and then annealed by raising the temperature to 85° C. for five minutes, and then cooled to 10° C. over five more minutes. To limit condensation, a blanket of dry argon was utilized at low temperatures. For series A and B, measurements were taken at 260 nm and 280 nm, simultaneously. Samples were heated at a constant rate from 10° C. to 90° C. at 1.0° C./min.

The data collected from the melting experiment were then analyzed with the Meltwin™ software by curve fit analysis of $Tm^{-1}$ vs $\ln(C_T)$, where $C_T$ is the total strand concentration and $Tm^{-1}$ is the reciprocal melting temperature (Borer, P. N., Dengler, B., Tinoco, I., Jr., and Uhlenbeck, O. C. (1974) *J. Mol. Biol.* 86, 843-853, incorporated herein by reference).

Non-self-complementary oligonucleotides were combined in equal molar amounts to 2.0 OD$_{260}$ (optical density at 260 nm) and diluted in the same manner as the self-complementary oligonucleotides dilution series in Tables 5 and 6. Similar melt data was collected and analyzed with Meltwin™ for the non-self-complementary oligonucleotides.

The resulting thermodynamic parameters determined by Meltwin™ for the self-complementary and non-self-complementary oligonucleotides are summarized in Tables 7 and 8.

TABLE 7

Self-Complementary Sequences Thermodynamic Data (isoC = X, isoG = Y)

| | | $-\Delta G_{37}$ (kcal/mol) | $-\Delta H$ (kcal/mol) | $-\Delta S$ (cal/K·mol) | $T_M$ (° C.) 1.0e-4M |
|---|---|---|---|---|---|
| 1A | GGA CGT CC | 8.27 | 53.5 | 145.9 | 52.8 |
| 1B | GGA YXT CC | 9.41 | 57.62 | 155.4 | 58.5 |
| 1C | GXA CGT YC | 10.89 | 66.27 | 178.6 | 63.5 |
| 1D | GGA GCT CC | 8.10 | 51.04 | 138.5 | 52.4 |
| 1E | GGA XYT CC | 9.70 | 57.77 | 155.0 | 60.2 |

TABLE 8

Non-Self-Complementary Sequences Thermodynamic Data (isoC = X, isoG = Y)

| | | | $-\Delta G_{37}$ (kcal/mol) | $-\Delta H$ (kcal/mol) | $-\Delta S$ (cal/K·mol) | $T_M$ (° C.) 1.0e-4M |
|---|---|---|---|---|---|---|
| 4A | SEQ ID NO: 99 | 5' GCC AGT TTA A 3'<br>3' CGG TCA AAT T 5' | 8.43 | 69.22 | 196.0 | 45.8 |

TABLE 8-continued

Non-Self-Complementary Sequences
Thermodynamic Data (isoC = X, isoG = Y)

|   |   |    |                    | $-\Delta G_{37}$ (kcal/mol) | $-\Delta H$ (kcal/mol) | $-\Delta S$ (cal/K·mol) | $T_M$(° C.) 1.0e-4M |
|---|---|----|--------------------|---------|---------|---------|---------|
| 4B | SEQ ID NO: 100 | 5' 3' | GCC AXT TTA A 3'<br>CGG TYA AAT T 5' | 9.56 | 56.66 | 151.9 | 54.5 |
| 4C | SEQ ID NO: 101 | 5' 3' | GCY AGT TTA A 3'<br>CGX TCA AAT T 5' | 9.36 | 62.98 | 172.9 | 51.6 |
| 4D | SEQ ID NO: 102 | 5' 3' | GYC AGT TTA A 3'<br>CXG TCA AAT T 5' | 9.62 | 54.30 | 144.1 | 55.7 |
| 4E | SEQ ID NO: 103 | 5' 3' | GYY AGT TTA A 3'<br>CXX TCA AAT T 5' | 10.59 | 70.19 | 192.2 | 56.0 |

All samples have concentration dependant $T_M$s and monophasic melting transitions. IsoC and isoG contributions to duplex formation appear to be substantial, adding up to an additional 5° C. (Sample 3B and 4C) per isoC/isoG pair to 10° C. (Sample 3C and 4E) compared to natural (A, G, C, and T) Watson-Crick oligonucleotides.

Tables 7 and 8 show some the extent of the nearest-neighbor effects that are occurring when AEGIS bases are mixed with natural DNA.

Example 3 and Comparative Example

Site Gated Incorporation

```
First primer
                                    (SEQ ID NO: 154)
5'AGAACCCTTTCCTCTTCC Target
                                    (SEQ ID NO: 155)
5'AAGAACCCTTTCCTCTTCCGATGCAGGATACTTAACAATAAATATTT Second Primer
                                    (SEQ ID NO: 156)
CTACGTCCTATGAATTGTTATTTATAAAXAGGACAGACG 5'
```

X=isoCTP

The sequences of the first primer, target, and second primer are shown in SEQ ID NO:154, SEQ ID NO:155, and SEQ ID NO:156, respectively.

PCR was performed using the following mixture: 0.2 µM first primer, 0.2 µM second primer, 50 fM target, 50 µM each dGTP, dATP, dTTP and dCTP, 10 mM Tris pH 8, 0.1% BSA, 0.1% Triton X-100, 0.1 µg/µl degraded herring sperm DNA, 40 mM KAc, 2 mM $MgCl_2$, 1 U Amplitaq Stoffel (Perkin Elmer Biosciences, Foster City, Calif.) in a 20 µl reaction volume. The mixture was held for 2 minutes at 95° C. Then was cycled 30 times between 95° C. with a 1 second hold and 58° C. with a 10 second hold. Finally, the mixture was held for 2 minutes at 58° C.

Two PCR reaction mixtures were prepared. Each PCR reaction mixture was desalted using an AutoSeg™ G-50 microspin column (Amersham Pharmacia Biotech Inc., Piscataway, N.J.) to remove unincorporated dNTP's, the column buffer had been exchanged for $ddH_2O$ prior to desalting the sample. The desalted samples were adjusted to these final concentrations for the following reaction components: 10 mM Tris pH 8, 0.1% BSA, 0.1% Triton X-100, 0.1 µg/µl degraded herring sperm DNA, 40 mM KAc, 2 mM $MgCl_2$, 1 U/reaction Amplitaq Stoffel (Perkin Elmer Biosciences, Foster City, Calif.), and 10 µM Cy3-dTTP (NEN Life Science Products, Inc., Boston, Mass.) in a 25 µl reaction volume. In addition, disoGTP was added in the following concentrations: 0 µM (Comparative Example) or 40 µM (Example 3). The reaction mixtures were incubated at 68° C. for 15 minutes, and 5 µl of the resulting reactions were examined by electrophoresis on a 10% denaturing polyacrylamide gel. The gel was imaged for Cy3 containing extension products using a 595 Fluorimager (Molecular Dynamics, Sunnyvale, Calif.).

The results (data not shown) indicated that there was no additional extension of the first primer during the final PCR step when disoGTP was not present (i.e., there was little or no misincorporation of bases opposite the iso-C of the second primer).

Example 4

Synthesis of Labeled deoxyisoGuanosine 5'-Triphosphates

For the following chemical reactions, tributylammonium pyrophosphate was purchased from Sigma; biotin N-hydroxysuccinimide ester, was purchased from Pierce Chemical Company; all other chemicals were purchased from Aldrich Chemical Co. or Fisher Chemical Co. and were used without further purification. Solvents were dried over 4 Å molecular sieves. Reactions were carried out under dry argon in oven-dry glassware. Column chromatography was performed with silica gel (230-425 mesh).

Abbreviations:
$Ac_2O$ Acetic anhydride
DMF N,N-Dimethylformamide
DMAP 4,4'-Dimethylaminopyridine
DMT 4,4'-Dimethoxytrityl
$Et_3N$ Triethylamine
MeCN Acetonitrile
MeOH Methyl alcohol
Tol p-Toluyl 1-(p,p'-Dimethoxytrityl)-hexamethylenediamine (2)

Hexamethylenediamine (10 eq., 375 mmol, 43.5 g) was coevaporated two times from pyridine and dissolved in 100 ml pyridine. DMAP (0.1 eq., 3.75 mmol, 457 mg) was added and the reaction flask placed in an ice bath. DMT-chloride (1 eq., 37.5 mmol, 12.69 g), dissolved in 100 ml pyridine, was added dropwise over 2 h. It was stirred at room temperature for 4 h, MeOH (5 ml) added, the reaction mixture concentrated and the remaining residue extracted with aqueous NaHCO$_3$/ethyl acetate. The organic layer was washed twice with aqueous NaHCO$_3$ solution, dried and the solvent evaporated. The obtained product was used in next step without further purification.

Yield: 14.895 g (35.634 mmol, 95%) sticky oil.

2-Chloro-6-(6-p,p'-dimethoxytritylaminohexyl)-aminopurine-2'-deoxy-3',5'-ditoluoylriboside (3)

Compound 2 (1.3 equiv., 31.916 mmol, 13.34 g) was coevaporated with DMF and dissolved in 100 ml DMF. Diisopropylethylamine (3.9 equiv., 95.748 mmol, 16.65 ml) and compound 1 (1 equiv., 24.551 mmol, 13.282 g), dissolved in 100 ml DMF, were added and it was stirred at room temperature for 3 h. It was concentrated, the residue extracted with aqueous NaHCO$_3$/ethyl acetate, the organic layer dried and the solvent evaporated. The residue was triturated with ether twice and the obtained solid product used further after drying in vacuum without further purification.

2-Benzyloxy-6-(6-p,p'-dimethoxytritylaminohexyl)-aminopurine-2'-deoxyriboside (4)

Compound 3 (1 equiv., 19.23 mmol, 17.74 g) was dissolved in DMF (25 ml) and added to a solution of NaH (10 eq., 192.3 mmol, 7.69 g of a 60% dispersion in mineral oil) in benzylalcohol (128 mL). The reaction mixture was heated (120° C., 6 h) and then stirred at room temperature (15 h) before filtrated over Celite, the filtrate evaporated, the residue extracted (ethyl acetate/water), the organic layer washed (NaHCO$_3$-solution), dried, the solvent evaporated and the residue triturated 5 times with ether/hexane 1:10. TLC: CHCl$_3$/10% MeOH R$_F$=0.26.

Yield: 10.280 g (13.562 mmol, 70.5% for 2 steps) foam.

2-Benzyloxy-6-(6-p,p'-dimethoxytritylaminohexyl)-aminopurine-2'-deoxy-5'-O-p,p'-dimethoxytritylriboside (5)

Compound 4 (14.7388 mmol, 11.172 g) was coevaporated with pyridine, dissolved in 150 ml pyridine and DMAP (0.25 equiv., 3.6847 mmol, 450 mg) added. The flask was placed in an ice bath and DMTCl (1.5 equiv., 22.108 mmol, 7.484 g) was added slowly over 2 h. It was stirred at room temperature for 22 h, then MeOH (1 ml) added, the reaction mixture concentrated and the residue extracted (chloroform/aqueous NaHCO$_3$). The organic layer was dried, the solvent evaporated and the residue triturated with ether/hexane 1:1 to remove the excess DMT and the insoluble solid product was dried and used further without additional purification.

Yield: 14.890 g (14.047 mmol, 95%) light brown foam.

2-Benzyloxy-6-(6-p,p'-dimethoxytritylaminohexyl)-aminopurine-3'-O-acetyl-2'-deoxy-5'-O-p,p'-dimethoxytritylriboside (6)

Compound 5 (14.047 mmol, 14.89 g) was coevaporated with pyridine, dissolved in 200 ml pyridine and DMAP (0.25 equiv., 3.5117 mmol, 428 mg), Et$_3$N (5 equiv., 70.235 mmol, 9.7 ml) and Ac$_2$O (2.5 equiv., 35.1175 mmol, 3.582 g) were added. It was stirred at room temperature for 4.5 h, then MeOH (2 ml) added, the reaction mixture concentrated and the residue extracted (ethyl acetate/aqueous NaHCO$_3$). The organic layer was dried, the solvent evaporated and the residue purified by column chromatography using an one step gradient of ethyl acetate/hexane/Et$_3$N 30:60:1, then 65:35:3. Yield: 5.93 g (5.385 mmol, 38%), yellow foam.

2-Benzyloxy-6-(6-aminohexyl)-aminopurine-3'-O-acetyl-2'-deoxyriboside (7)

Compound 6 (2.471 mmol, 2.723 g) was dissolved in 50 ml acetonitrile/2 ml water and Ce(NH$_4$)$_2$(NO$_3$)$_3$ (0.3 equiv., 0.74 mmol, 406 mg) was added. It was refluxed for 45 min., then another 0.15 equiv. Ce(NH$_4$)$_2$(NO$_3$)$_3$ (0.37 mmol, 205 mg) added and refluxing continued for 1 h. Then, it was evaporated, the residue triturated with ether to remove the DMT, the insoluble product dried and used further without additional purification.

2-Benzyloxy-6-(6-trifluoroacetamidohexyl)-aminopurine-3'-O-acetyl-2'-deoxyriboside (8)

The above obtained compound 7 (max. 5.385 mmol) was dissolved in 30 ml MeOH/50 ml ethyl trifluoroacetate/5 ml Et$_3$N and the reaction mixture stirred at room temperature for 21.5 h. TLC (chloroform/17.5 MeOH): R$_F$=0.72) indicated complete conversion. It was evaporated, the residue extracted (brine/ethyl acetate), the organic layer dried, the solvent evaporated and the residue purified by silica gel column chromatography using a one step gradient of chloroform/1.5% MeOH, then 17.5% MeOH. Yield: 2.80 g (4.714 mmol, 87%) foam.

2-Benzyloxy-6-(6-trifluoroacetamidohexyl)-aminopurine-3'-O-acetyl-5'-triphosphoryl-2'-deoxyriboside (9)

Imidazole (61 eq., 306 mg, 4.5 mmol, recrystallised) was dissolved in acetonitrile (3.6 mL) and chilled (0° C.). POCl$_3$ (19 eq., 0.128 mL) and triethylamine (61 eq., 0.633 mL) were then added and the mixture was stirred (0° C., 0.5 h) before adding a portion (0.309 mL) to 8 (1 eq., 0.074 mmol, 44 mg). This mixture was stirred (r.t., 0.5 h) before adding DMF (1.5 mL) containing tributylammonium pyrophosphate (2 eq., 0.16 mmol, 73 mg). The reaction was then quenched (2 mL, 10% NH$_4$COO) 24 h later and lyophillized. Product was purified by anion-exchange chromatography (Dionex ProPac SAX-10) using 20% MeCN and a gradient of (NH$_4$)$_2$CO$_3$/20% MeCN. Collected product was repetitively lyophilized to remove excess salt. Yield 0.007 mmol (10%), white solid.

6-(6-aminohexyl)-aminopurine-5'-triphosphoryl-2'-deoxyriboside (10)

Compound 9 (0.007 mmol) was dissolved in methanol (2.5 mL) before adding Pd/C (10%, 5 mg) and NH$_4$COO (0.05 mmol, 31 mg). The suspension was refluxed (1 h) before filtering off the catalyst and evaporating the solvent. The residue was then treated with 28% ammonium hydroxide (1.5 mL, 3 h, room temp.) before the reaction was dried and the product purified by anion-exchange chromatography (Dionex ProPac SAX-10) using 20% MeCN and a gradient of (NH$_4$)$_2$CO$_3$/20% MeCN. Collected product was repetitively lyophilized to remove excess salt. Yield 0.0063 mmol (90%), white solid.

6-(6-biotinylamidohexyl)-aminopurine-5'-triphosphoryl-2'-deoxyriboside (11)

To 10 (0.88 µmol, triethylammonium salt) in H$_2$O (40 µL) was added sodium borate (10.5 µL, 1M, pH 8.5) followed by DMF (216 µL) containing biotin N-hydroxysuccinimide ester (2.6 µmmol, 3 eq.). The reaction proceeded (3 h, 55° C.) before it was diluted with 20% MeCN and the product purified by anion-exchange chromatography (Dionex ProPac SAX-10) using H₂O and a gradient of an NH₄HCO₃ solution. Yields approximately 70%.
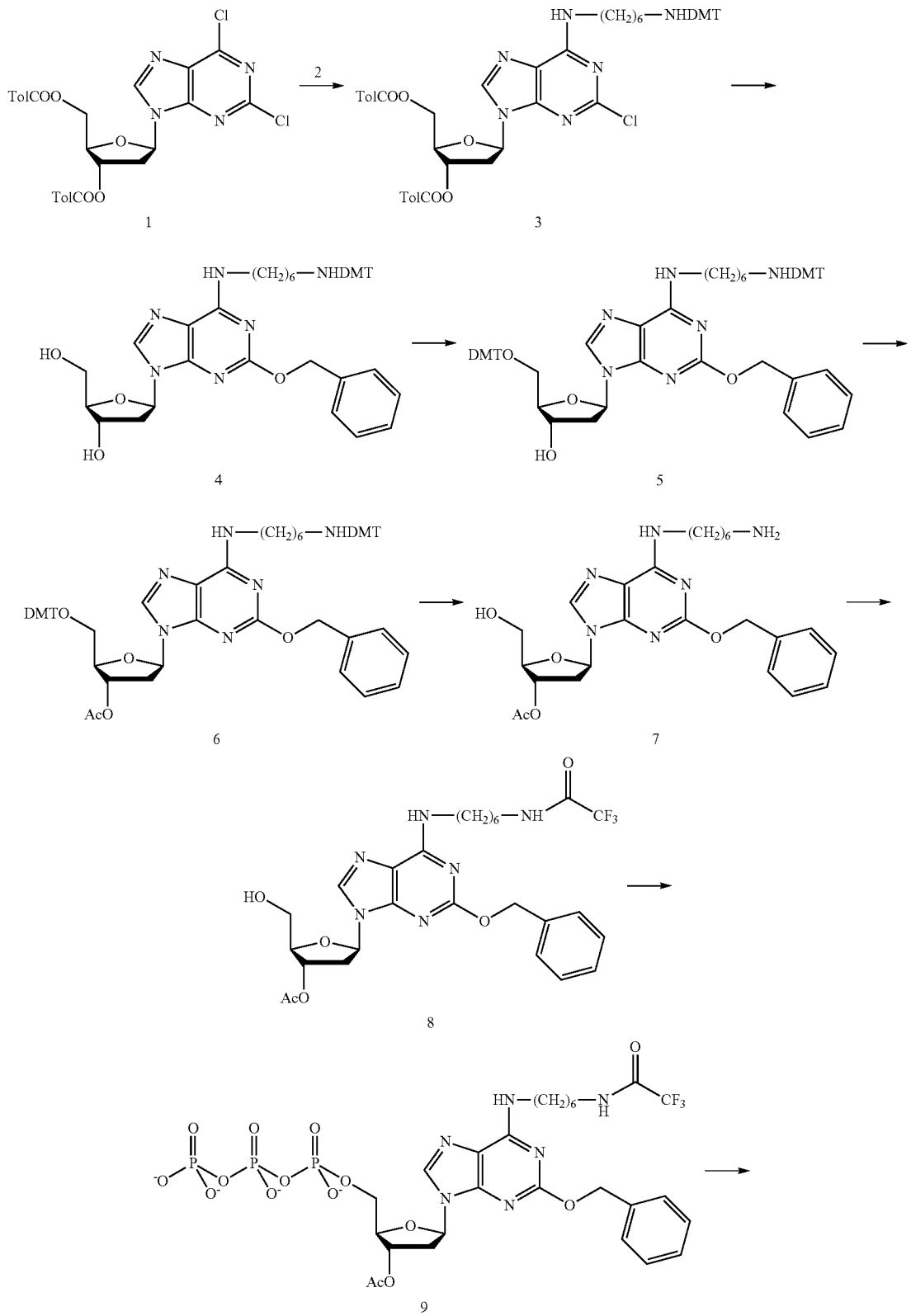

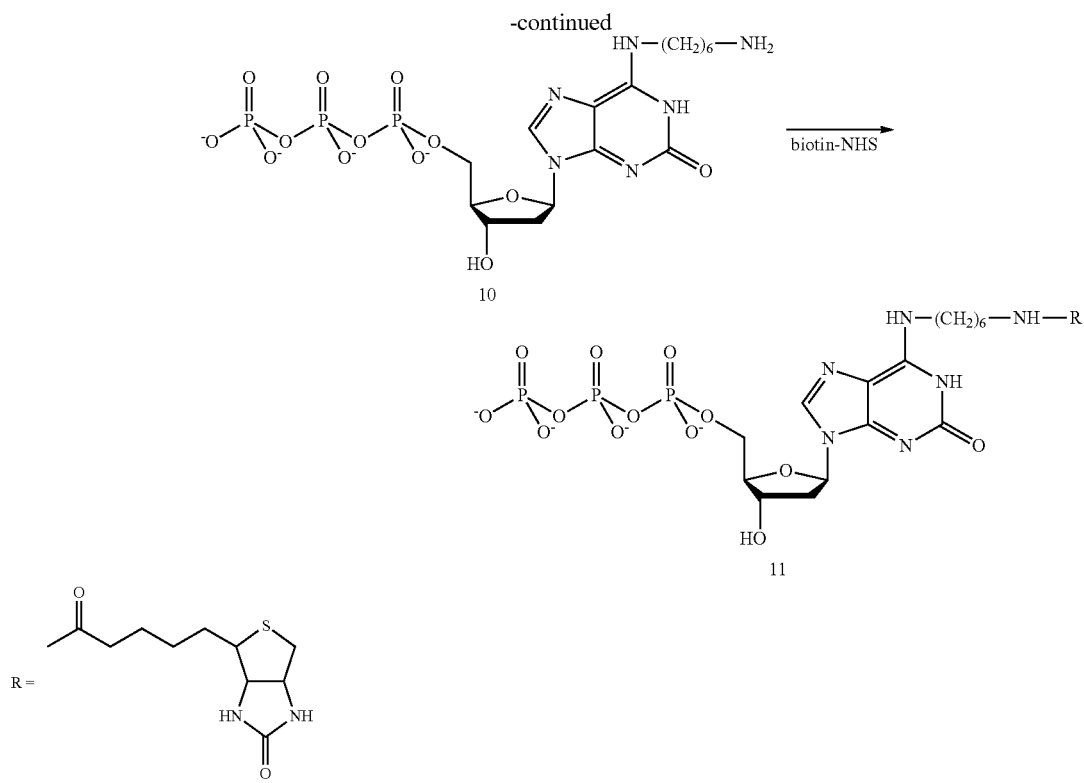

Example 5

Multiplexed Genotyping of Genomic DNA Using Incorporation of a Labeled Base and Capture on Solid Support Microspheres The genotypes of nine polymorphic loci were determined following the amplification, query, and capture of targeted nucleic acid sequences from genomic DNA samples. The first step, a multiplex PCR reaction, included a multiplexed set of paired PCR primers. Each pair of PCR primers included a first primer A and a second primer B that were designed to hybridize to and to amplify a region of mouse genomic DNA that encompasses a known polymorphic site. The second step, a multiplex allele-specific primer extension (ASPE) reaction, included a multiplexed set of tagged allele-specific primers. Each tagged allele-specific primer included a 5' tagging sequence containing non-standard nucleotides (iso-G), followed by a c3 (n-propylene) spacer, followed by a 3' sequence designed to hybridize to one of the DNA strands amplified in the previous multiplex PCR step. The allele specificity was determined by the 3' nucleotide of each tagged allele-specific primer. The multiplexed set of tagged allele-specific primers was designed to query the set of known polymorphic sites embedded in the set of multiplex PCR amplified sequences. A labeled triphosphate (dATP-Biotin) was added to the ASPE reaction, so that allele-specific extension of a tagged allele-specific primer led to the incorporation of dATP-Biotin. Unincorporated dATP-Biotin was removed prior to the subsequent capture step.

The third step, capture of the multiplex ASPE reaction products, used capture sequences containing non-standard nucleotides (iso-C) that were each covalently coupled to unique Luminex™ microsphere identities. The capture sequences were complementary to the tagging sequences used in the set of tagged allele-specific primers in the preceding ASPE reaction. Phycoerethrin was added to bind to the Biotin label on the extended tagged allele-specific primer strands and provide a fluorescent signal. Following hybridization between the capture sequences and the tagging sequences, the microspheres were injected into a Luminex100™ instrument to detect signal associated with each unique microsphere identity.

Nine polymorphic regions of the mouse genome were targeted in this example:

| Target | SEQ ID NO: | Sequence | A/J | C57BL6/J |
|---|---|---|---|---|
| 2 | 104 | AGAAACAACCATCTAATCCCACACTAAAAT TCAAGGCTCCACAGACGAAACAGTGAAGA TAATTGTTCAGCATACTAACCAACTGATTA CATATTTACCATACTCAGGTTTGTGCTTCA TACAAACCCAC/TAGTCCGGCGCTCCCTGTT GATG | CC | TT |

-continued

| Target | SEQ ID NO | Sequence | A/J | C57BL6/J |
|---|---|---|---|---|
| 3 | 105 | CTTCTCCCATTGCCCAGGGCACTCTCCTCT GTAGAA/GTAGACTGATC/TTTTGTGGAGACATCA | GG | AA |
| 4 | 106 | AGTGCCTGCTACCTGTCAGGTGAAAATTTC TTAGTGATCCC/TAAGCTCAATGGGTGCYGGGC TTGCAGG | CC | TT |
| 5 | 107 | GGTTGGAATGTTTGCACATGCAGTGTTAGT TATTTGGGC/TGATAACTACTTAGCTTATCT GCCTGGTCCAGC | TT | CC |
| 6 | 108 | CTGATCTGACCTCAGACTGTTGTGCTAACA GATATAACACCAGTAAGTTGAC/GTCAAAT TGCAGGAAGTAGAGCCTTGC | GG | CC |
| 7 | 109 | GACTGCTGGAGAGCTGAGGGAGGCTGTGGA GAATAAGGAGAGAGCA/GTAGTCTCGTGCCCT GCCCTGCCCATACTGAGCAGCCAAGACAC | GG | AA |
| 8 | 110 | GGACTGTCCAAAKGGATCTCAAGGAGAAT GTCCTTGCTATTAA/GGAGTATAAAGGCATAA AAGAGGTCATAGGGGACAACCATGACCAAG AAGTTG | AA | GG |
| 9 | 111 | CCTTCCTGCAYTCCACAGTATAAACACAGA ATGCACACTGCA/GGTCGTTGTATTTGTGTTC GATGTGAATTAAAGATGCTTTGGCTAAGCC AGGAGATGATAATACTG | AA | GG |
| 10 | 112 | CACATACACCATGTCAGCCATCAGCGCAAA GCCTTCGAGTTTCAGCTGTGAGATGAAGGC TTGGAGAAGCACGTTGATCTGCAAAGAAG AAAGGAGCTAGCGGAGGCC/TGGTCACTGACC GACTGCTCA | CC | TT |

The following nucleic acids were used in the multiplex PCR step for this example:

| Nucleic acid component | Sequence | SEQ ID NO |
|---|---|---|
| PCR Primer 1A | 5'-CATCTAACAGGGAGCGCC-3' | 113 |
| PCR Primer 1B | 5'-6FAM-AGAAACAACCATCTAATCCCACA-3' | 114 |
| PCR Primer 2A | 5'-6FAM-CTTCTCCCATTGCCCAGG-3' | 115 |
| PCR Primer 2B | 5'-TGATGTCTCCACAAAGATCAGTC-3' | 116 |
| PCR Primer 3A | 5'-AGTGCCTGCTACCTGTCAG-3' | 117 |
| PCR Primer 3B | 5'-6FAM-CCTGCAAGCCAGCACC-3' | 118 |
| PCR Primer 4A | 5'-6FAM-GGTTGGAATGTTTGCACATGC-3' | 119 |
| PCR Primer 4B | 5'-GCTGGACCAGGCTAGATAAGC-3' | 120 |
| PCR Primer 5A | 5'-6FAM-CTGATCTGACCTCAGACTGTTG-3' | 121 |
| PCR Primer 5B | 5'-GCAAGGCTCTACTTCCTGC-3' | 122 |
| PCR Primer 6A | 5'-6FAM-GACTGCTGGAGAGCTGAGG-3' | 123 |
| PCR Primer 6B | 5'-GTGTCTTGGCTGCTCAGTATG-3' | 124 |
| PCR Primer 7A | 5'-6FAM-GGACTGTCCAAAGGGATCTC-3' | 125 |
| PCR Primer 7B | 5'-CAACTTCTTGGTCATGGTTGTC-3' | 126 |
| PCR Primer 8A | 5'-Cy3-CCTTCCTGCAYTCCACAG-5' | 127 |

| Nucleic acid component | Sequence | SEQ ID NO |
|---|---|---|
| PCR Primer 8B | 5'-6FAM-CAGTATTATCATCTCCTGGCTTAGC-3' | 128 |
| PCR Primer 9A | 5'-6FAM-CACATACACCATGTCAGCC-3' | 129 |
| PCR Primer 9B | 5'-TGAGCAGTCGGTCAGTG-3' | 130 |
| Template 1 | Mouse genomic DNA; Strain: A/J | |
| Template 2 | Mouse genomic DNA; Strain: C57BL6/J | |

PCR primers were synthesized and diluted in 1 mM MOPS pH 7.5, 0.1 mM EDTA. The 6FAM or Cy3 fluor on some of the PCR primers is added to allow investigation of the multiplex PCR reaction on a polyacrylamide gel.

Mouse genomic DNA samples were purchased from the Jackson Laboratory (Bar Harbor, Me.). All genomic DNA samples were diluted to 5 ng/µL in 1 mM MOPS pH 7.5, 0.1 mM EDTA. PCR reaction components were:

| Component | 1X Concentration | Supplier and Location |
|---|---|---|
| 10X PCR Buffer II | 1.2 X | Applied Biosystems, Foster City, CA |
| MgCl$_2$ | 2 mM | Sigma, St. Louis, MO |
| dATP | 200 µM | Amersham |
| dGTP | 200 µM | Amersham |
| dCTP | 200 µM | Amersham |
| dTTP | 200 µM | Amersham |
| Amplitaq™ Gold DNA Polymerase | 0.1 U/µL | Applied Biosystems, Foster City, CA |
| PCR Primers (each) | 0.1 µM | |

A Master Mix of all listed components was prepared at 1.09× concentration for 25 µL final reaction volumes. 23 µL Master Mix was combined with 2 µL of genomic DNA template (5 ng/µL) in individual PCR tubes. A negative control included water in place of genomic DNA template. PCR reactions were cycled as follows:

| Cycle # | Step | Temp | Time |
|---|---|---|---|
| 1 | 1 | 95° C. | 9 minutes |
| 2-41 | 1 | 95° C. | 5 seconds |
| | 2 | 55° C. | 30 seconds |
| | 3 | 62° C. | 30 seconds |
| 42 | 1 | 62° C. | 5 minutes |
| 43 | 1 | 4° C. | hold |

Following PCR cycling, 2 µL of each PCR reaction was transferred to act as template in the multiplex ASPE reaction. The following synthetic nucleic acids were used as tagged allele-specific (TAS) primers in the multiplex ASPE reaction:

| Nucleic acid component | Sequence | SEQ ID NO |
|---|---|---|
| TAS Primer 1 | 5'-GTGYACAYGC-c3-GCTTCATACAAACCCAC-3' | 131 |
| TAS Primer 2 | 5'-CGAYTCTGYC-c3-GCTTCATACAAACCCAT-3' | 132 |
| TAS Primer 3 | 5'-CTAYCAAYCC-c3-CACTCTCCTCTGTAGAA-3' | 133 |
| TAS Primer 4 | 5'-GAGAYCYAAG-c3-CACTCTCCTCTGTAGAG-3' | 134 |
| TAS Primer 5 | 5'-GTTCYTGAYG-c3-GAAAATTTCTTAGTGATCCT-3' | 135 |
| TAS Primer 6 | 5'-GCYTAYCTAC-c3-AAAATTTCTTAGTGATCCC-3' | 136 |
| TAS Primer 7 | 5'-GTTAYCYTCC-c3-AGTGTTAGTTATTTGGGT-3' | 137 |
| TAS Primer 8 | 5'-CACYATACYG-c3-GTGTTAGTTATTTGGGC-3' | 138 |
| TAS Primer 9 | 5'-CYTACCYATG-c3-TAACACCAGTAAGTTGAC-3' | 139 |
| TAS Primer 10 | 5'-GYCGAYAATC-c3-TAACACCAGTAAGTTGAG-3' | 140 |
| TAS Primer 11 | 5'-GYCGTAYTTG-c3-AGAATAAGGAGAGAGCA-3' | 141 |
| TAS Primer 12 | 5'-GTYTATYCCG-c3-GAATAAGGAGAGAGCG-3' | 142 |
| TAS Primer 13 | 5'-GACAYACYTC-C3-AGAATAGTCCTTGCTATTAA-3' | 143 |
| TAS Primer 14 | 5'-GGAAYAACYG-C3-AGAATAGTCCTTGCTATTAG-3' | 144 |
| TAS Primer 15 | 5'-GATYTYCAGC-c3-AGAATGCACACTGCA-3' | 145 |

-continued

| Nucleic acid component | Sequence | SEQ ID NO |
|---|---|---|
| TAS Primer 16 | 5'-GTYATYTGCG-c3-GAATGCACACTGCG-3' | 146 |
| TAS Primer 17 | 5'-GATYGTCYYG-c3-GCTAGCGGAGGCC-3' | 147 |
| TAS Primer 18 | 5'-GGYCTYATGG-c3-GCTAGCGGAGGCT-3' | 148 |

Components of the ASPE reaction were:

| Component | 1X Concentration | Supplier and Location |
|---|---|---|
| Bis-Tris-Propane pH 8.9 | 10 mM | Sigma, St. Louis, MO |
| Potassium Acetate | 40 mM | Sigma, St. Louis, MO |
| $MgCl_2$ | 2 mM | Sigma, St. Louis, MO |
| Biotin-11-dATP | 4 µM | NEN, Boston, MA |
| dGTP | 200 µM | Amersham Pharmacia, Piscataway, NJ |
| dCTP | 200 µM | Amersham Pharmacia, Piscataway, NJ |
| dTTP | 200 µM | Amersham Pharmacia, Piscataway, NJ |
| Amplitaq™ Gold DNA Polymerase | 0.067 U/µL | Applied Biosystems, Foster City, CA |
| TAS Primers (each) | 0.067 µM | EraGen Biosciences, Inc., Madison, WI |

A Master Mix containing all of the above components except TAS primers was prepared at 1.36×. Each ASPE reaction consisted of 11 µL Master Mix, 2 µL multiplex TAS primer mix (0.5 µM each), 2 µL PCR reaction (from previous step). ASPE reactions were cycled as follows:

| Cycle # | Step | Temp | Time |
|---|---|---|---|
| 1 | 1 | 95° C. | 12 minutes |
| 2-5 | 1 | 95° C. | 3 seconds |
|  | 2 | 48° C. | 15 seconds |
|  | slow ramp | 30 degrees per minute |  |
|  | 3 | 62° C. | 30 seconds |
| 6 | 1 | 4° C. | hold |

Following ASPE cycling, 10 µL of the reaction volume was combined with 5 µL of a solution containing 40 mM Tris, 40 mM EDTA to stop the activity of the polymerase. The reaction was purified over a G-50 column to remove unincorporated dATP-Biotin. The purified multiplex ASPE reaction was then deconvoluted by capture sequences coupled to Luminex™ microspheres (Luminex Corp, Houston, Tex.). The coupled microspheres were:

| Microsphere Identity | SEQ ID NO: | Capture Sequence |
|---|---|---|
| 1 | 2 | CXGTTXTTCC |
| 2 | 9 | CATXGGTAXG |
| 7 | 14 | CGGXATAXAC |
| 15 | 13 | CAAXTACGXC |
| 17 | 22 | GCTGXAXATC |
| 18 | 23 | CGCAXATXAC |
| 19 | 1 | GAXGTXTGTC |
| 20 | 3 | GGXTTGXTAG |
| 21 | 4 | CTTXGXTCTC |
| 22 | 5 | CXTCAXGAAC |
| 34 | 7 | GGAXGXTAAC |
| 35 | 8 | CXGTATXGTG |
| 37 | 6 | GTAGXTAXGC |
| 38 | 10 | GATTXTCGXC |
| 45 | 28 | CXXGACXATC |
| 47 | 29 | CCATXAGXCC |
| 61 | 36 | GCXTGTXCAC |
| 62 | 37 | GXCAGAXTCG |

The coupled microspheres were combined in a mixture containing equal numbers of each microsphere identity in a storage buffer (10 mM MOPS pH 7.5, 200 mM NaCl, 1 mM EDTA, 1% PEG8000, 0.05% SDS). The components of the capture hybridization reaction were:

| Component | 1X Concentration | Supplier and Location |
|---|---|---|
| MOPS pH 7.5 | 10 mM | Fisher Chemical, Fair Lawn, NJ |
| NaCl | 200 mM | Fisher Chemical, Fair Lawn, NJ |
| $MgCl_2$ | 50 mM | Sigma, St. Louis, MO |
| EDTA | 1 mM | Fisher Chemical, Fair Lawn, NJ |
| PEG8000 | 1% | Sigma, St. Louis, MO |
| SDS | 0.05% | Fisher Chemical, Fair Lawn, NJ |
| Herring sperm DNA | 0.1 mg/mL | Promega, Madison, WI |
| Microsphere mix | 1000 each identity | EraGen Biosciences, Inc., Madison, WI |

A Master Mix of all listed components was prepared at 1.2× concentration for 60 µL final reaction volume. 50 µL Master Mix was combined with 10 µL of the purified multiplex ASPE reaction and allowed to hybridize at room temperature for 10 minutes. 10 µL of a 0.01 mg/mL solution of Streptavidin Phycoerethrin (Molecular Probes, Eugene, Oreg.) in hybridization buffer (10 mM MOPS pH7.5, 200 mM NaCl, 50 mM $MgCl_2$, 1 mM EDTA, 1% PEG8000, 0.05% SDS) was added to each capture hybridization reaction prior to injection into a Luminex100™ instrument.

Figure 14:
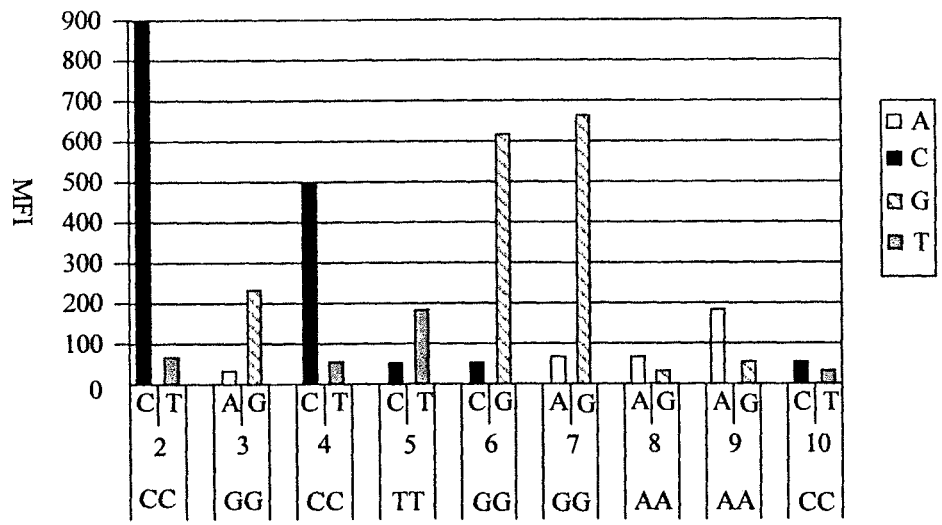
FIG. 14 is a graph illustrating results from an assay of alleles, according to the invention.
Figure 14:
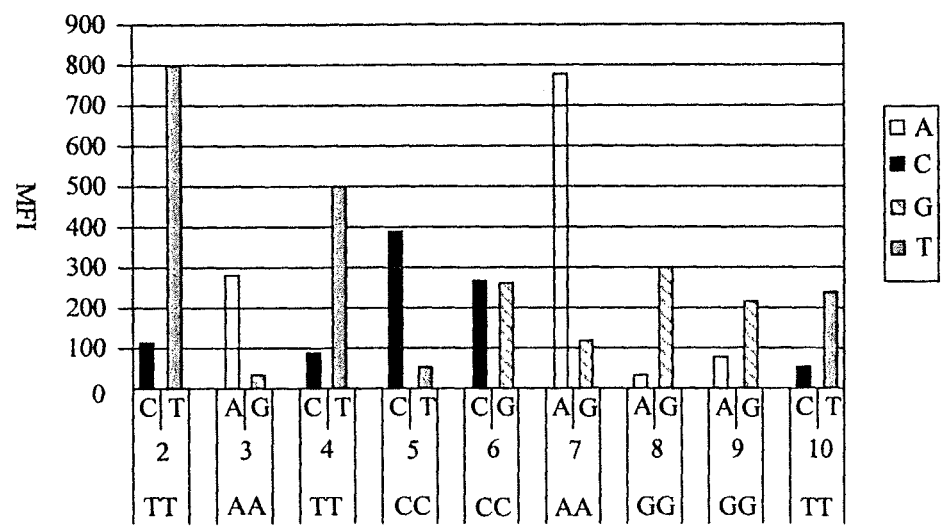

For each capture hybridization reaction, 55 μL was injected into the Luminex100™ at a rate of 60 μL/min and the read continued until 50 of each microsphere identity were counted. The median fluorescence intensity was used as a measurement of the fluorescent signal associated with each microsphere identity. The results are shown in FIG. 14.

Example 6

Multiplexed Genotyping of Genomic DNA Using Site-specific Incorporation of a Labeled Non-standard Base and Capture on Solid Support Microspheres The genotypes of nine polymorphic loci were determined following the amplification, query, and capture of targeted nucleic acid sequences from genomic DNA samples. The first step, a multiplex PCR reaction, included a multiplexed set of paired PCR primers. Each pair of PCR primers included a first primer A and a second primer B, and the second primer B included a non-standard nucleotide (iso-C) near its 5' end. Each primer pair was designed to hybridize to and to amplify a region of mouse genomic DNA that encompasses a known polymorphic site. The next step, a multiplex allele-specific primer extension (ASPE) reaction, included a multiplexed set of tagged allele-specific primers. Each tagged allele-specific primer included a 5' tagging sequence containing non-standard nucleotides (iso-G), followed by a c3 (n-propylene) spacer, followed by a 3' sequence designed to hybridize to one of the DNA strands amplified in the previous multiplex PCR step. The allele specificity was determined by the 3' nucleotide of each tagged allele-specific primer. The multiplexed set of tagged allele-specific primers was designed to query the set of known polymorphic sites embedded in the set of multiplex PCR amplified sequences. A labeled non-standard triphosphate (isoGTP-Biotin) was added to the ASPE reaction, so that allele-specific extension of a tagged allele-specific primer led to the incorporation of the labeled non-standard triphosphate (isoGTP-Biotin) opposite the non-standard nucleotide (iso-C) in the template strand created in the preceding multiplex PCR reaction. Unincorporated isoGTP-Biotin was removed prior to the subsequent capture step.

The third step, capture of the multiplex ASPE reaction products, used capture sequences containing non-standard nucleotides (iso-C) that were each covalently coupled to unique Luminex™ microsphere identities. The capture sequences were complementary to the tagging sequences used in the set of tagged allele-specific primers in the preceding ASPE reaction. Phycoerethrin was added to bind to the Biotin label on the extended tagged allele-specific primer strands and provide fluorescent signal. Following hybridization between the capture sequences and the tagging sequences, the microspheres were injected into a Luminex100™ instrument to detect signal associated with each unique microsphere identity.

Nine polymorphic regions of the mouse genome were targeted in this example:

| Target | SEQ ID NO: | Sequence | A/J | C57BL6/J | AB6F1 |
|---|---|---|---|---|---|
| 2 | 104 | AGAAACAACCATCTAATCCCACACTAAAAT TCAAGGCTCCACAGACGAAACAGTGAAGAA TAATTGTTCAGCATACTAACCAACTGATTA CATATTTACCATACTCAGGTTTGTGCTTCA TACAAACCCAC/TAGTCCGGCGCTCCCTGTTA GATG | CC | TT | CT |
| 3 | 105 | CTTCTCCCATTGCCCAGGGCACTCTCCTCT GTAGAA/GTAGACTGATYTTTGTGGAGACATC A | GG | AA | AG |
| 4 | 106 | AGTGCCTGCTACCTGTCAGGTGAAAATTTC TTAGTGATCCC/TAAGCTCAATGGGTGCYGGC TTGCAGG | CC | TT | CT |
| 5 | 107 | GGTTGGAATGTTTGCACATGCAGTGTTAG TATTTGGGC/TGATAACTACTTAGCTTATC GCCTGGTCCAGC | TT | CC | CT |
| 6 | 108 | CTGATCTGACCTCAGACTGTTGTGCTAACA GATATAACACCAGTAAGTTGAC/GTCAAATAC TGCAGGAAGTAGAGCCTTGC | GG | CC | CG |
| 7 | 109 | GACTGCTGGAGAGCTGAGGGAGGCTGTGGA GAATAAGGAGAGAGCA/GTAGTCTCGTGCCCT GCCCTGCCCATACTGAGCAGCCAAGACAC | GG | AA | AG |
| 8 | 110 | GGACTGTCCAAAKGGATCTCAAGGAGAATA GTCCTTGCTATTAA/GGAGTATAAAGGCATAA AAGAGGTCATAGGGGACAACCATGACCAAG AAGTTG | AA | GG | AG |
| 9 | 111 | CCTTCCTGCAYTCCACAGTATAAACACAG ATGCACACTGCA/GGTCGTTGTATTTGTGT GATGTGAATTAAAGATGCTTTGGCTAAGC AGGAGATGATAATACTG | AA | GG | AG |
| 10 | 112 | CACATACACCATGTCAGCCATCAGCGCAA GCCTTCGAGTTTCAGCTGTGAGATGAAGG TTGGAGAAGCACGTTGATCTGCAAAGAAGC | CC | TT | CT |

-continued

| Target | SEQ ID NO: | Sequence | A/J | C57BL6/J | AB6F1 |
|---|---|---|---|---|---|
| | | AAAGGAGCTAGCGGAGGCC/TGGTCACTGACC GACTGCTCA | | | |

The following nucleic acids were used in the multiplex PCR step for this example:

| Nucleic acid component | Sequence | SEQ ID NO |
|---|---|---|
| PCR Primer 1A | 5'-6FAM-AGAAACAACCATCTAATCCCACA-3' | 114 |
| PCR Primer 1B | 5'-TXCATCTAACAGGGAGCGCC-3' | 157 |
| PCR Primer 2A | 5'-6FAM-CTTCTCCCATTGCCCAGG-3' | 115 |
| PCR Primer 2B | 5'-TXTGATGTCTCCACAAAGATCAGTC-3' | 158 |
| PCR Primer 3A | 5'-6FAM-CCTGCAAGCCAGCACC-3' | 118 |
| PCR Primer 3B | 5'-TXCCTGCAAGCCAGCACC-3' | 159 |
| PCR Primer 4A | 5'-6FAM-GGTTGGAATGTTTGCACATGC-3' | 119 |
| PCR Primer 4B | 5'-TXGCTGGACCAGGCTAGATAAGC-3' | 160 |
| PCR Primer 5A | 5'-6FAM-CTGATCTGACCTCAGACTGTTG-3' | 121 |
| PCR Primer 5B | 5'-TXGCAAGGCTCTACTTCCTGC-3' | 161 |
| PCR Primer 6A | 5'-6FAM-GACTGCTGGAGAGCTGAGG-3' | 123 |
| PCR Primer 6B | 5'-TXGTGTCTTGGCTGCTCAGTATG-3' | 162 |
| PCR Primer 7A | 5'-6FAM-GGACTGTCCAAAGGGATCTC-3' | 125 |
| PCR Primer 7B | 5'-TXCAACTTCTTGGTCATGGTTGTC-3' | 163 |
| PCR Primer 8A | 5'-6FAM-CAGTATTATCATCTCCTGGCTTAGC-3' | 128 |
| PCR Primer 8B | 5'-TXCCTTCCTGCACTCCACAG-3' | 164 |
| PCR Primer 9A | 5'-6FAM-CACATACACCATGTCAGCC-3' | 129 |
| PCR Primer 9B | 5'-TXTGAGCAGTCGGTCAGTG-3' | 165 |
| Template 1 | Mouse genomic DNA; Strain: A/J | |
| Template 2 | Mouse genomic DNA; Strain: C57BL6/J | |
| Template 3 | Mouse genomic DNA; Strain: AB6F1 | |

PCR primers were synthesized and diluted in 1 mM MOPS pH 7.5, 0.1 mM EDTA. Mouse genomic DNA samples were purchased from the Jackson Laboratory in (Bar Harbor, Me.). All genomic DNA samples were diluted to 5 ng/µL in 1 mM MOPS pH 7.5, 0.1 mM EDTA. PCR reaction components were:

| Component | 1X Concentration | Supplier and Location |
|---|---|---|
| 10X PCR Buffer II | 1.2 X | Applied Biosystems, Foster City, CA |
| MgCl$_2$ | 2 mM | Sigma, St. Louis, MO |
| DATP | 200 µM | Amersham |
| DGTP | 200 µM | Amersham |
| DCTP | 200 µM | Amersham |

-continued

| Component | 1X Concentration | Supplier and Location |
|---|---|---|
| DTTP | 200 µM | Amersham |
| Amplitaq ™ Gold DNA Polymerase | 0.1 U/µL | Applied Biosystems, Foster City, CA |
| PCR Primers (each) | 0.2 µM | |

A Master Mix of all listed components was prepared at 1.09× concentration for 25 µL final reaction volumes. 23 µL Master Mix was combined with 2 µL of genomic DNA template (5 ng/µL) in individual PCR tubes. A negative control included water in place of genomic DNA template. PCR reactions were cycled as follows:

| Cycle # | Step | Temp | Time |
|---|---|---|---|
| 1 | 1 | 95° C. | 9 minutes |
| 2-41 | 1 | 95° C. | 10 seconds |
| | 2 | 55° C. | 10 seconds |
| | 3 | 70° C. | 30 seconds |
| 42 | 1 | 70° C. | 5 minutes |
| 43 | 1 | 4° C. | hold |

Following PCR cycling, 2 µl, of each PCR reaction was transferred to act as template in the multiplex ASPE reaction. The following synthetic nucleic acids were used as tagged allele-specific (TAS) primers in the multiplex ASPE reaction:

| Nucleic acid component | Sequence | SEQ ID NO |
|---|---|---|
| TAS Primer 1 | 5'-GTGYACAYGC-c3-GCTTCATACAAACCCAC-3' | 131 |
| TAS Primer 2 | 5'-CGAYTCTGYC-c3-GCTTCATACAAACCCAT-3' | 132 |
| TAS Primer 3 | 5'-CTAYCAAYCC-c3-CACTCTCCTCTGTAGAA-3' | 133 |
| TAS Primer 4 | 5'-GAGAYCYAAG-c3-CACTCTCCTCTGTAGAG-3' | 134 |
| TAS Primer 5 | 5'-GTTCYTGAYG-c3-GAAAATTTCTTAGTGATCCT-3' | 135 |
| TAS Primer 6 | 5'-GCYTAYCTAC-c3-AAAATTTCTTAGTGATCCC-3' | 136 |
| TAS Primer 7 | 5'-GTTAYCYTCC-c3-AGTGTTAGTTATTTGGGT-3' | 137 |
| TAS Primer 8 | 5'-CACYATACYG-c3-GTGTTAGTTATTTGGGC-3' | 138 |
| TAS Primer 9 | 5'-CYTACCYATG-c3-TAACACCAGTAAGTTGAC-3' | 139 |
| TAS Primer 10 | 5'-GYCGAYAATC-c3-TAACACCAGTAAGTTGAG-3' | 140 |
| TAS Primer 11 | 5'-GYCGTAYTTG-c3-AGAATAAGGAGAGAGCA-3' | 141 |
| TAS Primer 12 | 5'-GTYTATYCCG-c3-GAATAAGGAGAGAGCG-3' | 142 |
| TAS Primer 13 | 5'-GACAYACYTC-C3-AGAATAGTCCTTGCTATTAA-3' | 143 |
| TAS Primer 14 | 5'-GGAAYAACYG-C3-AGAATAGTCMGCTATTAG-3' | 144 |
| TAS Primer 15 | 5'-GATYTYCAGC-c3-AGAATGCACACTGCA-3' | 145 |
| TAS Primer 16 | 5'-GTYATYTGCG-c3-GAATGCACACTGCG-3' | 146 |
| TAS Primer 17 | 5'-GATYGTCYYG-c3-GCTAGCGGAGGCC-3' | 147 |
| TAS Primer 18 | 5'-GGYCTYATGG-c3-GCTAGCGGAGGCT-3' | 148 |

Components of the ASPE reaction were:

| Component | 1X Concentration | Supplier and Location |
|---|---|---|
| Bis-Tris-Propane pH 8.9 | 10 mM | Sigma, St. Louis, MO |
| Potassium Acetate | 40 mM | Sigma, St. Louis, MO |
| MgCl$_2$ | 2 mM | Sigma, St. Louis, MO |
| dATP | 50 µM | Amersham Pharmacia, Piscataway, NJ |
| dGTP | 50 µM | Amersham Pharmacia, Piscataway, NJ |
| dCTP | 50 µM | Amersham Pharmacia, Piscataway, NJ |
| dTTP | 50 µM | Amersham Pharmacia, Piscataway, NJ |
| d-isoGTP-Biotin | 10 µM | EraGen Biosciences, Inc., Madison, WI |
| Klentaq DNA Polymerase | 0.067 U/µL | Ab Peptides, St. Louis, MO |
| TAS Primers (each) | 0.067 µM | EraGen Biosciences, Inc., Madison, WI |

A Master Mix containing all of the above components was prepared at 1.15×. Each ASPE reaction consisted of 13 µL Master Mix and 2 µL PCR reaction (from previous step). ASPE reactions were cycled as follows:

| Cycle # | Step | Temp | Time |
|---|---|---|---|
| 1 | 1 | 95° C. | 2 minutes |
| 2-11 | 1 | 95° C. | 1 seconds |
| | 2 | 48° C. | 1 seconds |
| | 3 | 72° C. | 1 minutes |
| 12 | 1 | 72° C. | 5 minutes |
| 13 | 1 | 4° C. | hold |

Following ASPE cycling, 5 µL of a solution containing 40 mM Tris, 40 mM EDTA was added to the multiplex ASPE reaction to stop the activity of the polymerase. The reaction was purified over a G-50 column to remove unincorporated d-isoGTP-Biotin. The purified multiplex ASPE reaction was then deconvoluted by capture sequences coupled to Luminex™ microspheres (Luminex Corp, Houston, Tex.). The coupled microspheres were:

| Microsphere Identity | SEQ ID NO: | Capture Sequence |
|---|---|---|
| 1 | 2 | CXGTTXTTCC |
| 2 | 9 | CATXGGTAXG |
| 7 | 14 | CGGXATAXAC |
| 15 | 13 | CAAXTACGXC |
| 17 | 22 | GCTGXAXATC |
| 18 | 23 | CGCAXATXAC |
| 19 | 1 | GAXGTXTGTC |
| 20 | 3 | GGXTTGXTAG |
| 21 | 4 | CTTXGXTCTC |
| 22 | 5 | CXTCAXGAAC |
| 34 | 7 | GGAXGXTAAC |
| 35 | 8 | CXGTATXGTG |
| 37 | 6 | GTAGXTAXGC |
| 38 | 10 | GATTXTCGXC |
| 45 | 28 | CXXGACXATC |
| 47 | 29 | CCATXAGXCC |
| 61 | 36 | GCXTGTXCAC |
| 62 | 37 | GXCAGAXTCG |

The coupled microspheres were combined in a mixture containing equal numbers of each microsphere identity in a storage buffer (10 mM MOPS pH 7.5, 200 mM NaCl, 1 mM EDTA, 1% PEG8000, 0.05% SDS). The components of the capture hybridization reaction were:

| Component | 1X Concentration | Supplier and Location |
|---|---|---|
| MOPS pH 7.5 | 10 mM | Fisher Chemical, Fair Lawn, NJ |
| NaCl | 200 mM | Fisher Chemical, Fair Lawn, NJ |
| MgCl$_2$ | 50 mM | Sigma, St. Louis, MO |
| EDTA | 1 mM | Fisher Chemical, Fair Lawn, NJ |
| PEG8000 | 1% | Sigma, St. Louis, MO |
| SDS | 0.5% | Fisher Chemical, Fair Lawn, NJ |
| Herring sperm DNA | 0.1 mg/mL | Promega, Madison, WI |
| Microsphere mix | 1000 each identy | EraGen Biosciences, Inc., Madison, WI |

A Master Mix of all listed components was prepared at 1.2× concentration for 60 μL final reaction volume. 50 μL Master Mix was combined with 10 μL of the purified multiplex ASPE reaction and allowed to hybridize at room temperature for 10 minutes. 10 μL of a 0.01 mg/mL solution of Streptavidin Phycoerethrin (Molecular Probes, Eugene, Oreg.) in hybridization buffer (10 mM MOPS pH7.5, 200 mM NaCl, 50 mM MgCl$_2$, 1 mM EDTA, 1% PEG8000, 0.05% SDS) was added to each capture hybridization reaction prior to injection into a Luminex100™ instrument.

Figure 15A:
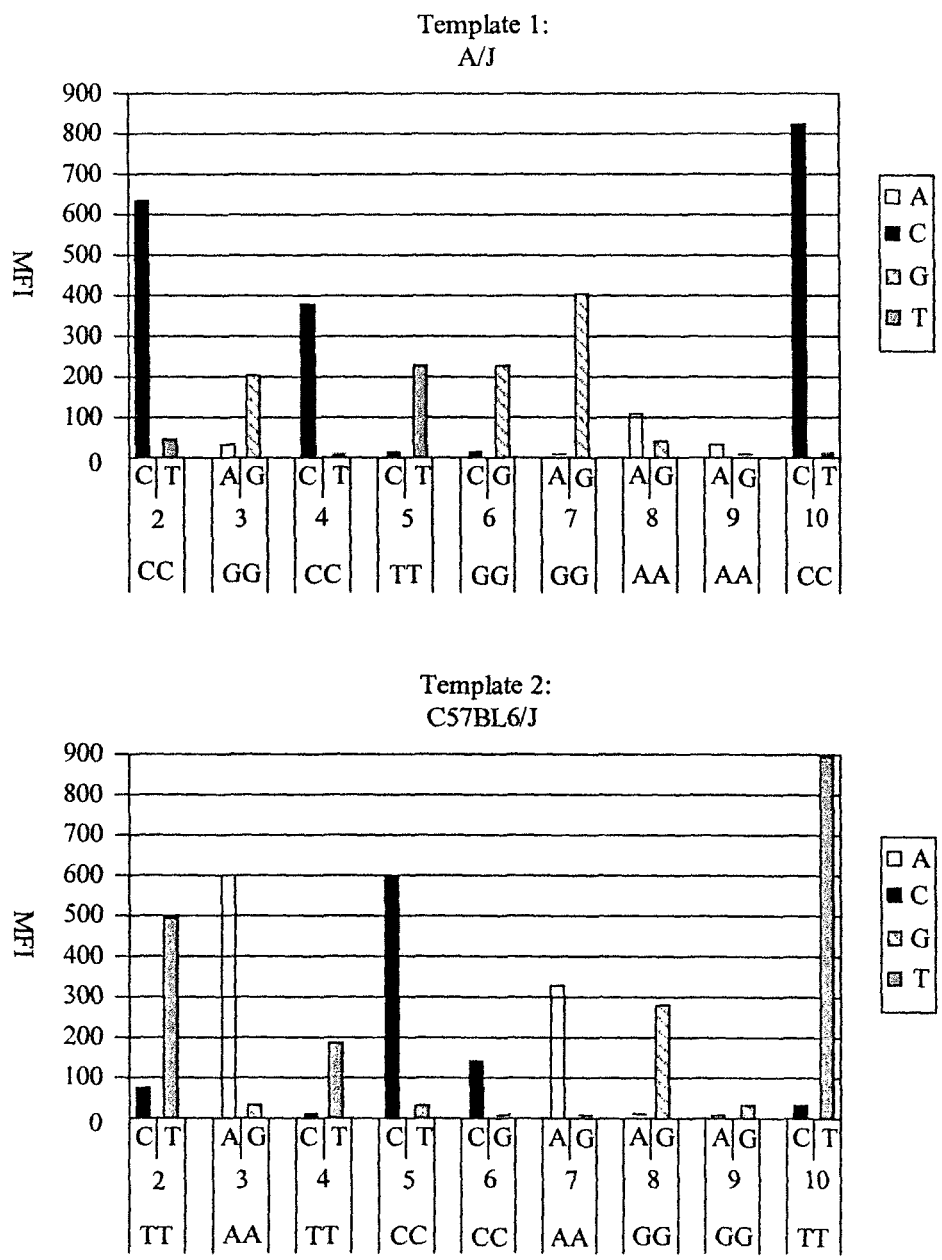
FIGS. 15A and 15B are graphs illustrating results from another assay of alleles, according to the invention.
Figure 15B:
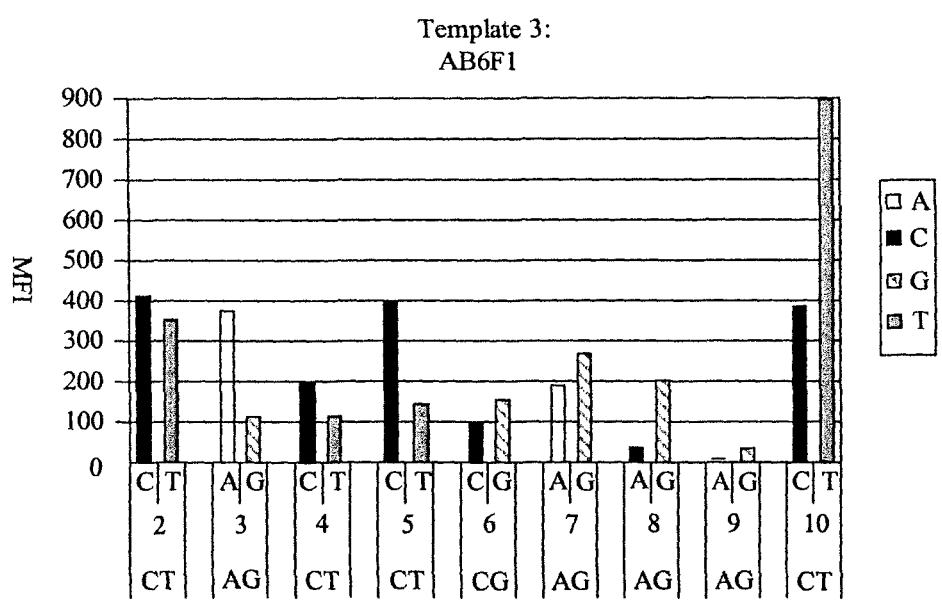

For each capture hybridization reaction, 55 μL was injected into the Luminex100™ at a rate of 60 μL/min and the read continued until 50 of each microsphere identity were counted. The median fluorescence intensity was used as a measurement of the fluorescent signal associated with each microsphere identity. The results are shown in FIG. 15.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

Example 7

Genotyping of Genomic DNA Using Site Specific Ligation of a Reporter Oligonucleotide to an Allele Specific Extension Product and Capture on Solid Support Microspheres The genotype of a polymorphic loci was determined following the amplification, query, and capture of target nucleic acid sequences from genomic DNA samples. The first step, a PCR reaction, included a set of PCR primers: a first primer A and a second primer B. The primer B contained a 5' sequence non-complementary to the target with an iso-C at the junction of the analyte specific and non-complementary portion. The primer pair was designed to hybridize to and amplify a region of mouse genomic DNA that encompasses a known polymorphic site. The second step, an allele specific primer extension (ASPE) reaction, included a set of tagged allele-specific primers. Each tagged allele-specific primer was composed of a 5' tagging sequence containing non-standard nucleotides (iso-G), followed by a c3 spacer, followed by a 3' sequence designed to hybridize to one of the DNA strands amplified in the previous PCR step. The allele specificity was determined by the 3' nucleotide of each tagged allele-specific primer. The set of tagged allele-specific primers was designed to query a known polymorphic site embedded in the amplified sequence. A DNA ligase and a reporter oligonucleotide containing a 5' phosphate, and a 3' biotin modifications were included in the ASPE reaction. This reporter oligonucleotide was complimentary to the 5' region of primer B used to generate the amplicon that was queried. The strand of the amplified product containing this non-standard base containing region served as the template for the ASPE reaction. During allele specific primer extension, the DNA polymerase terminates at the base prior to the iso-C in the template strand, thus leaving a single stranded region to which the reporter oligonucleotide to hybridize. The complex between the extended ASPE primer, the template, and the reporter oligonucleotide results in a nick structure suitable for ligation by a DNA ligase.

The third step, capture of the multiplex ASPE reaction products, used sequences containing non-standard nucleotides (iso-C) that were each covalently coupled to unique Luminex microsphere identities. The capture sequences were complementary to the tagging sequences used in the set of tagged allele-specific primers in the preceding ASPE reaction. Streptavidin-phycoerthrin was added to bind to the biotin label on the extended and ligated allele-specific primer strands to provide fluorescent signal. Following hybridization between the capture sequences and the tagging sequences, the microspheres were injected into a Luminex 100 instrument to detect signal associated with each unique microsphere identity.

A single polymorphic region of the mouse genome was targeted in this example:

| SEQ ID NO: | Target Sequence | A/J | C57BL6/J | AB6F1 |
|---|---|---|---|---|
| 149 | 5'CTTCTCCCATTGCCCAGGGCACTCT CCTCTGTAGARTAGACTGATMTG TGGAGACATCA 3' | GG | AA | AG |

| Nucleic Acid Component | Sequence 5'-3' | SEQ ID NO: |
|---|---|---|
| PCR Primer A | PO4-CTTCTCCCATTGCCCAGG | 115 |
| PCR Primer B | CXGCXAGXGATXTGATGTCTCCACAAAGATCAGTC | 150 |
| Template 1 | Mouse genomic DNA; Strain: A/J | |
| Template 1 | Mouse genomic DNA; Strain: C57BL6/J | |
| Template 1 | Mouse genomic DNA; Strain: AB6F1 | |

Mouse Genomic DNA samples were purchased from Jackson Laboratories (Bar Harbor, Me.). All genomic DNA samples were diluted to 10 ng/ul in 1 mM MOPS pH 7.5, 0.1 mM EDTA. PCR reaction components were:

| Component | 1X Concentration | Supplier and Location |
|---|---|---|
| 10X PCR Buffer II | 1.2 X | Applied Biosystems, Foster City, CA |
| MgCl2 | 2 mM | Sigma, St. Louis, MO |
| dGTP | 200 uM | Promega, Madison, WI |
| dATP | 200 uM | Promega, Madison, WI |
| dTTP | 200 uM | Promega, Madison, WI |
| dCTP | 200 uM | Promega, Madison, WI |
| Amplitaq DNA Polymerase Stoffel Fragment | 0.2 U/ul | Applied Biosystems, Foster City, CA |
| PCR Primer A | 0.2 uM | |
| PCR Primer B | 0.2 uM | |

A master mix of all listed components was prepared at 1.07× concentration for 30 ul final reaction volume. 23 ul of master mix was combined with 2 ul of genomic DNA template (5 ng/ul) in individual PCR tubes. A negative control included water in place of genomic DNA template. PCR reactions were thermal cycled as follows:

| Cycle # | Step | Temp | Time |
|---|---|---|---|
| 1 | 1 | 95° C. | 2 minutes |
| 2-41 | 1 | 95° C. | 10 seconds |
| | 2 | 55° C. | 10 seconds |
| | 3 | 65° C. | 30 seconds |
| 42 | 1 | 65° C. | 5 minutes |
| 43 | 1 | 4° C. | hold |

Following PCR cycling, 3 ul of 5 U/ul lambda exonuclease (New England Biolabs, Beverly, Mass.) was added to each reaction to remove the non-template strand of the amplicon created by PCR primer A. Following addition of lambda exonuclease the reaction tubes were heated to 37° C. for 5 minutes, then to 95° C. for 2 minutes. Following this digest, 1 ul of each PCR reaction was transferred to act as template in the ASPE reaction. The following nucleic acid sequences were used as tagged allele-specific (TAS) primers in the ASPE reaction:

| Nucleic acid component | Sequence 5'-3' | SEQ ID NO: |
|---|---|---|
| TAS Primer 1 | CTAYCAAYCC-c3-CACTCTCCT CTGTAGAA | 151 |
| TAS Primer 2 | GAGAYCYAAG-c3-CACTCTCCT CTGTAGAG | 152 |
| Reporter oligonucleotide | PO4-YATCYCTYGCYG-Biotin | 153 |

Components of the ASPE reaction were:

| Component | 1X Concentration | Supplier and Location |
|---|---|---|
| 10X PCR Buffer II | 1.2 X | Applied Biosystems, Foster City, CA |
| MgCl2 | 2 mM | Sigma, St. Louis, MO |
| DGTP | 200 uM | Promega, Madison, WI |
| DATP | 200 uM | Promega, Madison, WI |
| DTTP | 200 uM | Promega, Madison, WI |
| DCTP | 200 uM | Promega, Madison, WI |
| Amplitaq DNA Polymerase Stoffel Fragment | 0.1 U/ul | Applied Biosystems, Foster City, CA |
| TAS Primer 1 | 0.1 uM | |
| TAS Primer 2 | 0.1 uM | |
| Reporter oligonucleotide | 0.2 uM | |
| DTT | 5 mM | Fisher Scientific, Pittsburgh, PA |
| NAD | 1 mM | Roche, Indianapolis, IN |
| Taq DNA ligase | 2 U/ul | New England Biolabs, Beverly, MA |

A master mix containing all of the above components was prepared at 1.11×. Each ASPE reaction consisted of 9 ul master mix and 1 ul PCR reaction (from previous step). ASPE reactions were cycled as follows:

| Cycle # | Step | Temp | Time |
|---|---|---|---|
| 1 | 1 | 95° C. | 30 seconds |
| 2-13 | 1 | 95° C. | 1 seconds |
| | 2 | 48° C. | 1 seconds |
| | 3 | 58° C. | 2 minutes |
| 14 | 1 | 4° C. | hold |

Following ASPE cycling the reactions were deconvoluted by capture sequences coupled to Luminex microspheres (Luminex Corp, Austin, Tex.). The coupled microspheres were:

| Microsphere Identity | SEQ ID NO: | Capture sequence 5'-3' |
|---|---|---|
| 20 | 3 | GGXTTGXTAG |
| 21 | 4 | CTTXGXTCTC |

The coupled microspheres were combined in a mixture containing equal numbers of each microsphere identity in a storage buffer (10 mM MOPS pH 7.5, 200 mM NaCl, 1 mM EDTA, 1% PEG8000, 0.05% SDS), The components of the capture hybridization reaction were:

| Component | 1X Concentration | Supplier and Location |
|---|---|---|
| MOPS pH 7.5 | 10 mM | Sigma, St. Louis, MO |
| NaCl | 200 mM | Sigma, St. Louis, MO |
| $MgCl_2$ | 50 mM | Sigma, St. Louis, MO |
| EDTA | 1 mM | Sigma, St. Louis, MO |
| PEG 8000 | 1% | Sigma, St. Louis, MO |
| SDS | 0.05% | Sigma, St. Louis, MO |
| Herring Sperm DNA | 0.1 mg/ml | Promega, Madison, WI |
| Microsphere mix | 1000 each identity | Luminex Corp., Austin, TX |

A master mix containing all of the above components was prepared at 1.2× concentration for a 60 ul final reaction volume. 50 ul of this master mix was added to each ASPE reaction and allowed to hybridize for 10 minutes at room temperature. 10 ul of solution of streptavidin-phycoerythrin (0.075 mg/ml in 10 mM MOPS pH 7.5, NaCl 200 mM, $MgCl_2$ 50 mM, EDTA 1 mM, PEG 8000 1%, SDS 0.05) (Molecular Probes, Eugene, Oreg.) was added to each capture hybridization prior to injection into a Luminex 100 instrument.

Figure 17:
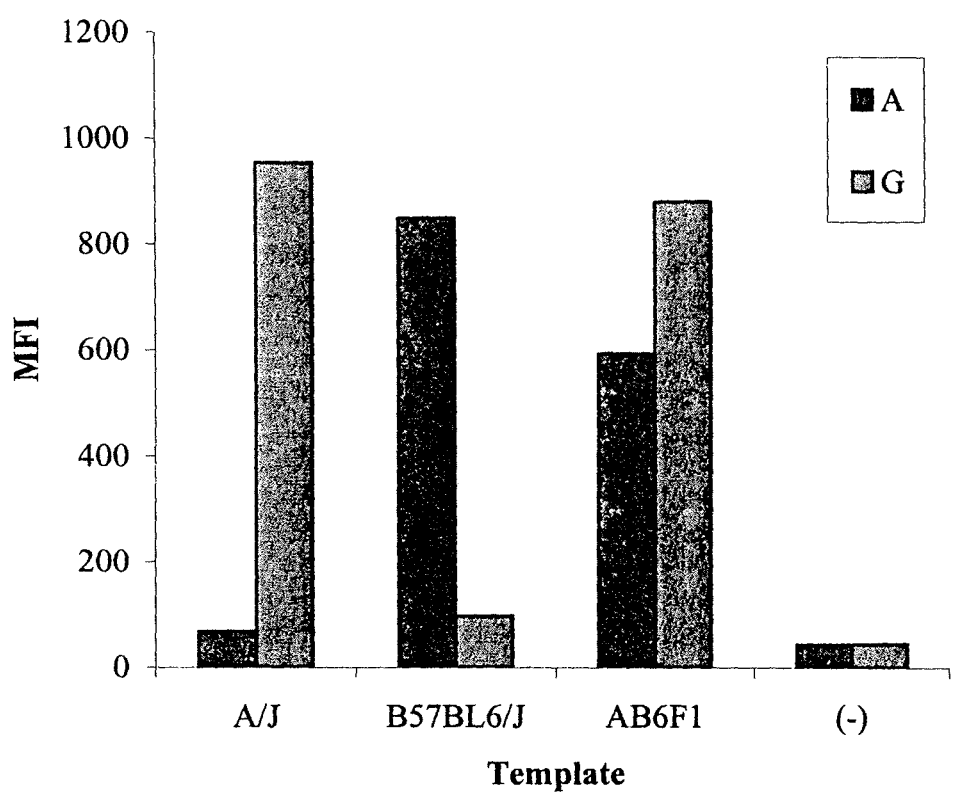
FIG. 17 is a graph of results from an assay of alleles, according to the invention.

For each capture hybridization reaction, 45 ul of the reaction mixture was injected into the Luminex 100 at a rate of 60 µl/min and the read continued until 100 of each microsphere identity were counted. The median fluorescence intensity (MFI) was used as a measurement of the fluorescent signal associated with each identity. The results are shown in FIG. 17.

In the above example, the non-standard base of primer B at the junction of the 5' non-complementary sequence and the analyte-specific sequence is designed to prevent extension by the polymerase at the junction of the tagging and analyte specific sequences. It is specifically envisioned that other suitable linkers may be used to stop the polymerase, including, for example, 2'-O-methyl bases such as 2'-O-methyl ribonucleotides.

What is claimed is:

1. A method for detecting a target nucleic acid in a sample comprising:
   a) synthesizing a nucleic acid comprising a copy of the target nucleic acid or a complement of the target nucleic acid using a reaction mixture that comprises (i) a first primer comprising a tagging sequence and a sequence complementary to a first sequence of the target nucleic acid or the complement of the target nucleic acid, (ii) a second primer comprising at least one non-natural base and a sequence complementary to a second sequence of the target nucleic acid or the complement of the target nucleic acid, and (iii) a labeled, non-natural nucleotide triphosphate having a non-natural base that is complementary to the non-natural base of the second primer;
   b) contacting the synthesized nucleic acid with an oligonucleotide bound to a solid support, wherein the oligonucleotide comprises a molecular recognition sequence that is complementary to the tagging sequence of the first primer; and
   c) detecting specific hybridization of the synthesized nucleic acid and the oligonucleotide bound to the solid support, thereby detecting the target nucleic acid.

2. The method of claim 1, wherein the label comprises a coupling agent.

3. The method of claim 2, wherein the coupling agent comprises biotin.

4. The method of claim 3, wherein the method further comprises contacting the synthesized nucleic acid with a streptavidin-phycoerythrin.

5. The method of claim 1, wherein the label comprises a fluorophore.

6. The method of claim 1, wherein the non-natural base is selected from the group consisting of iso-cytosine and iso-guanine.

7. The method of claim 1, wherein the target nucleic acid is detected quantitatively.

8. The method of claim 1, wherein the specific hybridization is detected without performing washing.

9. The method of claim 1, wherein the specific hybridization is detected at room temperature.

10. The method of claim 1, wherein the first primer comprises a n-propylene spacer between the tagging sequence and the sequence complementary to a first sequence of the target nucleic acid or the complement of the target nucleic acid.

11. The method of claim 1, wherein the tagging sequence and the molecular recognition sequence each comprise at least one non-natural base, and further wherein the at least one non-natural base of the tagging sequence is complementary to the at least one non-natural base of the molecular recognition sequence.

12. The method of claim 11, wherein the non-natural base is selected from the group consisting of iso-cytosine and iso-guanine.

* * * * *

UNITED STATES PATENT AND TRADEMARK OFFICE
CERTIFICATE OF CORRECTION

PATENT NO. : 8,518,671 B2  
APPLICATION NO. : 13/478586  
DATED : August 27, 2013  
INVENTOR(S) : Jennifer K. Grenier et al.

Page 1 of 1

It is certified that error appears in the above-identified patent and that said Letters Patent is hereby corrected as shown below:

In the Claims:

In claim 1, column 1, line 54, after the word "having" insert --a label and--.

In claim 1, column 1, line 55, after the word "primer" insert --, and forming a synthesized nucleic acid--.

In claim 1, column 1, line 61, after the word "detecting" insert --a--.

In claim 1, column 1, line 63, after the word "acid" insert --in the sample--.

In claim 4, column 2, line 42-43, delete "wherein the method further comprises" and insert --further comprising-- therefor.

In claim 10, column 2, line 59, delete "a" and insert --the-- therefor.

In claim 11, column 2, line 62, after the word "wherein" insert --each of--.

In claim 11, column 2, line 63, delete "each comprise" and insert --comprises-- therefor.

In claim 11, column 2, line 64, delete "further wherein".

Signed and Sealed this  
First Day of October, 2013

Teresa Stanek Rea  
*Deputy Director of the United States Patent and Trademark Office*